United States Patent
Hocum et al.

(10) Patent No.: US 11,410,744 B2
(45) Date of Patent: Aug. 9, 2022

(54) ERYTHROPOIETIC STIMULATING AGENT (ESA) DOSAGE DETERMINATION

(71) Applicant: Mayo Foundation for Medical Education and Research, Rochester, MN (US)

(72) Inventors: Craig L. Hocum, Winona, MN (US); James T. McCarthy, Rochester, MN (US); David P. Steensma, Wellesley, MA (US); David Dingli, Rochester, MN (US); Edward J. Gallaher, Hillsboro, OR (US); James L. Rogers, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1149 days.

(21) Appl. No.: 15/928,717

(22) Filed: Mar. 22, 2018

(65) Prior Publication Data
US 2018/0218110 A1 Aug. 2, 2018

Related U.S. Application Data

(63) Continuation of application No. 13/519,843, filed as application No. PCT/US2011/020120 on Jan. 4, 2011, now abandoned.

(60) Provisional application No. 61/292,087, filed on Jan. 4, 2010.

(51) Int. Cl.
  *G16B 5/00* (2019.01)
  *G16H 50/50* (2018.01)

(52) U.S. Cl.
  CPC .............. *G16B 5/00* (2019.02); *G16H 50/50* (2018.01)

(58) Field of Classification Search
  None
  See application file for complete search history.

(56) References Cited

U.S. PATENT DOCUMENTS

| | | |
|---|---|---|
| 6,747,002 B2 | 6/2004 | Cheung et al. |
| 2003/0198691 A1 | 10/2003 | Cheung et al. |
| 2004/0176297 A1 | 9/2004 | Cheung et al. |
| 2007/0196479 A1 | 8/2007 | Willmann et al. |
| 2009/0006129 A1 | 1/2009 | Thukral et al. |

OTHER PUBLICATIONS

Gaweda et al. American Journal of Kidney Diseases, vol. 51, Issue 1, Jan. 2008, pp. 71-79.*
Response to Summons to Invitation pursuant to Rule 137(4) EPC and Article 94(3) EPC from European Patent Application No. 11700870.6, dated Jun. 1, 2021, filed Jul. 9, 2021, 11 pp
Response to Canadian Office Action dated Feb. 26, 2018, from counterpart Canadian application No. 2,786,297, filed Aug. 26, 2018, 9 pp.
Response to Canadian Office Action dated Dec. 21, 2020, from counterpart Canadian application No. 3,058,773, filed Apr. 20, 2021, 13 pp.
Invitation pursuant to Rule 137(4) EPC and Article 94(3) EPC from International Application No. 11700870.6, dated Jun. 1, 2021, 2 pp.
Office Action from counterpart Canadian Application No. 3,058,773 dated Sep. 9, 2021, 4 pp.
Sheiner et al. Bayesian Individualization of Pharmacokinetics: Simple Implementation and Comparison with Non-Bayesian Methods. Journal of Pharmaceutical Sciences, vol. 71, No. 12, 1344-1348 1982.
Response to Office Action dated Feb. 20, 2014, from counterpart Canadian Patent Application No. 2,786,297, filed Aug. 20, 2014, 8 pp.
Office Action and Examination Search Report from counterpart Canadian Application No. 2,786,297, dated Feb. 20, 2015, 4 pp.
Response to Canadian Office Action dated Feb. 20, 2015, from counterpart Canadian Application No. 2,786,297, filed on Aug. 20, 2015, 4 pp.
Office Action from counterpart Japanese Application No. 2014-158201, dated Aug. 17, 2015, 5 pp.
Response to First Examination Report dated May 28, 2013. from counterpart Australian Application No. 2011203456, filed Jun. 26, 2014, 15 pp.
Decision of Rejection from counterpart Japanese Patent Application No. 2012-547335, dated Apr. 1, 2014,5 pp.
Notice of Acceptance for counterpart Australian Application No. 2011203456 82, issued by Australian Government IP Australia dated Jul. 22, 2014,3 pp.
Canadian Office Action from Canadian counterpart patent application No. 2,786.297, dated Feb. 20, 2014, 2 pp.
Japanese Official Action with English translation from corresponding Japanese application No. 2012-547335, dated Dec. 10, 2013, 4 pp.
Patent Examination Report No. 1 dated May 28, 2013 by the Australian Government IP Australia for corresponding Australian patent application No. 2011203456.
Bellazzi et al., "Mathematical Modeling of Erythropoietin Therapy in Uremic Anemia. Does it Improve Cost-Effectiveness?", Haematologica ,vol. 79, pp. 154-164, 1994.
International Search Report and Written Opinion of the International Searching Authority, or Declaration for corresponding application No. PCT/US2011/020120, dated Apr. 4, 2011, 13 pages.

(Continued)

*Primary Examiner* — Michael L Borin
(74) *Attorney, Agent, or Firm* — Shumaker & Sieffert, P.A.

(57) ABSTRACT

An Erythropoietic Stimulating Agent (ESA) dosing system/method determines patient-specific ESA therapies for patients affected by insufficient hemoglobin production that may benefit from ESA treatment. The ESA dosing system includes a model that represents a process by which red blood cells are produced in humans. The model may include one or more parameters, the values of which are patient-specific. The model takes into account patient-specific historical hemoglobin (Hgb) data and corresponding historical ESA dosage data to estimate the patient-specific values of the model parameters, and determines a target therapeutic dose of the ESA that may maintain the patient's Hgb within a target range.

19 Claims, 35 Drawing Sheets

(56) References Cited

OTHER PUBLICATIONS

International Preliminary Report on Patentability (Chapter I of the Patent Cooperation Treaty) for corresponding application No. PCT/US2011/020120, dated Jul. 12, 2012, 8 pages.
Office Action from counterpart Canadian Application No. 2,786,297, dated Feb. 15, 2016, 3 pp.
Office Action from counterpart Canadian Application No. 2,786,297, dated Feb. 26, 2018, 5 pp.
Prosecution History from U.S. Appl. No. 13/519,843, dated Jun. 28, 2012 through Jan. 26, 2018, 120 pp.
Examination Report from counterpart European Application No. 11700870.6, dated Sep. 20, 2017, 6 pp.
Response to Examination Report dated Sep. 20, 2017, from counterpart European Application No. 11700870.6, filed Mar. 26, 2018, 14 pp.
Office Action from counterpart Canadian Application No. 3,058,773, dated Dec. 21, 2020, 5 pp.
Notice of Allowance from counterpart Canadian Application No. 2,786,297, dated Mar. 19, 2019, 1 pp.
Office Action from counterpart Canadian Application No. 3,058,773 dated May 30, 2022, 4 pp.

\* cited by examiner

ERYTHROPOIETIC STIMULATING AGENT (ESA) DOSAGE DETERMINATION

RELATED APPLICATION

This application is a continuation of U.S. application Ser. No. 13/519,843, filed Jan. 4, 2011, which is a 371 application of International Application No. PCT/US2011/020120, filed Jan. 4, 2011, which claims the benefit of U.S. Provisional Application No. 61/292,087, filed Jan. 4, 2010, the entire contents of each of which are incorporated herein by reference.

TECHNICAL FIELD

The disclosure relates to modeling of biophysical parameters to determine pharmaceutical dosages.

BACKGROUND

Anemia causes an increased sense of fatigue, decreased stamina and exercise tolerance, fatigue, shortness of breath, decreased appetite, and decreased CNS functioning. Anemia can lead to the need for red blood cell (RBC) transfusions, with associated risks including bacterial and viral infections, volume overload, iron overload, and a variety of transfusion reactions.

Chronic Kidney Disease (CKD) and End Stage Renal Disease (ESRD) patients are at risk for anemia since RBC homeostasis requires normal kidney function. The kidneys play a critical role in erythropoiesis. Erythropoietic Stimulating Agents (ESAs) are used among these patients as a pharmacological replacement for the hormone erythropoietin (EPO), produced primarily by healthy kidneys, and to a small extent by the liver (Hepatic EPO). Other patient populations, including cancer patients, may also experience reduced levels of hemoglobin and may benefit from ESA therapy.

Hemoglobin (Hgb) values are a primary indicator of anemia. The Centers for Medicare & Medicaid Services (CMS) and National Kidney Foundation (NKF) have established the target range for Hgb values among ESRD patients to be between 10 g/dL and 12 g/dL. Hgb values below the desired minimum lead to an increased sense of fatigue and decreased stamina and are considered to be a risk factor for increased cardiovascular morbidity and mortality in ESRD patients. Patients with Hgb values under 10 g/dL suffer from the effects of anemia, including fatigue and reduced stamina and exercise tolerance, shortness of breath, decreased appetite and decreased CNS functioning, and reduced compliance. Anemia can lead to the need for red blood cell (RBC) transfusions, with associated risks including bacterial and viral infections, volume overload, iron overload, and a variety of transfusion reactions.

Hgb values above 12.0 g/dL are believed to create an increased risk of cardiovascular events such as stroke and myocardial infarction, cerebrovascular and cardiovascular mortality and morbidity. Patients with Hgb values over 12 g/dL are at risk of thrombosis, vascular access clotting (compromising effective dialysis therapy), hypertension, and increased risk of acute coronary syndromes or cerebrovascular accidents. These observations have led to the development of regulatory and quality standards which lead practitioners to try and maintain the hemoglobin values of ESRD patients within the narrow range of 10.0-12.0 g/dL.

In ESRD patients, as well as in other patient populations experiencing reduced hemoglobin levels, the biophysical system that regulates erythropoietin production does not function properly. ESAs are often prescribed to manage hemoglobin levels (anemia) in ESRD patients and in other patient populations. An ESA prescription may include, for example, intravenous injection of darbepoetin alfa (Aranesp®) or Recombinant Human Erythropoietin (rHuEPO). The current protocol for developing ESA prescriptions produces patterns of hemoglobin (Hgb) oscillation that subject patients to a cycle of overshoot and undershoot of target Hgb values. For example, when the patient exhibits a low Hgb, the dosage may be dramatically increased in an attempt to quickly raise Hgb levels. When the patient exhibits a high Hgb, interruption of ESA therapy (by greatly reducing the dose or withholding administration) may lead to under-dosing of the ESA, which, in turn, leads to an undershoot of Hgb values. The result is an undesirable fluctuation of Hgb levels above and below the target range. The period of the High-Low-High may take up to nine months for a complete cycle. Hgb values are often measured monthly, rendering Hgb cycling practically imperceptible.

In addition to the effects of low or high Hgb values upon ESRD patients, there are considerable administrative and financial impacts upon a dialysis facility if Hgb values are not maintained within the desired range. For example, the current protocol requires an ESA prescription to be developed one time per month per patient. Due to the cyclic variation in both Hgb levels and ESA dosage, considerable personnel time is used to review and adjust ESA dosage.

The current protocol also cannot project future actual ESA requirements, leading to difficulties with ESA inventory management. As a result of this uncertainty, dialysis facilities will often maintain large ESA inventories. However, because ESAs are relatively expensive, maintenance of large unused ESA inventories may not be financially optimal. In addition, Medicare and/or other insurance providers may impose penalties when patient Hgb levels exceed 12.0 g/dL for varying periods of time. These denials may occur retrospectively; that is, after the ESA has already been administered and the cost has been incurred by the dialysis facility.

In addition, patient Hgb values are often monitored monthly by regulatory agencies. A systematic pattern of high Hgb values can cause sanctions to be applied, which may include the creation of monitored compliance plans or even closure of a dialysis facility until a plan to achieve compliance is approved.

SUMMARY

In general, the disclosure describes system(s) and/or method(s) for determining Erythropoietic Stimulating Agent (ESA) dosing.

In one example, the disclosure is directed to a method of treating anemia in a patient comprising receiving patient-specific historical hemoglobin (Hgb) data for the patient and corresponding patient-specific historical erythropoietic stimulating agent (ESA) dosage data for the patient, estimating patient-specific Hgb values in response to the patient-specific historical ESA dosage data for each of a plurality of sets of parameter values of a biophysical simulation model that represents a process by which red blood cells are produced in humans, selecting one of the plurality of sets of parameter values such that the estimated patient-specific Hgb values substantially fit the patient-specific historical Hgb data, simulating patient-specific Hgb values for a future prescriptive period of time based on the biophysical simulation engine, the selected set of parameter values, and a plurality of therapeutic ESA dosages, identifying at least one of the plurality of therapeutic ESA dosages that maintains the simulated patient-specific Hgb values within a target range during the future prescriptive period of time, and administering one of the identified therapeutic ESA dosages to the patient.

In some examples, estimating the patient-specific Hgb values for each of the plurality of sets of parameters comprises applying Monte Carlo methods to estimate the patient-specific Hgb values.

In some examples, the method further comprising identifying one or more commercially available dosing regimens that deliver the equivalent of the therapeutic dose.

In some examples, the plurality of parameters include one or more of a Blast Forming Unit Input, a Colony Forming Unit Survival, a Recticulocyte Survival, an Erythropoietin Receptor Multiplier, a Red Blood Cell Lifespan, and an Erythropoietin Setup Rate.

In some examples, the plurality of parameters includes an erythropoietin setup rate parameter having a patient-specific value that when applied to the biophysical simulation model raises the simulated patient-specific Hgb values to a level equal to the patient-specific historical Hgb data on a first day for which the simulation is performed.

In some examples, the ESA is one of erythropoietin, recombinant human erythropoietin, epoetin alpha, epoetin beta, darbepoetin alpha, and methoxy polyethylene glycol-epoetin beta.

In some examples, the biophysical simulation model includes taking into account delay in increase of simulated patient-specific Hgb values in response to delivery of the proposed therapeutic ESA dosages and delay in decrease of simulated patient-specific Hgb values due to lifespan of circulating red blood cells in the patient.

In some examples, the biophysical simulation model includes a patient-specific parameter corresponding to increased survival rate of erythroblast precursor cells in bone marrow of the patient in presence of an ESA.

In some examples, the biophysical simulation model includes a patient-specific parameter corresponding to increased survival rate of reticulocytes in bone marrow of the patient in presence of an ESA.

In some examples, the biophysical simulation model includes a patient-specific parameter corresponding to a lifespan of red blood cells in the patient.

In some examples, the patient has one of chronic kidney disease or end stage renal disease.

In some examples, the patient is a cancer therapy patient.

In some examples, the method further includes administering the identified therapeutic dose to the patient by any of intravenous (IV) delivery, subcutaneous delivery, oral delivery, biopump delivery, and an implantable device drug delivery.

In some examples, identifying at least one of the plurality of therapeutic ESA dosages that maintains the simulated patient-specific Hgb values within a target range during the future prescriptive period of time includes identifying one of the plurality of therapeutic ESA dosages that maintains the simulated patient-specific Hgb values at a target Hgb level during the future prescriptive period of time.

In another example, the disclosure is directed to a method of treating anemia in a patient, comprising receiving patient-specific historical hemoglobin (Hgb) and corresponding patient-specific historical erythropoietic stimulating agent (ESA) dosage data, estimating patient-specific values for each of a plurality of parameters of a biophysical simulation model that represents a process by which red blood cells are produced in humans based on the patient-specific historical Hgb and corresponding patient-specific historical ESA dosage data, wherein the biophysical simulation model includes a patient-specific parameter corresponding to increased survival rate of erythroblast precursor cells in bone marrow of the patient in presence of the ESA, wherein the biophysical simulation model includes a patient-specific parameter corresponding to increased survival rate of reticulocytes in bone marrow of the patient in presence of the ESA, wherein the biophysical simulation model includes a patient-specific parameter corresponding to a lifespan of red blood cells in the patient, determining at least one therapeutic ESA dosage that maintains a predicted patient-specific Hgb level within a target range based on the patient-specific values for each of the plurality of parameters, and administering one of the therapeutic ESA dosages to the patient.

In some examples, the ESA is one of erythropoietin, recombinant human erythropoietin, epoetin alpha, epoetin beta, darbepoetin alpha, and methoxy polyethylene glycol-epoetin beta.

In some examples, the biophysical simulation model includes taking into account delay in increase of simulated patient-specific Hgb values in response to delivery of the proposed therapeutic ESA dosages and delay in decrease of simulated patient-specific Hgb values due to lifespan of circulating red blood cells in the patient.

In some examples, the patient has one of chronic kidney disease or end stage renal disease.

In some examples, determining at least one therapeutic ESA dosage that maintains a predicted patient-specific Hgb level within a target range includes determining a therapeutic ESA dosage that maintains a predicted patient-specific Hgb level at a target Hgb level.

In another example, the disclosure is directed to a method of treating anemia in a patient, comprising receiving patient-specific historical hemoglobin (Hgb) data and corresponding patient-specific historical erythropoietic stimulating agent (ESA) dosage data obtained during a descriptive period of time, estimating patient-specific values for each of a plurality of parameters of a model that represents a process by which red blood cells are produced in humans based on the patient-specific historical Hgb data and the corresponding patient-specific historical ESA dosage data, simulating patient-specific Hgb values for a prescriptive period of time based on the estimated patient-specific parameter values, and identifying at least one therapeutic dose of the ESA that reduces Hgb cycling in the simulated patient-specific Hgb values and maintains the simulated patient-specific Hgb values in a target range during the prescriptive period of time; and administering the identified therapeutic dose of the ESA to the patient during the prescriptive period of time.

In some examples, the ESA is one of erythropoietin, recombinant human erythropoietin, epoetin alpha, epoetin beta, darbepoetin alpha, and methoxy polyethylene glycol-epoetin beta.

In some examples, the biophysical simulation model includes taking into account delay in increase of simulated patient-specific Hgb values in response to delivery of the proposed therapeutic ESA dosages and delay in decrease of simulated patient-specific Hgb values due to lifespan of circulating red blood cells in the patient.

In some examples, identifying at least one therapeutic dose of the ESA that reduces Hgb cycling in the simulated patient-specific Hgb values and maintains the simulated patient-specific Hgb values in a target range during the prescriptive period of time includes identifying at a therapeutic dose of the ESA that reduces Hgb cycling in the simulated patient-specific Hgb values and maintains the simulated patient-specific Hgb values at a target Hgb level during the prescriptive period of time.

The details of one or more examples are set forth in the accompanying drawings and the description below. Other features and advantages will be apparent from the description and drawings, and from the claims.

DETAILED DESCRIPTION

Figure 1:
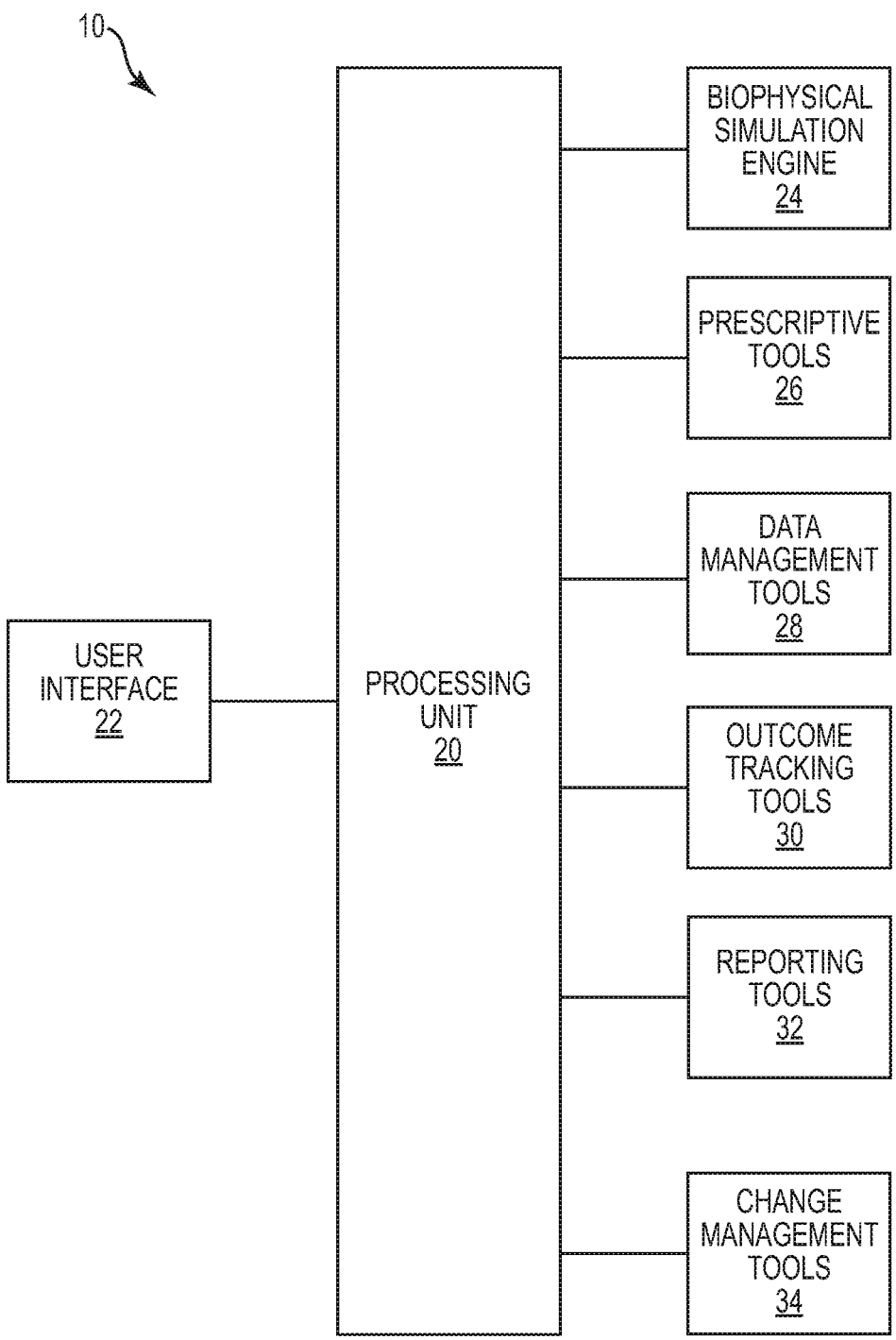
FIG. 1 is a block diagram illustrating an example system that determines a weekly therapeutic dose of an ESA that will result in stabilization of a patient's Hgb to a target level.

The disclosure generally relates to systems and/or methods that design patient-specific Erythropoietic Stimulating Agent (ESA) dosing regimens. The ESA dosing system and/or methods described herein may result in determination of patient-specific ESA dosing that achieves and sustains adequate Hgb values for patients receiving ESA therapy.

The ESA dosing techniques described herein may be used to determine patient-specific ESA dosing for any available ESA therapy. These ESAs may include, but are not limited to, Erythropoietin; Epoetin alpha (Procrit®, Epogen®, Eprex®); Epoetin beta; darbepoetin alpha (Aranesp®); Methoxy polyethylene glycol-epoetin beta; Dynepo; Shanpoeitin; Zyrop; Betapoietin; and others.

In addition, the ESA dosing techniques described herein may also be applicable to a wide variety of patient populations, including, for example, End Stage Renal Disease (ESRD) patients, Chronic Kidney Disease (CKD) patients, cancer therapy patients, or any other patient population having insufficient hemoglobin production that may benefit from ESA treatment such as anemia secondary to HIV infection. In addition, the ESA dosing techniques described herein may also be applicable to multiple modes of ESA therapy delivery, including intravenous (IV) delivery, subcutaneous delivery, oral delivery, biopump, implantable drug delivery devices, etc.

In recent years there has been much controversy regarding optimal Hgb target values in ESRD patients, as well as controversy over the impact of swings in Hgb values. Based on currently available clinical data, there is widespread agreement that the target value for Hgb should be somewhere between 10 and 12 grams/deciliter (g/dL), and that the probable desired optimal range is 11.0-12.0 g/dL. There is also growing agreement that stable Hgb values are more conducive to patient well-being than are wide oscillations in Hgb values. The system described herein enables care providers to identify dosing regimens that will establish and maintain Hgb values in the target range for the majority of their patients.

The system includes a patient-specific biophysical simulation model that, based on a patient's historical response to ESA therapies, determine a target dosing level which can be translated to a dosing regimen titrated to available commercial doses. The dosing regimen thus obtained can be configured to simultaneously achieve and sustain adequate and stable Hgb values for extended periods of time as well as minimize or eliminate Hgb oscillations (commonly known as Hgb cycling). The total amount (and cost) of ESA administered may also be reduced or minimized. If the patient's overall medical condition remains stable, Hgb values have been shown, using the techniques described herein, to remain stable at a given target level. If the patient's underlying medical condition changes, the system includes a diagnostic system which can be used to establish a new target dosing level that may restore Hgb values to a desired target level in a minimum of time.

In some examples, the system/method creates a recommended intravenous (IV) ESA dosing regimen including a dose level and dose administration frequency. Care providers can tailor the frequency of ESA administration enabling effective and efficient use of supporting staff time.

FIG. 1 is a block diagram illustrating an example system 10 that determines a weekly therapeutic dose of an ESA that will result in stabilization of a patient's Hgb to a target level. System 10 includes a processing unit 20 and an assortment of data processing and management tools. For example, system 10 includes a biophysical simulation engine 24 that predicts red blood cell (RBC) production (Hgb is contained within RBCs, so RBC production and hemoglobin production are used interchangeably in this document), ESA prescriptive tools 26, patient data management tools 28, outcome tracking tools 30, reporting tools 32, and change management tools 34 to maintain adequate and stable Hgb values through adjustments to the indicated therapy. A user interface 22 permits one or more users to input patient historical data (either manually or electronically), run the tools and view and manipulate the results.

The purpose of system 10 is to help care providers develop ESA dosing strategies that avoid creating the oscillations in Hgb values for patients that are characteristically created by existing protocols, and that provide stabilized Hgb levels within a target Hgb range.

Patients with ESRD have a deficiency of the hormone erythropoietin (the endogenous ESA), and, as a result, they are severely anemic. Anemia (hemoglobin <10.0 g/dL) is a risk factor for mortality in ESRD patients, and patients with anemia have poorer quality of life than non-anemic patients. Patients receiving an ESA also have an increased risk of cardiovascular events (stroke, myocardial infarction) if their hemoglobin rises above 12.0 g/dL. These observations have led to the development of regulatory and quality standards which lead practitioners to try and maintain the hemoglobin values of ESRD patients within the range of 10.0-12.0 g/dL. In addition, other patient populations may also receive ESA therapy, including CKD patients, cancer therapy patients, and other patients who would benefit from ESA therapy, and it shall be understood that ESA dosing system 10 may also be applicable to these and other patient populations. Thus, although some portions of this description may refer specifically to ESRD or CKD patients, it shall be understood that ESA dosing system 10 and the techniques implemented therein may also be applicable to other patient populations.

Patient-specific responses to ESA therapy are dependent upon a variety of factors, including total body iron storage status, extracellular volume fluid status, inflammation, residual kidney function, hemorrhage, and variations in the dose effectiveness of ESA among ESRD patients.

The majority of ESRD patients who need ESA therapy are currently receiving one of two formulations: rHuEPO, FDA approved for the treatment of anemia in patients with chronic renal failure in 1985, or darbepoetin alfa (Aranesp®), FDA approved in 2001. rHuEPO has an average half life of five to seven hours, requiring frequent administration. darbepoetin alfa was designed to have a longer half-life of 25-27 hours. The example simulation engine was designed to monitor patient response to darbepoetin alfa. However, adjustments to the simulation engine may allow for similar simulations to be conducted for patients receiving o rHuEPO, in transition from rHuEPO to darbepoetin alfa, or other ESA therapies.

Due its longer half life, darbepoetin alfa requires approximately five days for complete elimination. This allows providers to administer the drug less frequently. But the extended half-life of darbepoetin alfa, in combination with red blood cell dynamics, contributes to a confounding physiological consequence. After an administration of darbepoetin alfa, RBC production is enhanced for up to 26 days. This delay, if not factored into the design of the prescription, sets up Hgb oscillation. It is not uncommon for patients to experience 12-18 months of Hgb "overshoot" and "undershoot" as providers try to reestablish an adequate and stable Hgb level following existing protocols.

Figure 2:
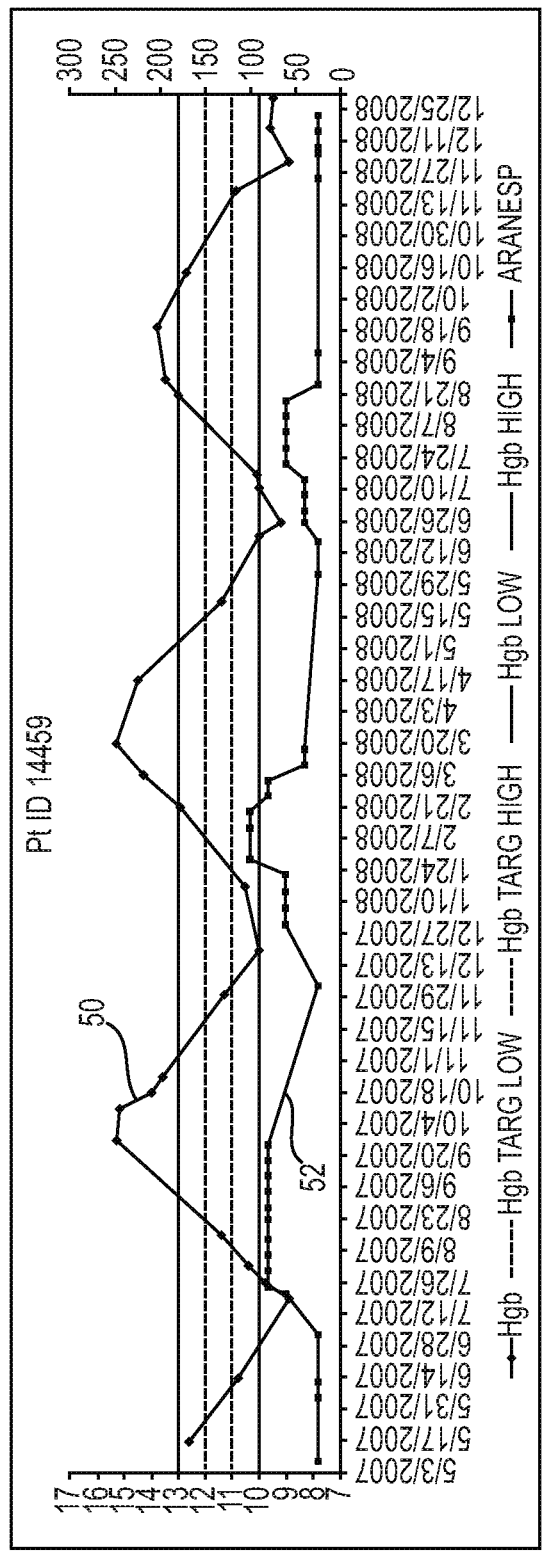
FIG. 2 is a chart of historical Hgb levels and ESA dosage over time for a patient under the existing ESA dosage protocol.

FIG. 2 is a graph illustrating an example of an actual oscillating Hgb pattern for an ESRD patient that was generated by following existing ESA protocol for the period May 2007 through December 2008. FIG. 2 illustrates a delayed response between ESA dosage (represented by curve 52) and the measured Hgb value (represented by curve 50). The delayed response makes it difficult to identify the appropriate dose when the provider considers only the most recent Hgb values. In addition, as mentioned above, response to ESA therapy is highly patient specific and cannot be generalized to a larger population. This case is a typical pattern observed among ESRD patients on dialysis receiving darbepoetin alfa.

The system uses an operational approach that includes all the factors that generate patient Hgb values. The system and associated processes and models described herein may help providers design ESA therapies that eliminate Hgb oscillations and achieve adequate and stable Hgb values within target levels.

Figure 3:
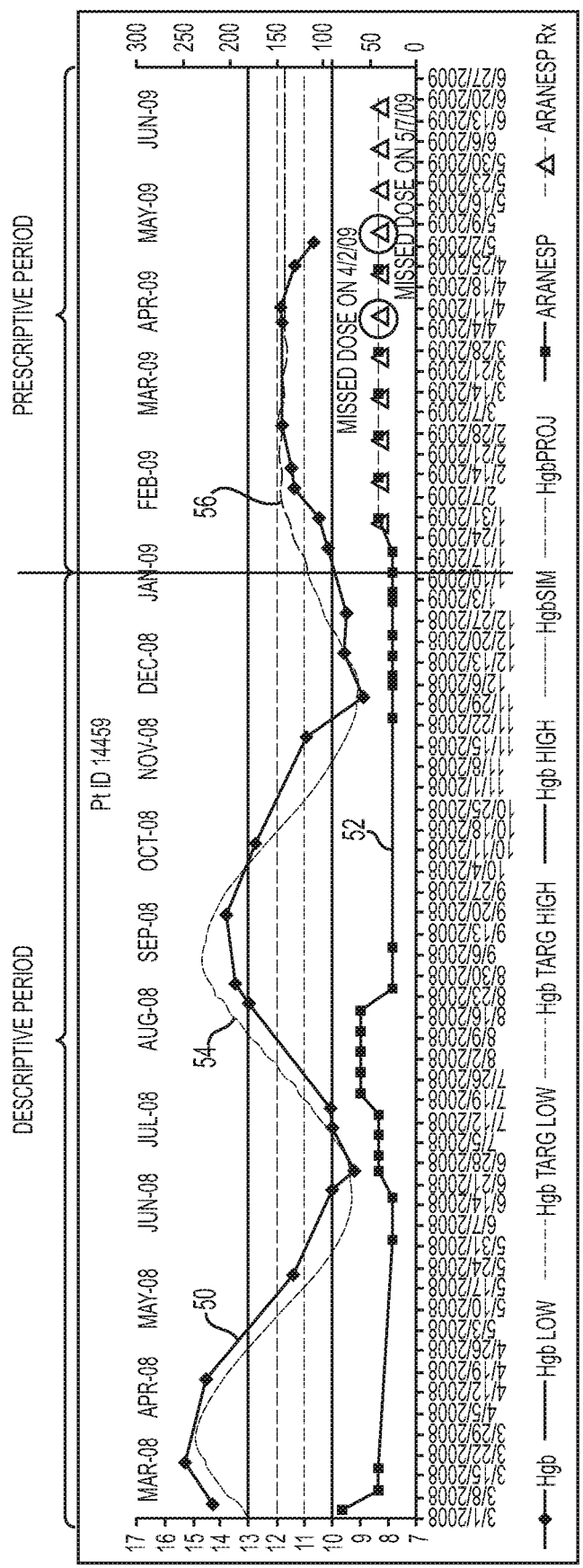
FIG. 3 is a chart of Hgb levels and ESA dosage over time for the patient in FIG. 2 under the weekly therapeutic dosage.

FIG. 3 is a chart of Hgb levels and ESA dosage over time for the ESRD patient of FIG. 2 both during a "descriptive period" and a "prescriptive period." In FIG. 3, the period between Mar. 1, 2008 and Jan. 11, 2009 is defined as the "descriptive period." The descriptive period includes historical data for a specific ESRD patient that includes monitored actual Hgb levels (curve 50) and ESA dosage over time (curve 52). The data collected during the descriptive period is used in a biophysical simulation that calculates the values for seven (in this example) patient-specific parameters that define an ESRD patient's response to ESA therapy. The biophysical simulation calculates these patient-specific parameters such that simulated descriptive Hgb values (represented by curve 54) match historical actual Hgb values during the descriptive period with a specified error. The patient-specific parameter values are then used as the basis for an ESA prescription for a "prescriptive period." The prescriptive period is the chosen time period for a simulation during which a recommended prescription (the therapeutic dose, which may be a per session therapeutic dose or a weekly therapeutic dose (WTD) depending, among other things, upon the particular ESA to be prescribed) will be designed, with the intent of determining a dosing regimen that will stabilize Hgb values within a target range. In this example, the prescriptive period is January 2009 through June 2009. FIG. 3 illustrates simulated prescriptive Hgb values (represented by curve 56) obtained using an optimized ESA dosage for the patient of FIG. 2. FIG. 3 illustrates that the optimized ESA dosage created an adequate and stable Hgb level for the prescriptive period within the target range.

Due to its longer half life, darbepoetin alfa requires approximately five days for complete elimination from the serum, and has a prolonged period of pharmacological activity. This allows providers to administer the drug less frequently. But the extended half-life of darbepoetin alfa, in combination with red blood cell dynamics, creates a physiological consequence. After an administration of darbepoetin alfa, RBC production is enhanced for up to 26 days. This delay, if not factored into the design of the prescription, sets up Hgb cycling. It is not uncommon for patients to experience 12-18 months of Hgb "overshoot" and "undershoot" as providers try to establish an adequate and stable Hgb level following existing protocols. The system accounts for feedback and delay in the erythropoietic process by establishing a target dosing level, assisting with the design of a dosing regimen, and monitoring results over time.

In current practice it is often desirable to reduce the frequency of administration in order to capture reduced administrative costs. When a patient is switched from bi-weekly to monthly dosing, for example, current practice is to double the dose and then seek the optimal regimen using current protocols. This introduces a potential round of Hgb cycling. However, it has been found using the presently described biosimulation techniques that reducing the frequency of administration by a factor of two requires far more than twice the previous dose. If such a decrease in frequency is otherwise desirable, the system permits the identification of the required dose to sustain adequate Hgb values. In other examples, the system may determine that increasing the frequency of administration with optimal doses may, in spite of increased administrative costs, reduce total cost due to significantly reduced amount of the drug required.

The presently described biosimulation techniques utilize dynamic modeling. Dynamic modeling is a framework, consisting of a language and a set of concepts. These are embedded in a process for representing, understanding, explaining and improving how dynamic systems (erythropoiesis, for example) work, how they perform over time, and how they respond to inputs (such as ESA administration).

There are several commercial packages available to build and simulate dynamic models, including iThink®, available from Isee Systems, Inc.; Stella®, available from Isee Systems, Inc.; Vensim®, available from Ventana Systems, Inc.; Powersim Studio 8, available from Powersim Software AS; Berkeley Madonna™, developed by Robert Macey and George Oster of the University of California at Berkeley; and other commercially available software packages. The example described herein was implemented using iThink version 9.3 and the examples provided herein are described using iThink syntax and conventions. It shall be understood, however, that the specific implementation described herein is one example of how the biosimulation model may be implemented, and that equivalent models may be constructed in each of the aforementioned commercial packages, in other commercially available packages, in customized software packages, or in application specific software programs and/or systems, and that the disclosure is not limited in this respect.

The model manages the dynamic linkage that exists between the pharmacokinetics and pharmacodynamics of the ESA in question with the dynamics of the RBC chain. Further, the model may be embedded in a data processing system that enables effective ESRD anemia management both at the individual and group level.

Figure 4:
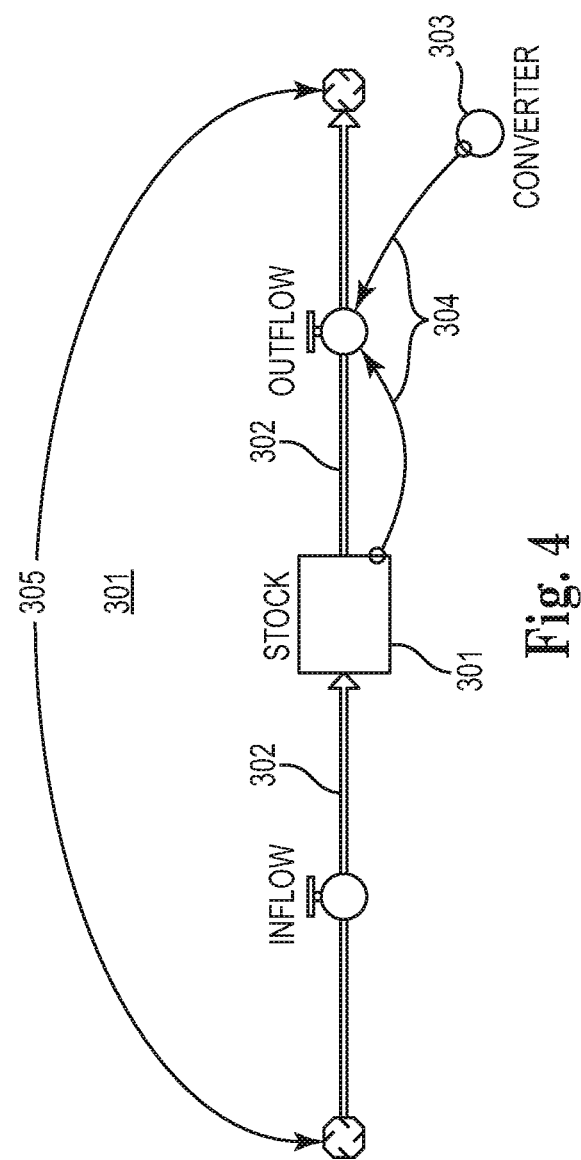
FIG. 4 is a diagram illustrating four example building blocks of a commercially available dynamic modeling application.

FIG. 4 shows the four elements of the syntax used in the selected commercial package (iThink, in this example). A Stock (301) represents an accumulation at a point in time, such as total RBC count. A Flow (302) represents rates of flow over time. FIG. 4 contains two flows, an inflow and an outflow, such as RBC's created per day and RBC's destroyed per day, respectively. The values of stocks and flows are evaluated at each point in time in a simulation using user-supplied mathematical expressions. A Converter (303) represents and contains a mathematical expression that may be as simple as a constant value or as complex as an aggregate of a generalized subsystem. Connectors (304) indicate relationships between variables in the model, both graphically and mathematically. Cloud icons (305) represent boundaries of the model. When all the required mathematical relationships with a model's design are described, the behavior of the modeled system may be simulated for a period of time. This simulation is performed by calculating the current state of the system from the beginning of the simulation time period to the end, stepwise and incrementally, using a selected time increment, delta t, referred to as DT. By observing the dynamic behavior of various variables (RBC counts and Hgb values, for example) model users are able to confirm or refine their understanding of how erythropoiesis operates and create successive model improvements until the simulated behavior effectively matches known data.

Figure 5:
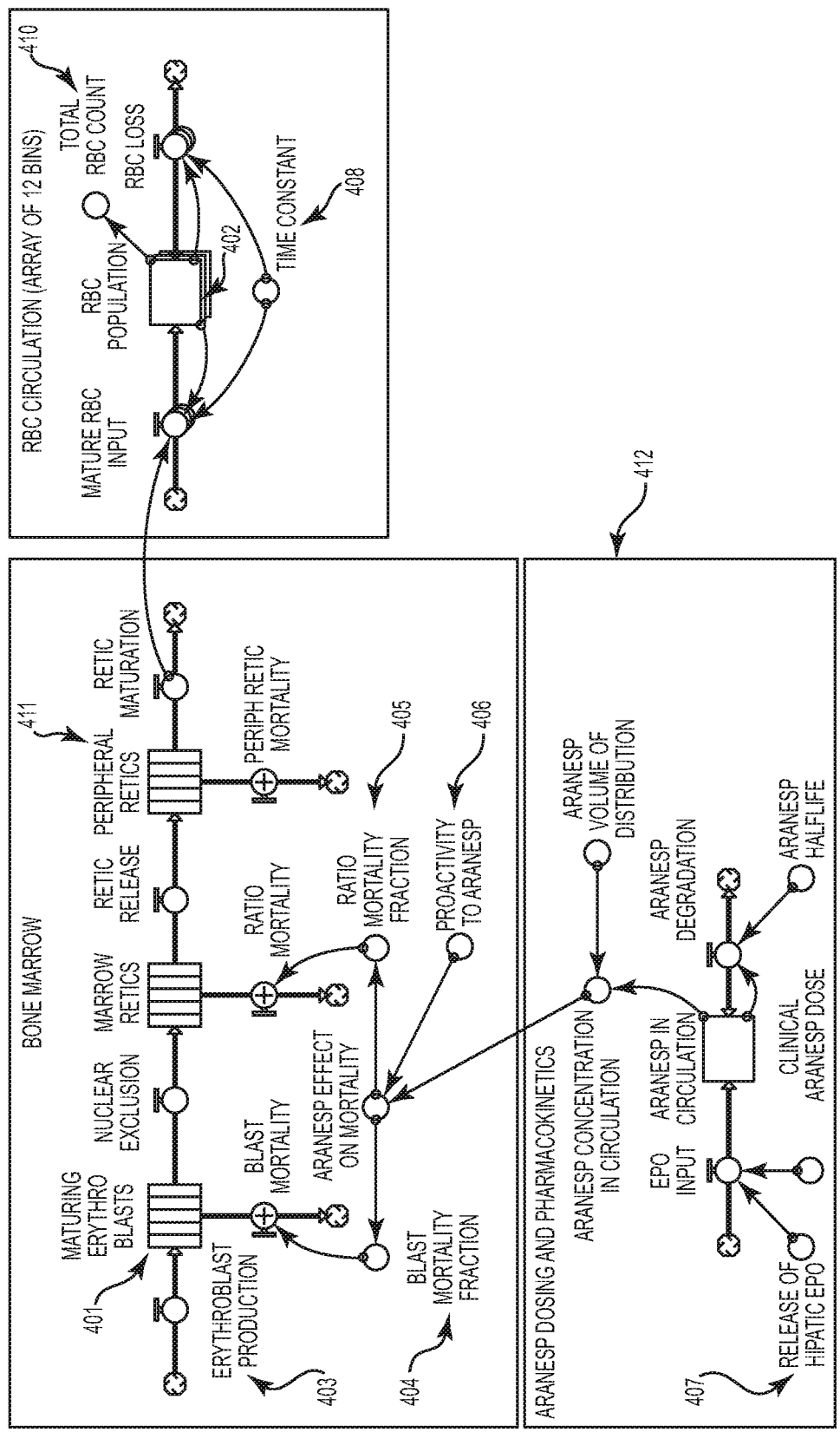
FIG. 5 is a diagram illustrating the core model of the biophysical simulation engine.

FIG. 5 is a diagram illustrating an example of a biophysical simulation model. The model simulates the relationship between the concentration of darbepoetin alfa and Hgb values for individual patients over time. In other examples, the model may simulate the relationship between the concentration of other ESAs and Hgb values.

Figure 6:
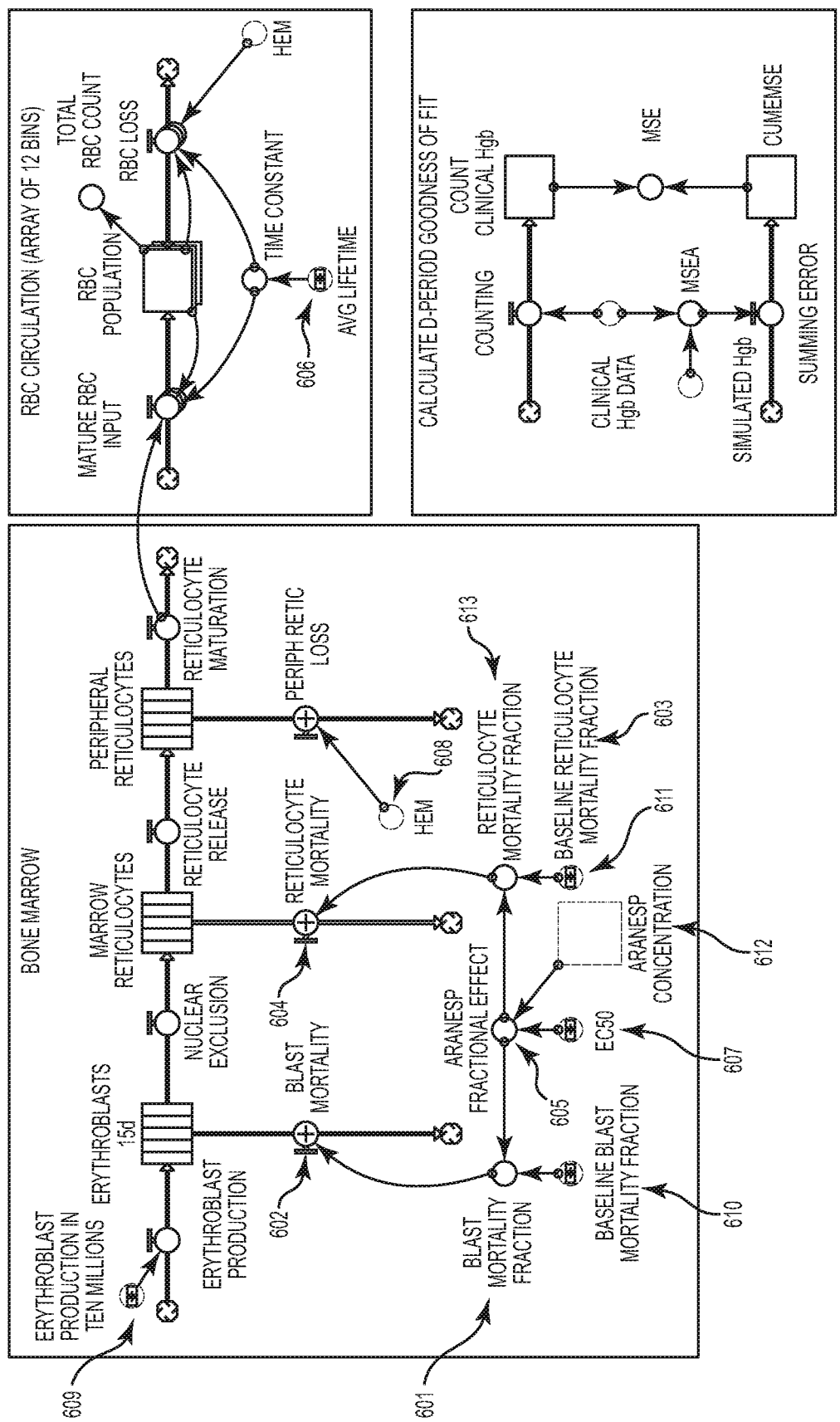
FIG. 6 is a diagram illustrating the configuration of five of seven parameters used in the biophysical simulation engine.

FIG. 6 is a diagram illustrating the configuration of five of seven parameters used in the biophysical simulation model: erythroblast production in ten millions (609), baseline blast mortality fraction (610), baseline reticulocyte mortality fraction (611), EC50 (607), and avg lifetime (606). Note that FIG. 6, concerning the baseline blast mortality fraction (610), provides a more detailed description than FIG. 5 provides in the description of blast mortality fraction (404). On the other hand, in FIG. 6, the icon Aranesp Concentration (612), represents all of the detail shown in FIG. 5, Aranesp Dosing and Pharmacokinetics (412). The purpose of FIG. 6 is to illustrate the configurations of the five parameters listed above in this example of the biophysical simulation model.

The process of constructing the example model was to consult with subject matter experts to learn how selected variables are related and then to translate those relationships to a specific model in the chosen syntax. Various decisions are made in the model building process concerning levels of aggregation/disaggregation required to achieve the model's purpose. In other examples, levels of aggregation/disaggregation may be modified to achieve the same purpose, while exposing differing biophysical behaviors over time.

The model building process includes decisions about boundaries of the model that are consistent with the model purpose. This is referred to as establishing the extensity of the model. Other examples of the model may include revisions to the model's extensity as described below.

The specific example of the model described with respect to FIG. 5 includes the following boundaries: dynamics of progenitor cells in the marrow are excluded; the impact of eliminated RBC's is excluded; tissue oxygenation is excluded; iron metabolism is excluded; the model is aimed at simulating Hgb response profiles of iron replete patients; and plasma fluids are excluded. However, it shall be understood that in other examples of the model, such as the model shown and described with respect to FIGS. 20-35, one or more of these factors could be taken into account. For example, other examples of the model could include plasma fluids and simulation of Hematocrit values, a measure often used instead of Hgb values. Any or all of these boundaries, or related boundaries, may be included while maintaining the fundamental purpose of simulating an individual patient's response to ESA therapy. In addition, the model may also include simulation of Hgb response profiles in patients that are not iron replete.

Typically in scientific studies of the factors that relate to a so-called dependent variable, one performs various studies of correlation, analysis of variance, principal components, etc. Parameters of a Dynamic Model, however, are identified and used differently than in statistical studies. Once the boundary of a dynamic model is defined, the parameters describe exogenous inputs to the model. The parameters of a dynamic model describe operational variables (as, in general, do endogenous model variables as well) in that they describe causal factors of the behavior being simulated. As an example, the parameter Erythroblast Production Rate (EPR) is one parameter to the biosimulation model. This parameter describes the rate at which erythroblasts are created per day. The value of this parameter is not merely correlated to the RBC count, but, all other parameters equal, a given value for EPR will cause a certain number of RBC's to exist. Note that parameters may be constants or complex mathematical expressions, representing aggregates of external subsystems. Note that parameters selected and defined for a dynamic model depend upon the definition of the model's boundary.

The system develops a targeted dosing plan, and then anticipates changes in the patient's response to the ESA therapy, which allows for an equally targeted response that reduces or avoids Hgb oscillations. The result may be that more ESA therapy patients have hemoglobin values maintained within the desired range of 10.0-12.0 g/dL, or within 11.0-12.0 g/dL.

The modeling process takes into account not only endogenous physiological factors that regulate red blood cell (hemoglobin) values, but also the patient in order to achieve and maintain an adequate, stable Hgb level. This model is unique for each individual patient, and this allows for inclusion of patient-specific components of anemia management.

Table 1 lists the seven patient-specific parameters utilized in this example, provides a definition of each, and sets forth example default minimums and maximums used in this example of the model. Alternative examples may use a different parameter set, yet still describe the dynamics of Hgb response to various dosing regimens.

TABLE 1

| Name | Description | Default Minimum Search Value | Default Maximum Search Value |
|---|---|---|---|
| Erythroblast Production Rate | The rate at which patient produces erythroblasts per day ($\times 10^6$) | 60 | 90 |
| Blast Mortality Fraction | Daily mortality of erythroblasts | 60% | 90% |
| Reticulocyte Mortality Fraction | Daily mortality of reticulocytes | 40% | 60% |
| Hepatic EPO | Endogenous erythropoietin created by the liver. Assumed to be zero for most ESRD patients, but may be a factor for some. May also be used to model Endogenous EPO produced through residual kidney function. | 0 | 0 |
| RBC Avg Lifespan | Average number of days for patient's RBC's. | 50 | 100 |
| EC50 | Represents a patient's resistance to ESA therapy A measure of patient sensitivity to EPO therapy. High EPO resistance indicates low sensitivity to therapy. | 15 | 25 |
| Setup EPO | A mathematical construct used to initialize the simulation model for "day 1" of the simulation. A mathematical EPO dose applied to a simulation model during model initialization for the purpose of stabilizing simulated Hgb to the value of the first historical Hgb in the patient's descriptive period. | 1 | 5 |

The Erythroblast Production Rate (EPR) represents the number of erythroblasts created per day within the bone marrow, but outside the boundary of this example of the model. FIG. 5 shows that EPR (403) is an inflow to the conveyor that accumulates maturing erythroblasts (401). In this example, the value of EPR is held fixed. Alternative examples may include time varying values for EPR. Still other examples may subsume the parameter, rendering it an endogenous model variable that may be a constant, a complex mathematical expression or a variable that is dependent on other model variables or parameters. These comments concerning alternative examples of the model apply equally well to each of the parameters described below. Typical ranges for EPR values were obtained, for example, from subject matter experts in hematology.

The leakage flow named blast mortality (602 in FIG. 6) represents the fraction of maturing erythroblasts that go through programmed cell death each day. Typical ranges for this fraction, as well as for the other parameters described below, were obtained from subject matter experts in hematology. A common misconception in the art is that ESAs enhance the creation of erythroblasts in the marrow, or as in FIG. 6, erythroblast production in ten millions (609). Although ESAs do stimulate erythroblast production, the Applicants have identified that a relatively more significant effect of ESAs is to inhibit blast mortality (602) (as well as other factors described below) which allows a larger fraction of maturing erythroblasts to survive, thus creating more RBCs, all other factors being equal. In this example of the model, darbepoetin alfa stimulates RBC production by increasing the survival rate of precursor cells. FIG. 6 shows specifically how this example of the model operates in this regard. The exposed detail FIG. 6 provides (relative to FIG. 5) the baseline blast mortality fraction (610) as the actual model parameter. Blast Mortality Fraction (601) is a value that is determined by the value of baseline blast mortality fraction (610) as moderated by the variable Aranesp fractional effect (605). In an alternative example of the model, Aranesp fractional effect (605) may be named (and appropriately mathematically revised) ESA fractional effect, thus representing different types of ESAs that operate in the same manner.

The Reticulocyte Mortality Fraction (RMF) is similar in effect to the BMF. In this example of the model, darbepoetin alfa stimulates RBC production by increasing the survival rate of reticulocytes in the marrow. FIG. 6 shows specifically how this aspect of the example model operates. The parameter is more correctly named the Baseline Reticulocyte Mortality Fraction (603). The RMF (604) is determined by the combination of the Baseline Reticulocyte Mortality Fraction (603) as moderated by the variable named Aranesp Fractional Effect (605), which in alternative examples of the model may be named ESA Fractional Effect, thus applying to different types of ESAs that operate in the same manner. Note that in this example of the model, the variable Aranesp Fractional Effect (605) is the same for both BMF and RMF. In other examples, different values for Aranesp Fractional Effect relative the BMF and RMF may be used.

Figure 7:
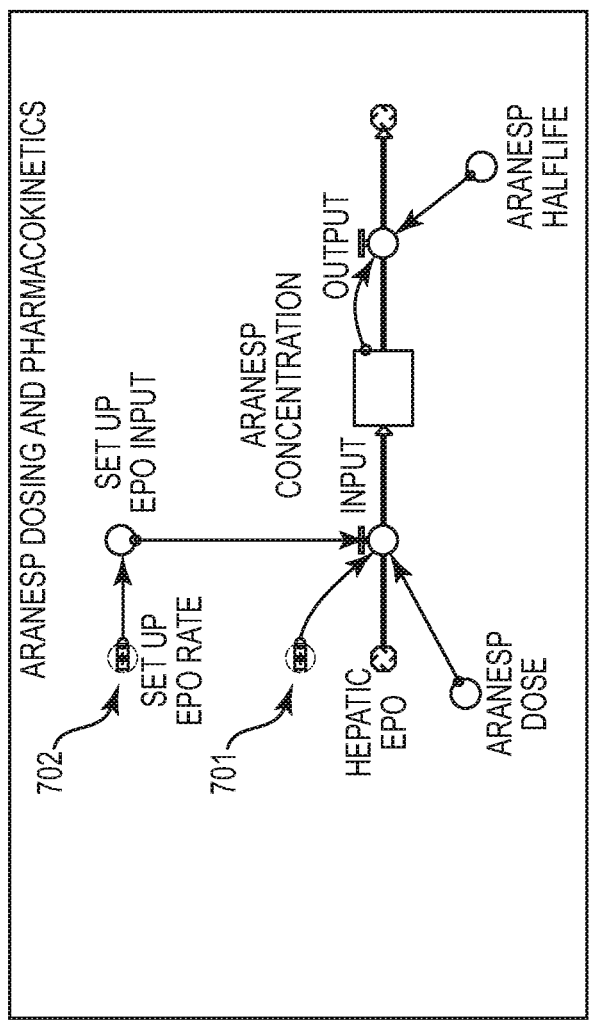
FIG. 7 is a diagram illustrating the configuration of two of seven parameters used in the biophysical simulation model: hepatic EPO and setup EPO rate.

Hepatic EPO is shown in FIG. 7 (701). Hepatic EPO is a form of endogenous epoetin produced by the liver. As explained below, the parameter Hepatic EPO is one of several inputs to the serum concentration of the ESAs. Originally envisioned as an exogenous model parameter, experience with this example of the model has confirmed what is clear from medical literature: the impact of Hepatic EPO is insignificant relative to the impact of administered darbepoetin alfa. In this example, therefore, the Hepatic EPO parameter is uniformly fixed to zero. Other examples of the model may include non-zero values for Hepatic EPO.

RBC Average Lifespan is included as a parameter for this example of the model. It is known that, while in healthy individuals, the RBC Lifespan is about 120 days, for ESRD patients on dialysis, the RBC Lifespan is shorter in duration. RBC Average Lifespan is named Average Lifetime (606) in FIG. 6. Alternative examples of the model may represent the lifespan of RBC's differently, allowing various RBC mortality rates for RBC's of different vintages.

In practice, the EC50 of an agent is the concentration that produces a response half way between the baseline and maximum response for a given time period. Usually a measure of potency, this parameter is used differently in this example of the model as a measure of what is known in the field as EPO resistance. Various medical conditions such as inflammation, infection, and the presence of ESA antibodies can decrease an individual patient's response the ESA therapy. This example of the model uses a single measure of EPO resistance. Alternative examples may use separate values for each cause of EPO resistance which could potentially produce an improved simulation. FIG. 6 (bone marrow) shows how EC50 (607) is configured in the model. The mathematical expression used to evaluate the Aranesp Fractional Effect (605) includes factors related to EC50 (607).

As explained above, the RBC chain is represented in this example of the model as an array of 12 so-called bins of RBC cells. In the initial phase of a simulation, named the Setup Phase, a steady state RBC count is established in each of the 12 bins, corresponding to the initial actual Hgb value for an individual patient in the second, Descriptive Phase of the simulation. (The Descriptive Phase is described below.) To establish a steady state RBC count, this example of the model is provided with what is mathematically equivalent to an externally administered dose. FIG. 6 shows how the parameter setup EPO rate (702) is configured in this example of the model to achieve this result. As described below, setup EPO rate (702) is in effect during the Setup Phase of a simulation; its value diminishes to zero during the subsequent Descriptive and Prescriptive Phases of a simulation.

Figure 8:
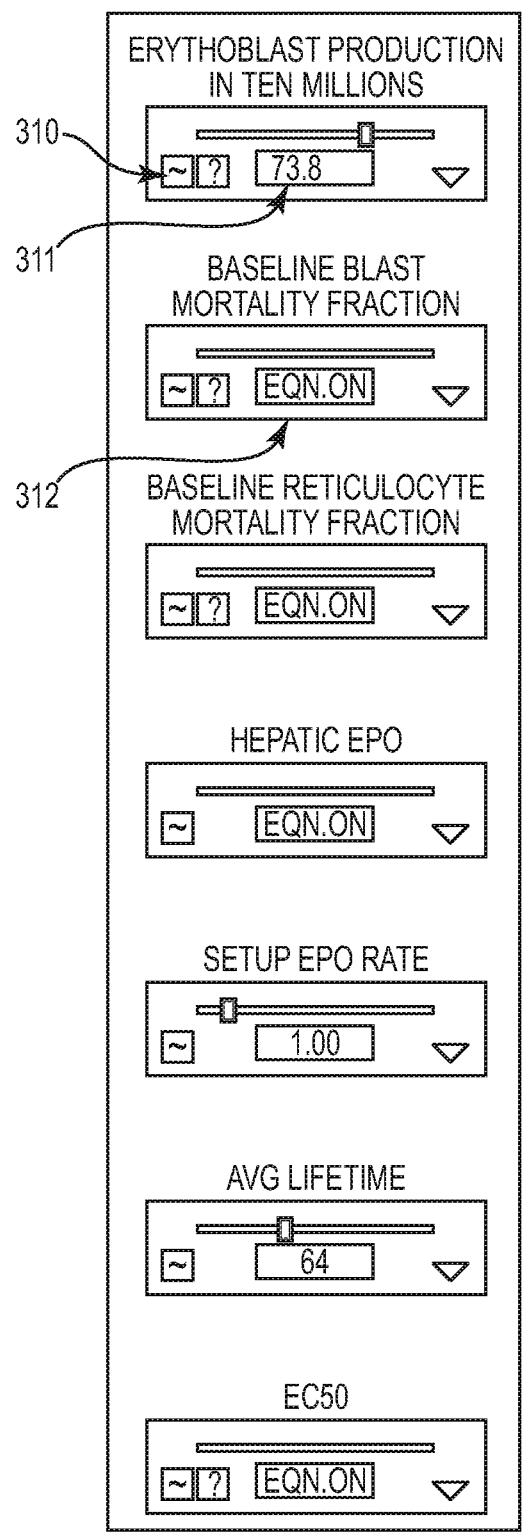
FIG. 8 is a diagram containing a screenshot of a portion of the biophysical simulation model user interface that controls the use of model parameters.

The user of the model, or the software system into which the model is integrated, develops an initial estimate of patient-specific parameter values, as described below. Initial estimates of parameter values may be manually adjusted using the interface to the biophysical simulation engine. FIG. 8 depicts that part of the user interface which enables manual manipulation of parameter values in this example. The interface is constructed so that a given simulation may use either initial estimates or manually revised estimates of parameter values. In FIG. 8, the tilde (310) is in the off position, indicating that the value 73.8 (311) is to be applied in the simulation as a substitute for the initial parameter value estimate. The expression "eqn on" (312), indicates that the initial estimate is to be used for the corresponding parameter value.

A dynamic model, as expressed using the selected commercially available simulation package or any of the others listed above, is defined by its degree of aggregation among selected variables, model boundaries, exogenous parameter values, time period to be simulated, and time increment (DT) to use for the simulation. A model so expressed simulates proposed causal relationships among its elements, as distinct from correlated relationships. As such, a model so defined represents a theory of dynamic behavior of a system that can be tested in a laboratory, confirmed, and refined. The dynamic modeling process often includes simulation and testing of a proposed dynamic hypothesis using a specific model, testing and validation of the dynamic hypothesis, followed by revisions to any of the model elements to improve model performance. Dynamic modeling is an iterative process in which the dynamics of the system are represented, understood, and explained in order to improve the simulation of the dynamic system under study, in this case erythropoiesis for iron replete ESRD patients on dialysis receiving darbepoetin alfa. The scope of the claims presented below shall include all the iterates of the example models described herein and those which may evolve in future examples.

Referring again to the example core model shown in FIG. 5, elements of the model as a whole that are not part of the core model are generally elements that inform, control, and report on values of elements that are within the core model. The core model, when supplied with appropriate patient specific parameter values and a dosing regimen (409) simulates an individual patient's response in terms of Total RBC Count (410). Total RBC count is then converted to a Hgb value. In an alternative example of the model, the contribution of peripheral reticulocytes (411) may be included in the calculation of Hgb values. Extension of the model boundary to include plasma fluids may enable reporting on hematocrit values in addition to Hgb.

FIG. 5 contains two syntax items not previously described, namely Conveyors (401, for example) and a Stock Array (402). Conveyors are specialized stocks that have an inflow and up to two outflows. Conveyors follow a First in First Out Rule in which quantities that flow in to the conveyor exit the conveyor in the same order as they entered, after a specified conveyor transit time. The outflow and contents of a conveyor can also be modified by a second optional outflow, named a Leakage flow. The rate of flow through a leakage flow is specified as a fraction of the inflow at each time increment of DT. A Stock Array (402), as implemented in this example, is a sequence of 12 stocks in which the outflow of the first stock in the sequence is the inflow to the second, and so on. The Core Model in FIG. 5 represents RBC's as twelve sequential stocks. The first stock in the array represents RBC's that are one day old to a value equal to the Time Constant (408) divided by 12. Successive stocks in the array represent RBC's at correspondingly older vintages, as determined by the time constant (408).

Table 2 lists the correspondence between the seven patient-specific parameters listed in Table 1 and the variables shown in FIG. 5.

TABLE 2

| Name | Description | Generalized Variable Name in Core Model |
| --- | --- | --- |
| Erythroblast Production Rate | The rate at which patient produces erythroblasts per day ($\times 10^6$) | Erythroblast Production |
| Blast Mortality Fraction | Daily mortality of erythroblasts | Blast Mortality Fraction |
| Reticulocyte Mortality | Daily mortality of reticulocytes | Retic Mortality Fraction |

TABLE 2-continued

| Name | Description | Generalized Variable Name in Core Model |
| --- | --- | --- |
| Fraction Hepatic EPO | Endogenous erythropoietin created by the liver. Assumed to be zero for most ESRD patients, but may be a factor for some. May also be used to model Endogenous EPO produced through residual kidney function. | Release of Hepatic EPO |
| RBC Avg Lifespan | Average lifespan of a patient's RBC's (number of days). | Time Constant |
| EC50 | Represents a patient's resistance to ESA therapy. A measure of patient sensitivity to EPO therapy. High EPO resistance indicates low sensitivity to therapy. | Sensitivity to Aranesp |
| Setup EPO | A mathematical construct used to initialize the simulation model for "day 1" of the simulation. A mathematical EPO dose applied to a simulation model during model initialization for the purpose of stabilizing simulated Hgb to the value of the first historical Hgb in the patient's descriptive period. | Setup EPO rate |

The following are illustrative equations for the example model shown in FIGS. 5-7, as expressed in the syntax of a commercially available modeling application (iThink®, available from Isee Systems, Inc., in this example). The equations describe the relationships between model variables for a specific patient. Also shown are definitions for core model variables, some of which are not shown in FIG. 5. Although an example implementation using iThink® is shown, it shall be understood that the ESA dosing techniques described herein may also be implemented using other commercially available or customized software applications.

```
Aranesp_in_circulation(t) = Aranesp_in_circulation(t - dt) + (EPO_input - Aranesp_degradation) * dt
   INIT Aranesp_in_circulation = 1
   DOCUMENT: Aranesp concentration at time t.
   INFLOWS:
      EPO_input = setup_EPO_input + hepatic_EPO + ( IF time < DOSE_A_START

THEN CLINICAL_ARANESP_DOSE

ELSE Aranesp_Pulse

)
         DOCUMENT: The IV dose to be administered, either in the descriptive period when parameters are being sought, or in the
         prescriptive period when either the weekly therapeutic dose or a proposed dose is being proposed.
   OUTFLOWS:
      Aranesp_degradation = Aranesp_in_circulation*Aranesp_halflife
         DOCUMENT: Elimination of the drug at time t.
marrow_retics(t) = marrow_retics(t - dt) + (nuclear_exclusion - retic_mortality - retic_release) * dt
   INIT marrow_retics = 7e8
   TRANSIT TIME = 2
   INFLOW LIMIT = INF
   CAPACITY = INF
   DOCUMENT: Count of marrow reticulocytes at time t.
   INFLOWS:
      nuclear_exclusion = CONVEYOR OUTFLOW
         DOCUMENT: Rate of surviving erythroblasts at time t.
   OUTFLOWS:
```

```
    ◇ retic_mortality = LEAKAGE OUTFLOW
        LEAKAGE FRACTION = retic_mortality_fraction
        NO-LEAK ZONE = 0
        DOCUMENT: Rate of reticulocytes mortality at time t.
    ◇ retic_release = CONVEYOR OUTFLOW
        DOCUMENT: Rate of surviving marrow reticulocytes at time t.
▦ maturing_erythro_blasts(t) = maturing_erythro_blasts(t - dt) + (erythroblast_production - nuclear_exclusion - blast_mortality) * dt
    INIT maturing_erythro_blasts = 6e9
    TRANSIT TIME = 15
    INFLOW LIMIT = INF
    CAPACITY = INF
    DOCUMENT: Count of erythroblast cells at time t.
    INFLOWS:
    ◇ erythroblast_production = erythroblast_production_in_ten_millions * 1e7
        DOCUMENT: A main model parameter, estimating overall erythroblast production rate for the duration of the simulation. This value is found using the partial monte carlo simulation.
    OUTFLOWS:
    ◇ nuclear_exclusion = CONVEYOR OUTFLOW
        DOCUMENT: Rate of surviving erythroblasts at time t.
    ◇ blast_mortality = LEAKAGE OUTFLOW
        LEAKAGE FRACTION = blast_mortality_fraction
        NO-LEAK ZONE = 0
        DOCUMENT: Rate of erythroblast mortality at time t.
▦ peripheral_retics(t) = peripheral_retics(t - dt) + (retic_release - retic_maturation - periph_retic_mortality) * dt
    INIT peripheral_retics = 6e8
    TRANSIT TIME = 2
    INFLOW LIMIT = INF
    CAPACITY = INF
    DOCUMENT: Count of peripheral reticulocytes at time t.
```

```
    INFLOWS:
        retic_release = CONVEYOR OUTFLOW
            DOCUMENT: Rate of surviving marrow reticulocytes at time t.
    OUTFLOWS:
        retic_maturation = CONVEYOR OUTFLOW
            DOCUMENT: Rate of maturing reticulocytes at time t.
        periph_retic_mortality = LEAKAGE OUTFLOW
            LEAKAGE FRACTION = If HEM >0 Then HEM Else 0
            NO-LEAK ZONE = 0
            DOCUMENT: Rate of reticulocyte mortality at time t given by the sum of all user supplied hemorrhages.
RBC_population[Delay_Chain_D12](t) = RBC_population[Delay_Chain_D12](t - dt) + (mature_RBC_input[Delay_Chain_D12] -
RBC_loss[Delay_Chain_D12]) * dt
    INIT RBC_population[Delay_Chain_D12] = initial_Hgb*1e9/12
    DOCUMENT: An aging chain of RBC's, implemented in this package as an array of 12 bins, each bin being 10 days in duration. The
    maximum assumed lifetime of an RBC is assumed to be 120 days.
    INFLOWS:
        mature_RBC_input[1] = retic_maturation + 0*RBC_population[1]/time_constant
            DOCUMENT: Rate of maturing reticulocytes flowing in to bin 1 (1 to 10 days old) at time t.
        mature_RBC_input[2] = 0*retic_maturation + RBC_population[1] / time_constant
            DOCUMENT: Rate of RBC's flowing from bin 1 to bin 2 (RBC's that are 11 to 20 days old) at time t.
        mature_RBC_input[3] = 0*retic_maturation + RBC_population[2] / time_constant
            DOCUMENT: Rate of RBC's flowing from bin 2 to bin 3 (RBC's that are 21 to 30 days old) at time t.
        mature_RBC_input[4] = 0*retic_maturation + RBC_population[3] / time_constant
            DOCUMENT: Rate of RBC's flowing from bin 3 to bin 4 (RBC's that are 31 to 40 days old) at time t.
        mature_RBC_input[5] = 0*retic_maturation + RBC_population[4] / time_constant
            DOCUMENT: Rate of RBC's flowing from bin 4 to bin 5 (RBC's that are 41 to 50 days old) at time t.
        mature_RBC_input[6] = 0*retic_maturation + RBC_population[5] / time_constant
            DOCUMENT: Rate of RBC's flowing from bin 5 to bin 6 (RBC's that are 51 to 60 days old) at time t.
        mature_RBC_input[7] = 0*retic_maturation + RBC_population[6] / time_constant
            DOCUMENT: Rate of RBC's flowing from bin 6 to bin 7 (RBC's that are 61 to 70 days old) at time t.

mature_RBC_input[8] = 0*retic_maturation + RBC_population[7] / time_constant
            DOCUMENT: Rate of RBC's flowing from bin 7 to bin 8 (RBC's that are 71 to 80 days old) at time t.
        mature_RBC_input[9] = 0*retic_maturation + RBC_population[8] / time_constant
            DOCUMENT: Rate of RBC's flowing from bin 8 to bin 9 (RBC's that are 81 to 90 days old) at time t.
        mature_RBC_input[10] = 0*retic_maturation + RBC_population[9] / time_constant
            DOCUMENT: Rate of RBC's flowing from bin 9 to bin 10 (RBC's that are 91 to 100 days old) at time t.
        mature_RBC_input[11] = 0*retic_maturation + RBC_population[10] / time_constant
            DOCUMENT: Rate of RBC's flowing from bin 10 to bin 11 (RBC's that are 101 to 110 days old) at time t.
        mature_RBC_input[12] = 0*retic_maturation + RBC_population[11] / time_constant
            DOCUMENT: Rate of RBC's flowing from bin 11 to bin 12 (RBC's that are 111 to 120 days old) at time t.
    OUTFLOWS:
        RBC_loss[Delay_Chain_D12] = ( RBC_population[Delay_Chain_D12] / time_constant ) +
        RBC_population[Delay_Chain_D12] * HEM
            DOCUMENT: Rate of RBC death from each bin in the RBC chain plus losses due to user supplied hemorrhages at time t.
○ Aranesp_halflife = .9
    DOCUMENT: Drug elimination half life, measured in days.
○ ARANESP_Volume_of_Distribution = 1
    DOCUMENT: Effective volume into which drug is distributed, thus providing its observed concentration.
○ Aranesp_effect_on_mortality = Aranesp_in_circulation/(Aranesp_in_circulation+EC50)
    DOCUMENT: Moderates erythroblast and reticulocyte mortality rates, based upon drug concentration and epo resistance at time
    t.
○ Aranesp_concentration_in_circulation = Aranesp_in_circulation/ARANESP_Volume_of_Distribution
○ blast_mortality_fraction = IF (Aranesp_effect_on_mortality>.001) THEN
    (baseline_blast_mortality_fraction*(1-Aranesp_effect_on_mortality)) ELSE (baseline_blast_mortality_fraction)
    DOCUMENT: Value of baseline erythroblast mortality fraction as moderated by drug fractional effect.
```

○ CLINICAL_ARANESP_DOSE = IF ((mod(time,1) = .5) AND (CLINICAL_ARANESP_DATA > 1))

THEN (Pulse (CLINICAL_ARANESP_DATA,time,99999))

ELSE 0
   DOCUMENT: Historical drug dose administered at time t during the descriptive period of a simulation.
○ Release_of_hepatic_EPO = 1
○ retic_mortality_fraction = IF (Aranesp_effect_on_mortality>.01) THEN
   (baseline_reticulocyte_mortality_fraction*(1-Aranesp_effect_on_mortality)) ELSE (baseline_reticulocyte_mortality_fraction)
   DOCUMENT: Value of baseline reticulocyte mortality fraction as moderated by drug fractional effect.
○ sensitivity_to_Aranesp = { Place right hand side of equation here... }
○ time_constant = Avg_Lifetime/12
   DOCUMENT: Evenly allocates Average Lifetime to the respective durations in each successive RBC bin in the RBC aging chain.
○ Total_RBC_Count = ARRAYSUM(RBC_population[*])
   DOCUMENT: Cumulative number of RBC cells in the 12 bins of the RBC chain of the model.

The simulation performed using the equations described above results in a numerical approximation of the solution to a set of differential equations that describe accumulations in the chosen stocks (which represent integrals) as determined by their respective inflows and outflows (which represent derivatives). Specifically, the user of this model supplies, for an individual patient, historical Hgb values, historical darbepoetin alfa doses, the time period to be simulated, and the time increment, DT. The simulation, embedded in a simplified optimization routine (described below) then enables the user to determine a target dosing level and an associated dosing regimen that will obtain the desired Hgb values as long as the patient's current medical condition remains relatively unchanged.

Figure 9:
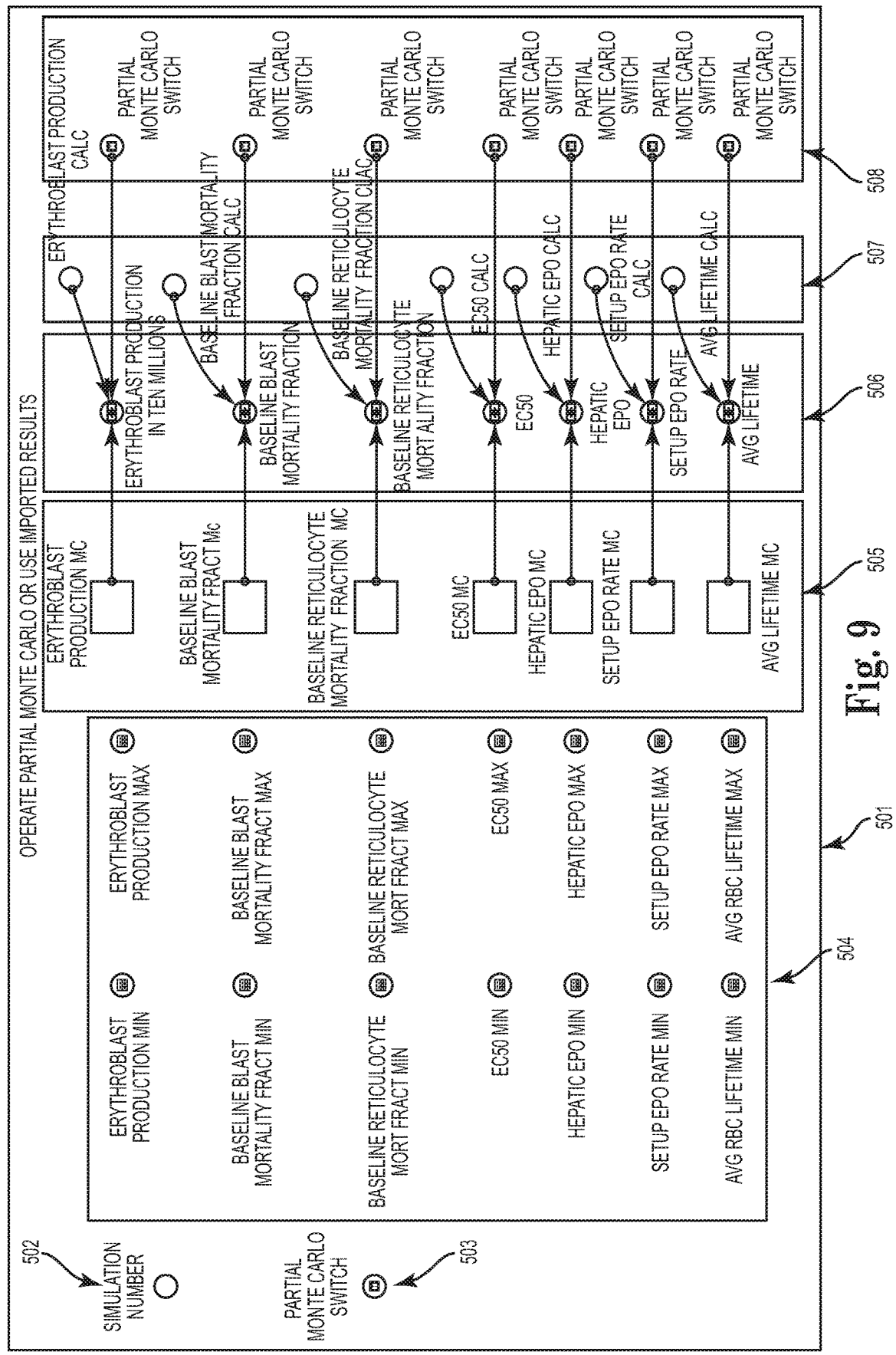
FIG. 9 is a screenshot of the portion of the biophysical simulation model that controls a Partial Monte Carlo simulation.

In one example, the biophysical simulation model may employ an adaptation of the Monte Carlo method to estimate parameter values. However, it shall be understood that other non-linear optimization routines may also be used, and that the disclosure is not limited in this respect. FIG. 9 presents the structure (501) that generates a collection of parameter values associated with simulation runs from which a best fit in the collection may be chosen by external (to the model) processing. The user, or the software system into which the model is integrated, specifies the number of simulation runs by providing a value for the converter named Simulation Number (502). The converter named Partial Monte Carlo Switch (503) is an on-off switch that controls the mode of the simulator: single simulation or multiple simulation. The Monte Carlo Switch is replicated (508) for each of the model parameters, informing the respective control converters (506) which parameter values are to be used in a given simulation: either the values in the CALC converters (507) in the case of a single simulation, or values in the in the respective stocks (505), which is the case when the Partial Monte Carlo Switch (503) is in the on position. The collection of parameter values that is generated by a Partial Monte Carlo simulation may be exported to a commercially available spreadsheet software which may be used to select the set of parameter values which produces the best fit between simulated Hgb values and the patient's historical values for the descriptive phase of the simulation, described below. Selected parameter values may then be reimported to the model for further processing and use in the Prescriptive Phase of the simulation, described below. Alternatively, a fully automated software system may perform these tasks. In that event, the data need not be exported to an external software application. Alternative examples of the Monte Carlo structure within the model (501), the method of best fit selection, and the movement of data exported from and imported into the model may be performed by a variety of methods, including a fully automated software system, all achieving the same purpose: to identify values for these, or other, parameter values and then make use of the parameters to find the weekly therapeutic dose (described below) which leads to the desired dosing regimen.

In this example, 100 or fewer simulations of the Monte Carlo method may be to choose an optimum value. However, in alternative examples of the model, thousands or tens of thousands of simulations might be run in a reasonable amount of time, which may allow for a more complete assessment of the distributions of each of the seven parameters. Further, this example of the model may not provide a unique solution. The same proposed dosing regimen might be developed for one patient with a low EPR, BMF, and RMF as for a patient with a high EPR, BMF, and RMF. Alternative examples of the model may allow potential classification of patients of the first or second type. In practice, however, proposed dosing regimens, though non-unique, may be quite adequate, resulting in 60% to 90% or more of the patients at a DCF achieving and sustaining Hgb values within the target range.

Each simulation is executed in three phases: Setup, Descriptive, and Prescriptive. Each phase is defined over a specific number of days. As described below, the Setup Phase extends from Day −200 to Day 1, the Descriptive Phase extends from the day number associated with a patient's first historical Hgb value (chosen by an analyst or chosen automatically by an automated software system) to the most recently available Hgb value or administered darbepoetin alfa dose. The Prescriptive Phase extends from the simulation day number of the first potential dosing date (generally one week after the end of the Descriptive Phase) to a simulation day number at which a proposed dosing regimen, given the selected parameter values, produces stabilized simulated Hgb values at the desired target value. The extent of each phase is identical for the two modes of simulation: the Monte Carlo Mode that generates a collection of random parameter values and associated simulated Hgb values, and the single simulation mode, in which proposed dosing regimens are developed or revised.

For the individual patient, the Descriptive Phase is used to select a set of parameter values that produces simulated Hgb values that match the historically observed Hgb values in response to historical drug doses over the duration of the Descriptive Phase. There will be a combined set of parameter values (e.g. the baseline progenitor input, baseline progenitor mortality in the absence of darbepoetin alfa, the EC50 of darbepoetin alfa, the level of protection provided, and the lifespan of circulating RBCs). This phase serves to define the 'pathophysiological state' of the patient, and the patient's sensitivity to the drug.

The setup phase begins at '−200 days', i.e. prior to 'Day 1', the day at which historical data is available (the beginning of the Descriptive Phase). The purpose of the setup phase is to identify a set of parameters that bring the system into a steady state (flat-line Hgb level equal to the patient's first Hgb value) prior to Day 1, and then simultaneously enable the system to follow the patient's response to darbepoetin alfa during the Descriptive Phase. The parameter Setup EPO (see Table 1) is used primarily in the Setup Phase to represent a mathematical dose of darbepoetin alfa, which, together with other parameter values in play at during the Setup Phase, achieves the results described immediately above. The parameter Setup EPO has no effect in subsequent phases but is rather replaced by either historical doses (in the Descriptive Phase) or proposed doses (in the Prescriptive Phase).

Given an appropriate set of parameter estimates, simulated Hgb values will respond to historical doses during the Descriptive Phase by generating simulated Hgb values that approximate the waxing and waning of historical Hgb values. The Partial Monte Carlo method, complemented by additional manual adjustments and/or automated adjustments, if required, is used to identify the best fit described above. Further, the best fit is defined as the simulated Hgb values within the extent of the Descriptive Phase, selected from a collection of simulations, which have a mean square error with respect to actual Hgb values in the Descriptive Phase of approximately 0.25 g/dL.

During the Prescriptive Phase, one or more of the following steps may be performed with fixed parameter values. A therapeutic dose (which may be a per session therapeutic dose or a weekly therapeutic dose (WTD) depending, among other things, upon the particular ESA to be prescribed) may be determined. In addition, in the event of a WTD, an analyst or automated system may introduce 'sample' dosage regimens, searching for a dosing regimen (dose and frequency) that delivers the equivalent of the WTD at a minimum cost. Frequently dose "pulses" may be required to quickly elevate Hgb values or avoid a projected undershoot. The dosage regimen is refined to bring the patient quickly and smoothly within the target Hgb range and to sustain that value. The selected dosing regimen may be extended several months into the future and remains effective as long as the patient's underlying medical condition remains relatively stable. In alternative examples, the search for a WTD and the selected dosing regimen may be implemented using automated software algorithms.

As described above, in this example of the biophysical simulation model, parameter values are optimized across the Setup and Descriptive phases using non-linear optimization methods (such as Monte Carlo techniques). However, it shall be understood that the present disclosure is not limited in this respect. Alternative examples may include, for example, other optimization strategies such as simplex algorithms and maximum likelihood estimators or other non-linear computational algorithms known to those of skill in the art.

The pharmacokinetic (PK) section of the model (FIG. 7, "Aranesp Dosing and Pharmokinetics") simulates the dynamics of circulating drug concentrations over time in response to various types (mathematical, historical, proposed) of dosing regimens and a simulated elimination rate. Alternative examples of the model may contain more extensive or refined PK representations. The pharmacodynamic (PD) section simulates the concentration-response influence of darbepoetin alfa on the time course and magnitude of the RBC count and release into the circulation. Once RBCs enter the circulation the clinician has no influence over their lifespan. Effective therapy is dependent upon an awareness of two critical delays within the process of erythropoiesis. First, the immediate effect of darbepoetin alfa is to increase (predictably delayed) Hgb values by replication and maturation processes within the bone marrow. Second, the decrease of Hgb levels is (predictably) delayed as a result of the persistent lifespan of circulating RBCs.

It is recognized that additional pathophysiological subsystems (and comorbid conditions) may influence Hgb levels over time. Alternative examples of the model may include, for example, iron availability and treatment regimens, bleeding, and the influence of inflammation on EPO resistance.

Other examples of the model may include additional parameter refinements, supporting disaggregation of biophysical subsystems, when these variations improve fulfillment of the purpose of the model.

Figure 10:
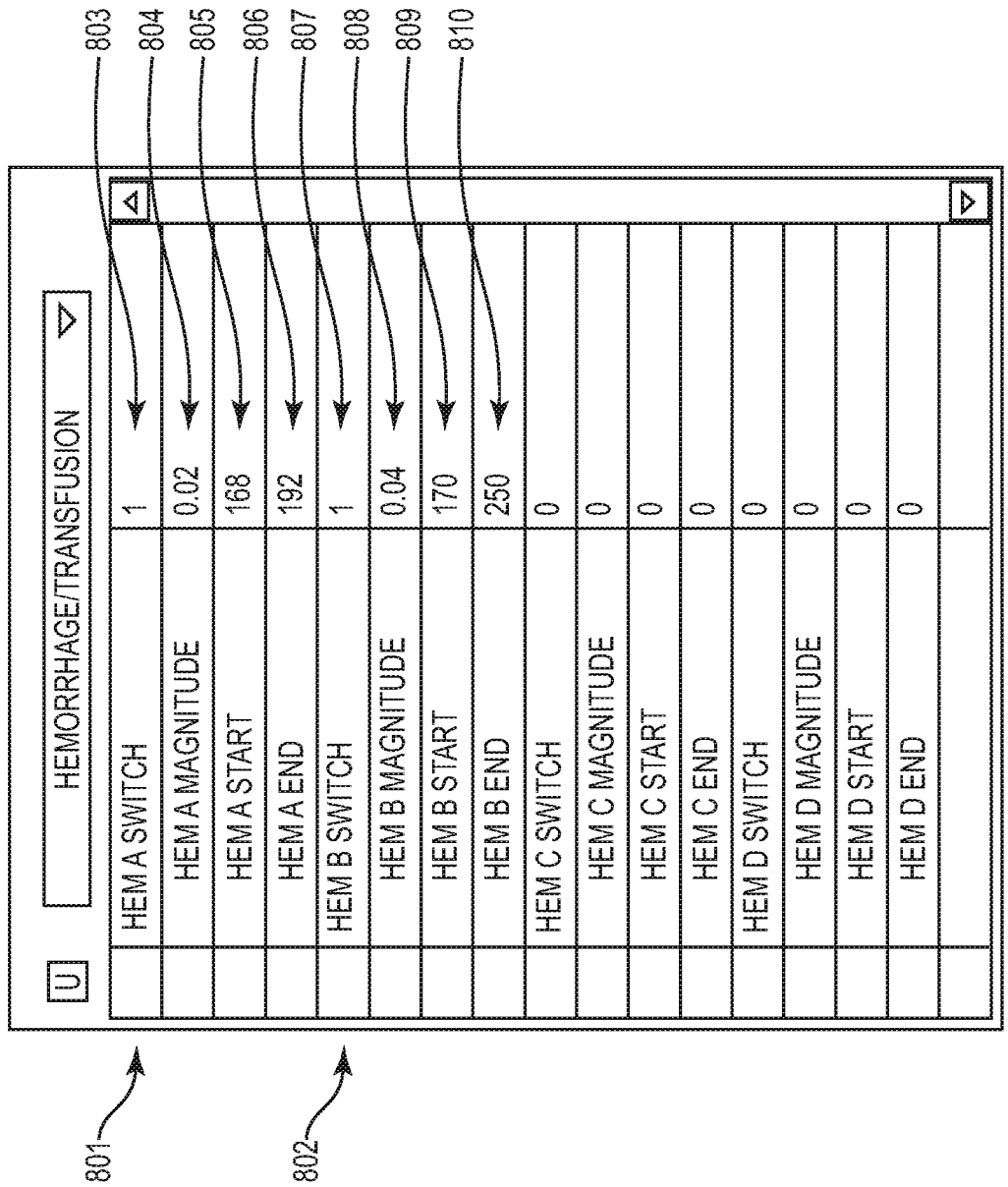
FIG. 10 is a screenshot that is used to specify patient specific hemorrhages used optionally in the example biophysical simulation model.

ESRD patients on dialysis frequently suffer blood loss for various reasons, such as bleeding from the access point to the patient's bloodstream or gastrointestinal bleeding. Other patient populations may also experience hemorrhages for various reasons. This example of the model includes the ability to specify up to four periods during which the patient experiences a hemorrhage. FIG. 6 shows how the variable HEM (608) is configured in the model. Note from this figure that hemorrhages are applied to RBC counts and peripheral reticulocytes in circulation. A portion of the user interface shown in FIG. 10 shows the control device used to specify hemorrhages. Alternative tools will have different but equivalent representations. In the illustrative example shown in FIG. 10, there are two active hemorrhages, A and B, specified by (801) and (802), having values set to the value 1, i.e., (803) and (807). The magnitudes of these two hemorrhages are specified as 2% per day and 4% per day, indicated by the values aligned with Hem A Magnitude and Hem B Magnitude (804) and (807), respectively. Items (805), (806), (809) and (810) specify the start and stop days for the two hemorrhages. Note that hemorrhages A and B overlap between days 170 and 192, in which case, the cumulative effect is used by the model. A negative magnitude may also be specified to simulate the effect of blood transfusions which are frequently administered to ESRD patients on dialysis, for example.

Although it is possible to identify individual factors that influence Hgb values over time, it is the interaction between these factors that influence the time course and magnitude of Hgb values in response to darbepoetin alfa and other ESAs. The present ESA dosing system includes a mathematical model that provides definitions of individual components, and then allows the controller to conduct simulations that reliably predict the behavior of the system as a result of perturbations that may be systematically introduced by an analyst or automatically by an automated software system.

The 'Weekly Therapeutic Dose' (WTD) is a theoretical value that defines the weekly dose that will ultimately maintain the patient's Hgb values at the midpoint of the target range. WTD is determined by systematically varying a fixed weekly dose and observing Hgb concentrations during the prescriptive phase of the simulation. The therapeutic dose determined by the ESA dosing system may be a per session therapeutic dose (PSTD) or a weekly therapeutic dose (WTD) depending, among other things, upon the particular ESA to be prescribed. In the case of Aranesp®, the system determines a WTD and then determines a dosing regimen that will deliver the equivalent of the WTD. In the case of other ESAs, the therapeutic dose determined by the system may be equivalent to the actual dosing regimen recommended for the patient.

Figure 11:
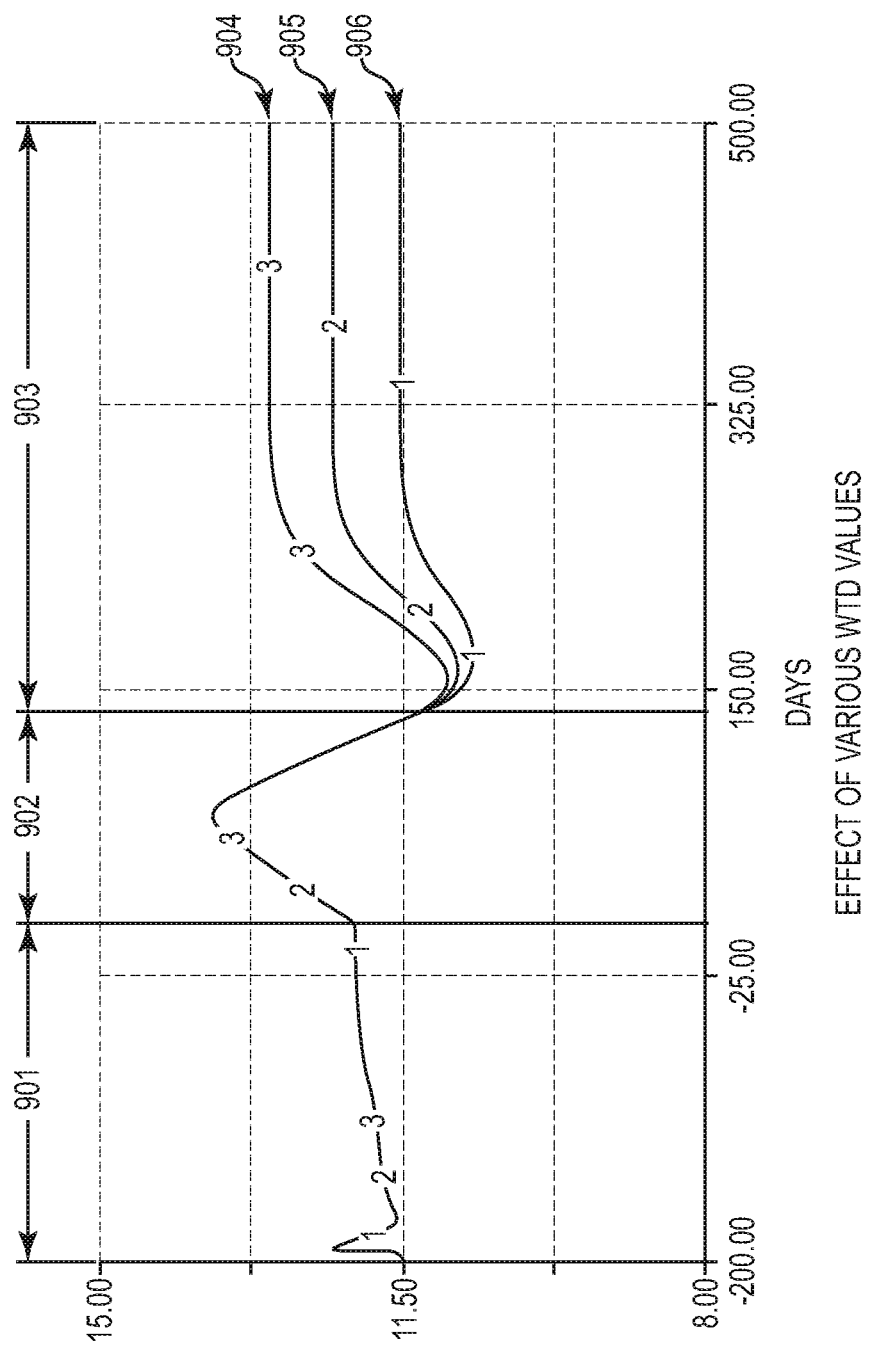
FIG. 11 is a graph illustrating the relationship of a specific patient's weekly therapeutic dose and the resultant steady state Hgb value.

FIG. 11 depicts three responses in simulated Hgb values, using parameter values obtained previously during the Prescriptive Phase, derived from historical darbepoetin alfa doses and actual Hgb values, to applied WTD's of 8, 12, and 16 mcg of darbepoetin alfa respectively. (901), (902), and (903) are the Setup, Descriptive, and Prescriptive Phases of the simulation, respectively. The WTD is applied in the model during the Prescriptive Phase only. The portion of the curves (904), (905), and (906) that are within the Prescriptive Phase of the simulation are simulated Hgb values, stabilized at 11.5, 12.3, and 13.0 g/dL respectively in response to the three WTD's described. This example of the model provides the user with projections of future Hgb values in response to various WTD's and associated dosing regimens.

Figure 12:
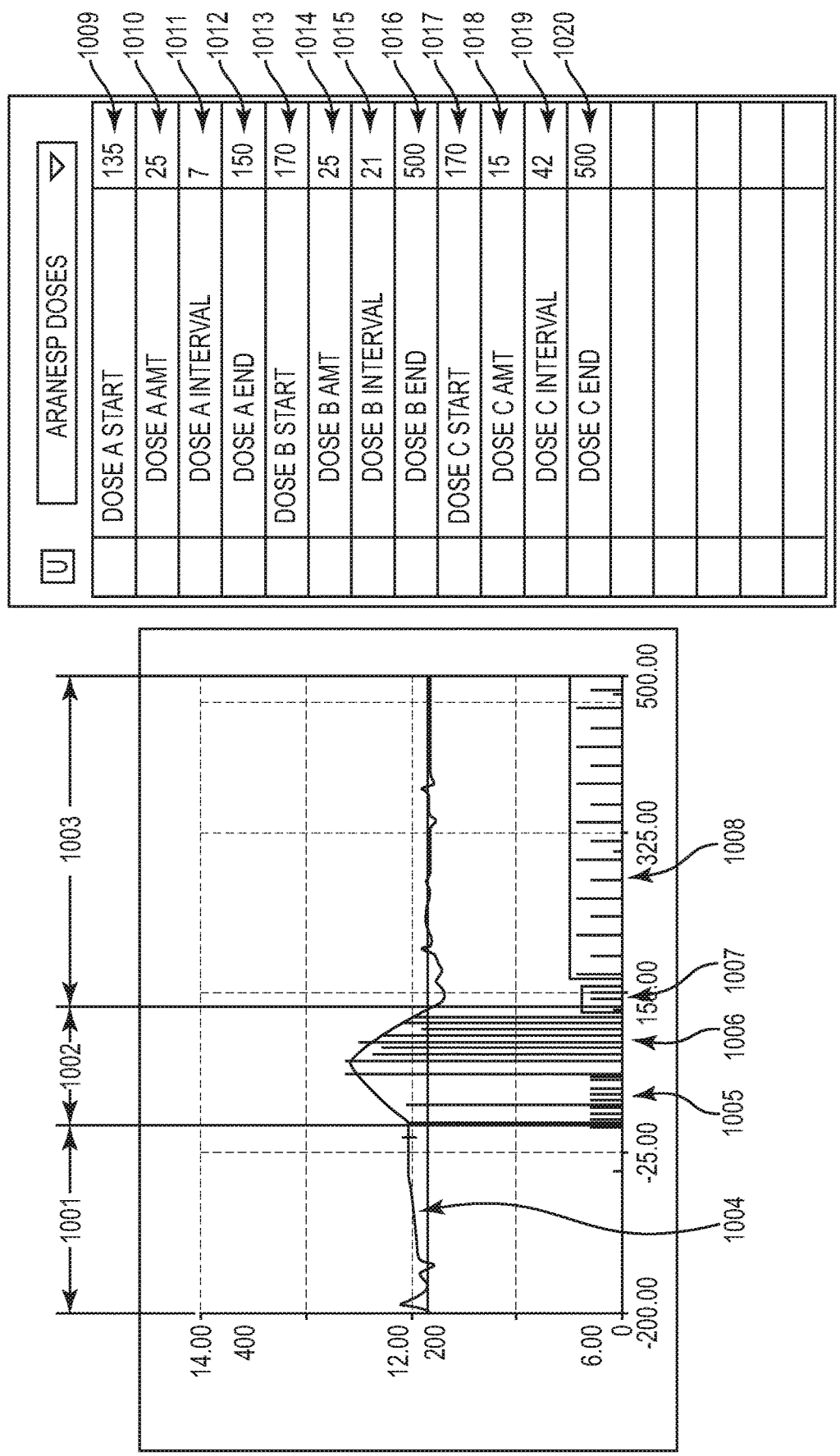
FIG. 12 is a composite figure, consisting of a graph illustrating the relationship of the weekly therapeutic dose to a specific dosing regimen, together with a screenshot of the device that is used to specify dosing regimens.

The WTD derived in the Prescriptive Phase of the simulation is the clinician's guide to developing a dosing regimen. A dosing level and the frequency at which to administer the chosen doses may then be chosen from commercially available doses. For some ESAs, the WTD may be unequal to commercially available doses (in the case of Aranesp®, for example), and this may require a mix of doses be applied at various frequencies that together will deliver a dose equivalent to the WTD. Further, on the date the dosing regimen is to be started, the patient may currently be either above or below the target range, with either an upward or downward trend in Hgb values. In such cases "pulse" doses must be found that will quickly and smoothly achieve Hgb values within the target range. FIG. 12 displays a complete scenario:

(1001) denotes the Setup Phase
(1002) denotes the Descriptive Phase
(1003) denotes the Prescriptive Phase
(1004) portrays simulated Hgb values in each phase
(1005) reports historical ESA doses administered in the Descriptive Phase
(1006) reports historical Hgb values measured during the Descriptive Phase
(1007) reports three pulse doses to initiate the Prescriptive Phase, designed to arrest the concurrent downward trend in Hgb values
(1008) reports the proposed dosing regimen that will sustain Hgb values at 11.5 g/dL
(1009) is the simulation day number of the first dose in the three dose pulse (1007)
(1010) is the amount of the dose to be administered as Dose A
(1011) is the interval in days for Dose A
(1012) is the end date for Dose A
(1013)-(1016) are the analogues of Dose A specifications, to be applied as Dose B
(1017)-(1020) are the analogues of Dose A specifications, to be applied as Dose C Thus, in this case, the steady state dosing regimen is found to be: "Starting on day 125, give three weekly doses of 25 mcg, followed by alternating doses of 25 mcg and 40 mcg every 21 days".

One concept of dynamic modeling in the example system described herein is that recommended strategies (i.e., dosing regimens) are hypotheses as opposed to "black box answers". These hypotheses are to be tested by follow up measurements of actual future Hgb values of the patient and either confirmed or rejected. Both confirmation and rejection of a hypothesis provide insight and understanding of how the process under study actually operates, which is a major goal to be achieved from a dynamic modeling perspective, generally and particularly. To that end, the system may also include, for example, components and tools for follow up, analysis, learning, revision, improved anemia management skills, and ultimately the well being of the patient.

The example system described is a clinically applicable set of tools designed to address and resolve Hgb cycling. The example system includes a collection of components that have been loosely coupled by means of various software components. Alternative examples of the system may include tightly integrated modules of functionality, providing an information system that supports anemia management for individual patients receiving therapy at one or more Dialysis Care Facilities (DCF).

The purpose of the system is to capture, cleanse, maintain, transform, analyze, and create data and information required by clinicians to effectively manage anemia concerns for a population of individual patients.

Figure 13:
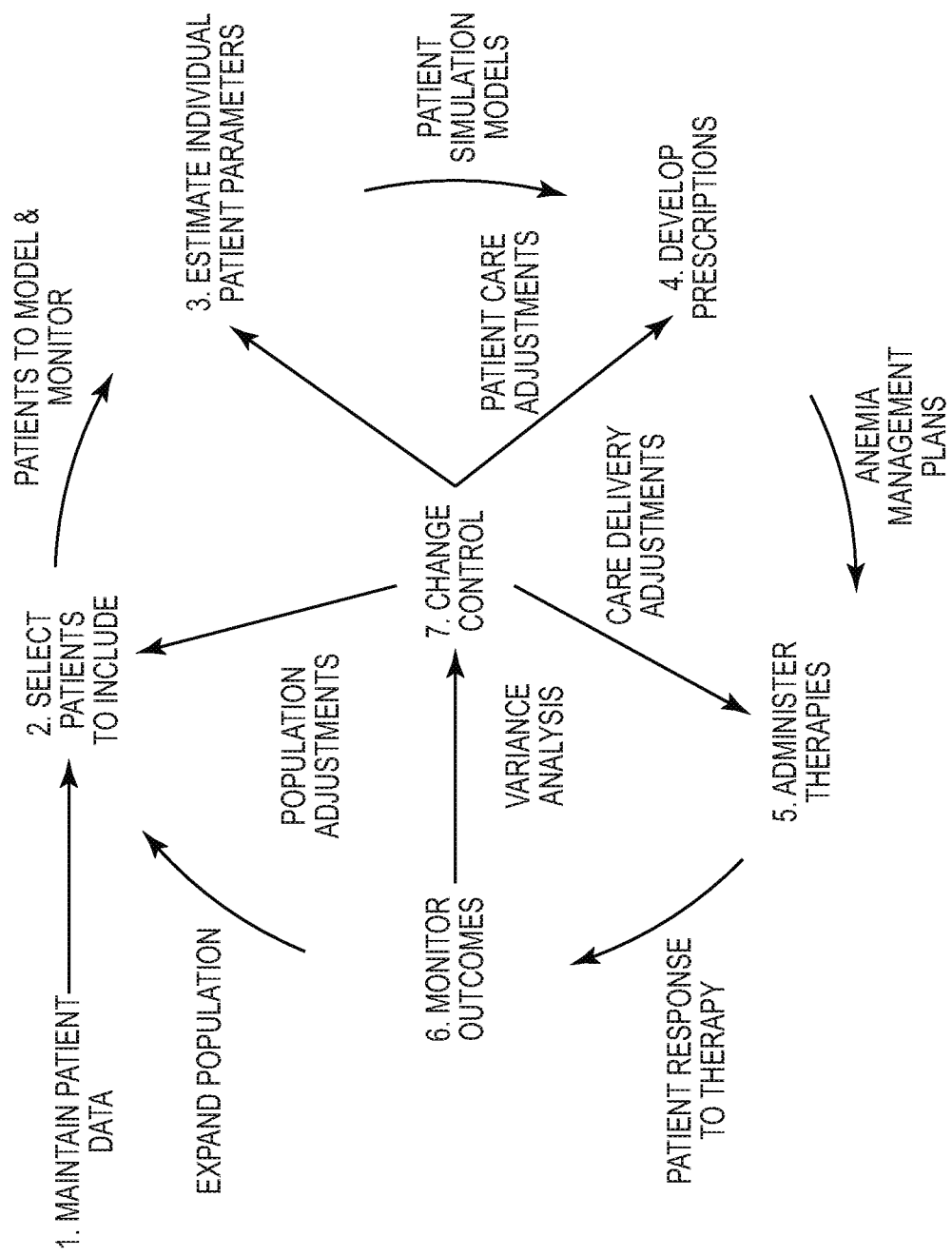
FIG. 13 is diagram illustrating an example process by which the ESA dosing techniques described herein achieve and maintains stable Hgb levels for ESRD patients receiving ESA therapy.

FIG. 13 is a diagram illustrating an example of the overall process by which the system achieves and maintains stable Hgb levels for patients receiving ESA therapy. The first aspect of the process includes gathering and maintenance of historical hemoglobin (Hgb) data and ESA dosing data for a particular patient. Historical measured actual Hgb levels and corresponding ESA dose history, along with identifying information and other relevant information (such as hospitalizations, iron studies, transfusions, infections, and other factors that may affect Hgb levels) for all ESRD patients at, for example, a DCF or group of DCFs, may be obtained and stored in a database or other medium for storage and retrieval of the information. Behavior over time (BOT) charts (such as those shown in FIGS. 2 and 3) are generated that assist the analyst in each of the three phases of a simulation.

The first step in treating a population of patients is to select applicable patients. In one example, the system is designed to treat iron replete patients who have a minimum of 6 recorded Hgb values. Patient data described above is assembled and organized for processing and maintenance. In other examples, the system may include iron metabolism components, potentially enabling the inclusion of patients who were not iron replete during the period in which Hgb values were obtained.

Obtaining and maintaining individualized simulation parameters, whether those described above, or refinements and parameter improvements, are stored in a database. Alternative examples may include effective classifications of Hgb response profiles, potentially creating improved methods of treatment.

Individualized recommended prescriptions are stored in a database which permits overall analysis of ESA consumption and improved management of associated costs. In this example of the system, the database is implemented in a commercially available spreadsheet program. Alternative examples may include implementation of customized database application using commercially available database engines, data transformation tools, analysis and reporting.

Recommended prescriptions are reviewed and approved by authorized providers. The example system provides recommend dosing regimens. In addition, clinicians' anemia management skills may be improved through use of the system.

Approved prescriptions may be entered into a provider's order management system. The ESA dosing system may be loosely coupled with a medical order management system. Alternative examples may include software components that tightly integrate each step in the process from a data and information perspective. Alternative examples may also provide improved ESA consumption management which may significantly reduce a variety of operational costs, such as reduced drug consumption, reduced carrying inventories, reduced spoilage, reduced administrative costs, and reduced administrative costs associated with preventable emergent medical issues.

The ESA dosing system may also include data collection tools designed to monitor the compliance of drug administration with medical orders. Hgb cycling often arises from dose misadministration. Using these tools, the ESA dosing system may detect dose misadministration and prompt as well as design corrective interventions.

As described above, the recommended dosing regimen, once approved and ordered, is a hypothesis awaiting confirmation or rejection, each of which improves insight. The ESA dosing system may include, for example, weekly monitoring of Hgb values for a minimum of 12 weeks, allowing the clinician to detect and diagnose the causes of observed deviations of actual Hgb values from those that were predicted by the simulation.

Figure 14:
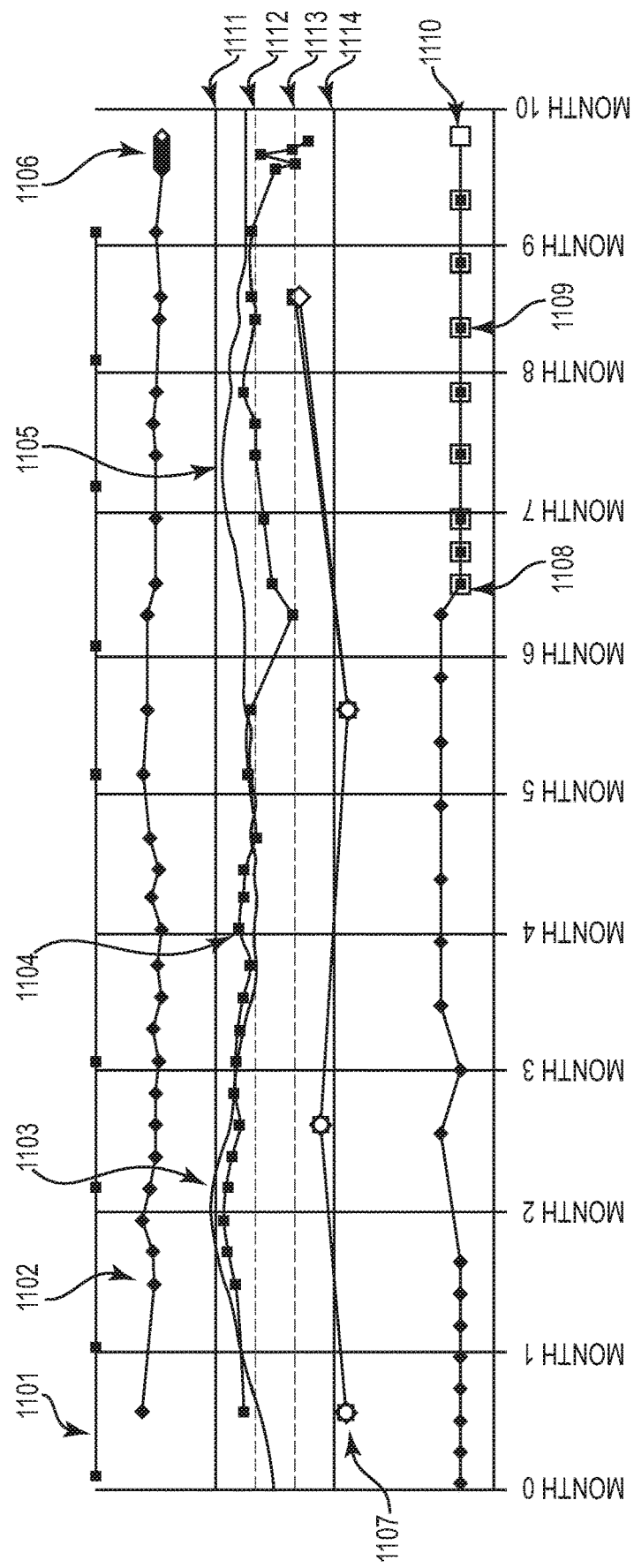
FIG. 14 is a screenshot of a behavior over time chart that displays selected variables.

The BOT chart is a tool used by clinicians in the implementation of the methodology supported by the system. FIG. 14 shows an example of an individual's BOT chart that tells the story of anemia management effectiveness. FIG. 14 contains the following information for a 10 month period:
1101 administered iron (Venofer®)
  1102 Mean Corpuscular Volume (MCV)
  1103 simulated Hgb values for a portion of the Descriptive period
  1104 actual Hgb values

1105 projected Hgb values in response to planned therapy
1106 hospitalized 7 days for pneumonia
1107 transferrin saturation and iron values (resting upon one another, but with different scales)
1108 boxes represent recommended and approved dosing regimen
1109 dots within boxes represent actual aranesp doses administered
1110 open box represents recommended and approved dose either missed or not yet administered
1111 upper bound of target Hgb range (13.0 g/dL)
1112 upper bound of optimal target Hgb range (12.0 g/dL)
1113 lower bound of optimal target Hgb range (11.0 g/dL)
1114 lower bound of target Hgb range (10.0 g/dL)

A given patient's BOT, containing these and other data (such as the time course of vital signs) enables the clinician to develop a comprehensive picture of the patient's overall condition. Axis labels and scales are not shown in FIG. 14 for brevity. The example system includes an underlying database of patient results and a web based report (the BOT), along with various filters that quickly isolate patients with Hgb values deviating from expected values. The example system enabled one physician assistant to monitor the status of 370 patients and recommend interventions in a four hour period.

The process may also include a structured change control process. The ESA dosing system may be designed to anticipate changes or replacements to any or all of the system components. For example, the ESA dosing system may anticipate changes in an individual patient's underlying medical condition. These changes may require resimulation of a new recommended prescription, or searching for a new set of parameter values and then developing a new recommended prescription. The ESA dosing system may include tools whereby an analyst can retrieve previously modeled patients and begin anew. Alternative examples may include information system components that maintain histories of identified parameter values, prescriptions, and changes over time of the patient's medical condition. This information may improve insights and an operational understanding of the relationship between the progression of CKD for ESRD patients on dialysis and Hgb response profiles.

Figure 15:
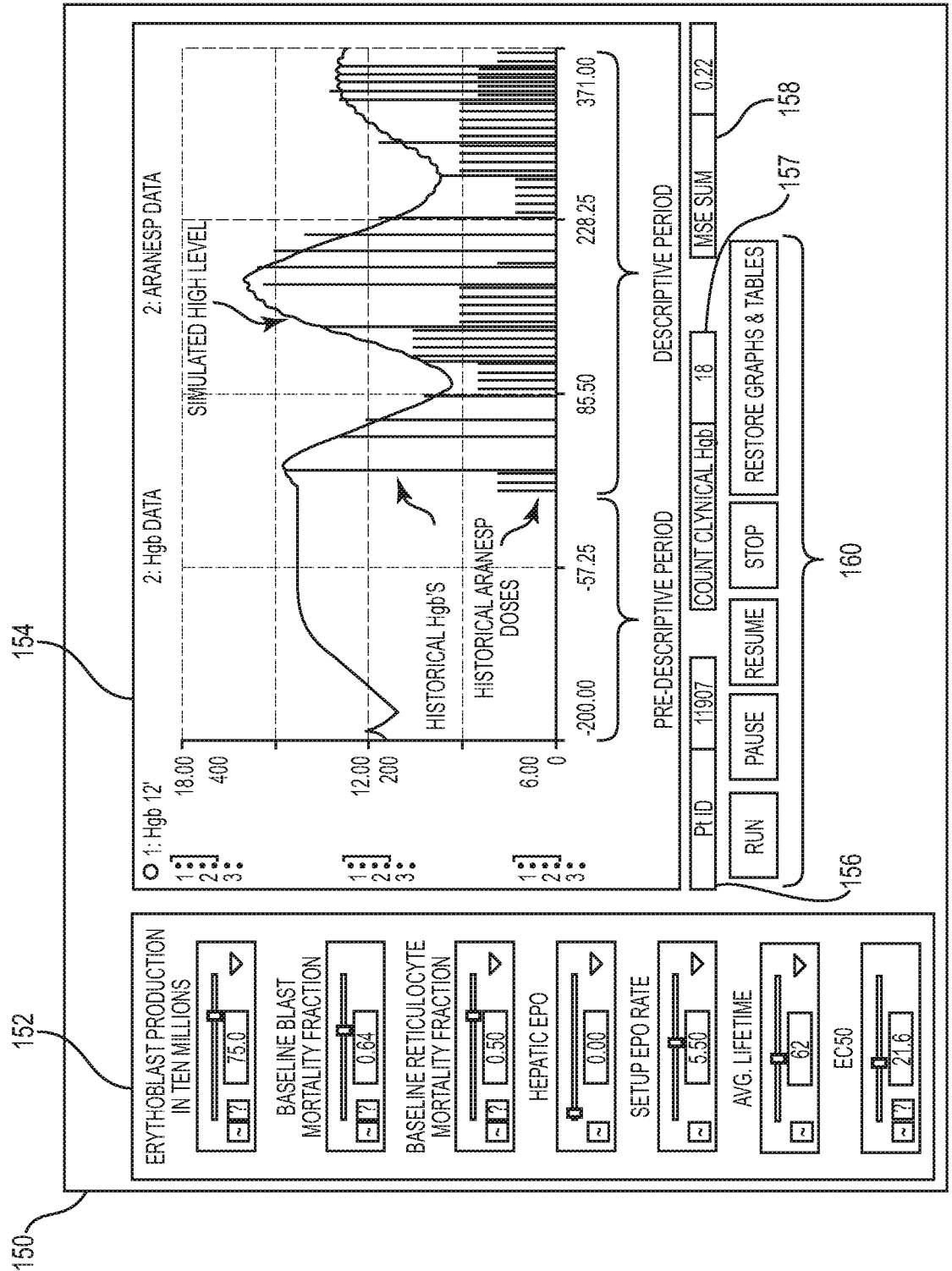
FIG. 15 is a graph illustrating an example curve fitting result for the descriptive phase.

FIG. 15 is an example screenshot of the simulation engine control panel for the pre-descriptive setup period and the descriptive period. This is an example screenshot that could be displayed on user interface 22 (FIG. 1). A control panel 152 allows the user to set minimum and maximum search values for each of the patient-specific parameters. A graphing area 154 graphically displays historical Hgb levels, historical ESA dosages and simulated Hgb levels for the pre-descriptive setup and descriptive periods. A patient ID 156, Count Clinical Hgb 157 and the mean standard error (MSE) for the currently displayed simulation are also displayed. A series of function buttons 160 permit the user to run, pause, resume, stop, restore graphs and tables, and/or perform other relevant functions related to the biophysical simulation. Although specific data, graphs, and functional interfaces are shown in FIG. 6, it shall be understood that the disclosure is not limited in this respect, and that other relevant data, graphs, tables, charts or other ways of displaying data may also be displayed, and that other types of functional interfaces, such as touch screen, mouse, stylus, keyboard, multi-touch, mobile devices, or other method of interacting with the program may be used without departing from the scope of the present disclosure.

The graph 154 of FIG. 15 illustrates an example curve fitting result for the descriptive phase. In this example, the descriptive period for this patient was 371 days in duration. During that period, 18 actual Hgb values were measured, and those values display the typical oscillation. 37 doses of darbepoetin alfa were administered in the descriptive phase. When Hgb values were too high, darbepoetin alfa was withheld. When Hgb values were too low, darbepoetin alfa doses were increased.

The model uses a so called pre-descriptive period to establish an erythropoietic equilibrium with an RBC count, which reflects the Hgb level that is near the first observed Hgb result in the descriptive period. In this example, the pre-descriptive period in the model is 201 days in duration, running from day −200 to day 0. This is the period of time the body requires to establish equilibrium in the presence of a theoretical (mathematically applied) daily ESA dose. The model uses the parameter values displayed on the left of the FIG. 15 to simulate an Hgb value from Day −200 to Day 371.

The search for parameter values stops when the Mean Square Error (MSE) between the simulated Hgb values and observed Hgb values in the descriptive period is sufficiently small. In FIG. 15, the MSE is reported as 0.22, meaning that on average, the simulated Hgb values are within +/−0.47 g/dL of the actual Hgb values.

The simulation based approach solves the problem of overshoot and undershoot by associating the post administration exponential decay in ESA concentration levels with the delays involved in red blood cell production. The model accounts for the production and mortality of RBC precursor cells. By providing estimates of RBCs "in the pipeline", the provider can extract advice from the biophysical simulation engine that will create a dosing plan that will achieve an adequate and stable Hgb value within a target range.

As discussed above, an output of the process is the calculation of the weekly therapeutic dose (WTD) required for a stable Hgb at the target value or within a target range. The WTD is the theoretical weekly dose required to achieve the intended therapeutic response. That is, a dose level which, if administered weekly, would stabilize a patient's Hgb at the target level.

Figure 16:
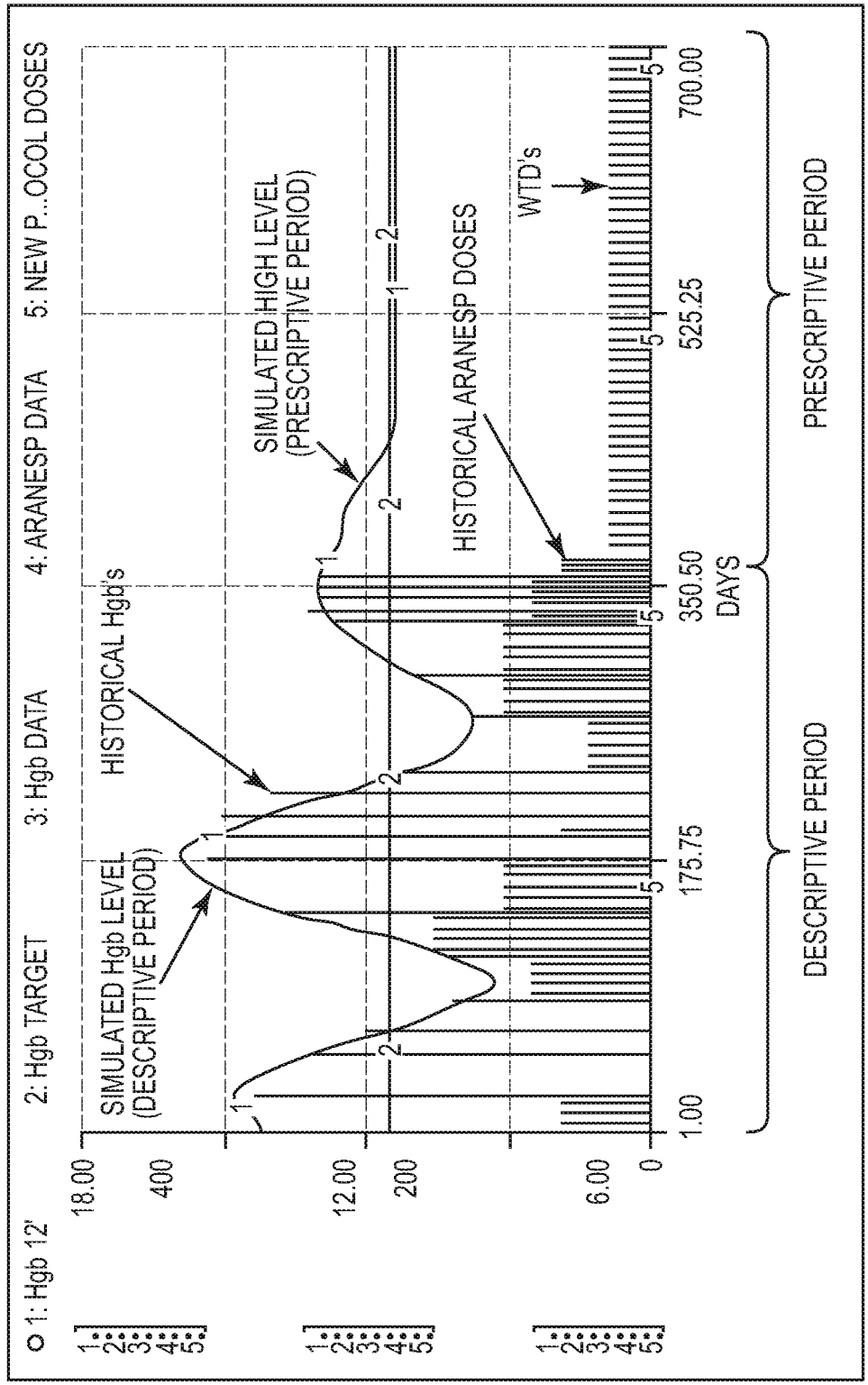
FIG. 16 is a graph illustrating an example weekly therapeutic dose (WTD) calculation result.

FIG. 16 is a graph illustrating an example WTD calculation result for the same patient shown in FIG. 15. This graph could be displayed in the graphical portion 154 of the control panel 150 of FIG. 15. In this example, the descriptive period was 370 days in duration (day 1 to day 371). The prescriptive period is extended to 700 days from day 0 (or a total of 330 days). Typically, this should be ample time for the RBC production chain to stabilize in response to a proposed constant WTD. 18 actual Hgb values were collected in the descriptive period. 37 doses of darbepoetin alfa were administered in the descriptive phase. When Hgb values were too high, darbepoetin alfa was withheld. When Hgb values were too low, darbepoetin alfa doses were increased. These results display a typical oscillation, with values well below and well above the target range of 10-12 g/dL.

The simulation of the prescriptive phase of the patient included a weekly dose titrated to deliver the equivalent of 25 mcg of darbepoetin alfa per week. As shown by the simulated Hgb levels for the prescriptive period, Hgb would stabilize at 11.5 g/dL after a little over 60 days.

Once the system determines the optimized WTD, the system may assist providers in finding the most effective combinations of available dosing levels at the optimal frequency of administration that will deliver the required WTD, and as a result, achieve and maintain the desired Hgb value. This may include, for example, titrating available dosing levels that will deliver the equivalent of the WTD.

The example illustrated in FIG. 16 indicates a WTD of 25 mcg. Since 25 mcg is a standard available unit doses, this is the prescription the system may recommend.

For other patient simulations, WTD values that are not equal to available unit doses require experimentation to determine the optimal dosing strategy. For these patients, the process may guide the provider to a titration scheme that achieves the intended result.

After a proposed prescription is approved and administration has begun, the patient's situation will invariably change. A hospitalization, an infection that increases resistance to ESA therapy, or a hemorrhage may occur that changes the patient's response to ESA therapy.

In accordance with another aspect of the example ESA dosing system, it has been determined that Hgb measurements taken in the prescriptive period that differ from the projected (simulated) response are reliable indicators that the value of at least one of the patient-specific parameters has changed. Identification of changes in observed Hgb levels from the projected response may be used to prompt focused assessments about changes in the patient's condition that may lead to effective corrections.

For example, variance in Hgb levels from the projected response may be related to a condition or situation that was not present during the descriptive phase. Re-modeling may be used at this point to seek an alternative set of patient-specific parameters values. The newly updated parameters may then be used to yield an effective corrective action, that is, an updated WTD, to restore an adequate and stable Hgb value.

Monitoring of Hgb levels during the prescriptive period may therefore be a part of the systemic solution. This part of the process is a probe that scans for changes in the patient's condition, develops corrective actions, and communicates the required changes in a timely and effective manner.

Figures 17A, 17B:
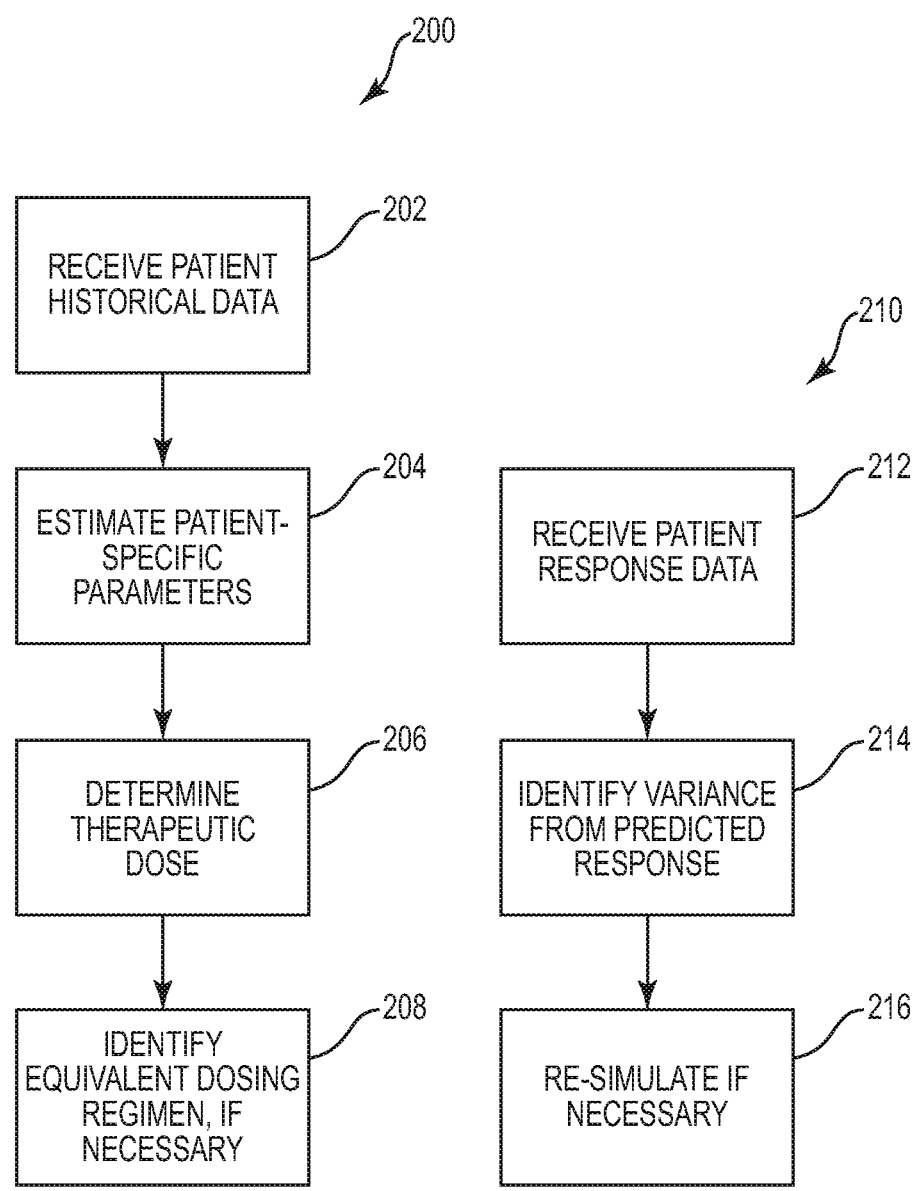
FIGS. 17A and 17B are flowcharts illustrating example processes by which a processor determines a weekly therapeutic dose (WTD) that will result in stabilization of Hgb to a target level and monitors the patient response.

FIG. 17A is a flowchart illustrating an example process 200 by which system 10 (FIG. 1) or system 1240 (FIG. 20) may determine a therapeutic dose that will result in stabilization of Hgb to a target level or keep it within a target range. Historical Hgb and corresponding ESA dosage data is received (202). Patient-specific parameters are estimated (204). In one example, Monte Carlo methods such as those described herein, or other non-linear optimization routines, may be used to arrive at an approximation of model parameters for individual patients. The parameters may be manually or automatically adjusted to improve fit between historical and simulated Hgb values for the descriptive period chosen.

The system determines a therapeutic dose that results in stabilized Hgb within the target range (206). In the event that the therapeutic dose is a WTD, the system may identify one or more dosing regimens that deliver the equivalent of the WTD (208). The one or more equivalent dosing regimens may be developed for a 30, 60, 90 or other day regimen, up to six months, for example. Other variables for the equivalent dosing regimens may include the dosage given per dialysis session and/or the number and frequency of doses. Multiple dosing regimens from among available titrations of ESA therapy may be identified, and a dosing regimen that minimizes one or more variables such as the dosage given per dialysis session, the number or frequency of doses, cost, or other appropriate factors.

FIG. 17B is a flowchart illustrating an example process by which system 10 monitors the patient response to the identified dosing regimen and makes changes if necessary (210). The patient response to the therapeutic dose is monitored (212). The measured Hgb levels during the prescriptive period are compared to the predicted Hgb level. Variations from the predicted response are identified (214). The causes of the variation are assessed. The model may be re-simulated to obtain an updated therapeutic dose and equivalent dosing regimen, if necessary (216).

In addition, corrective therapies may be identified, diagnostics may be ordered, statistics summarized and group performance reports developed.

Figure 18:
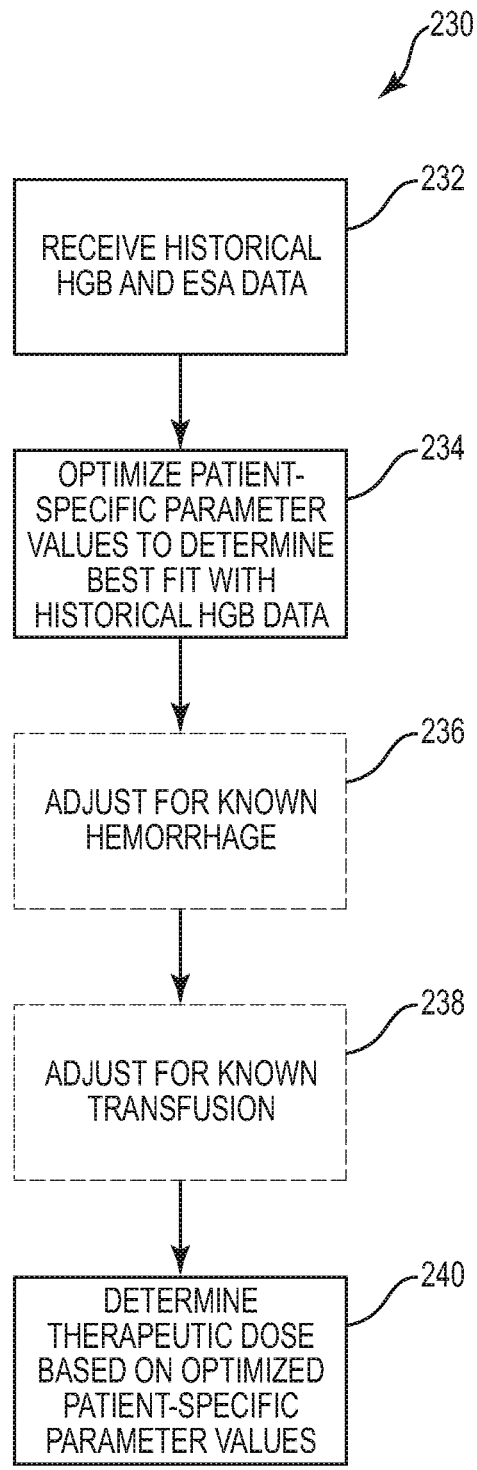
FIG. 18 is a flowchart illustrating an example process by which individual patient parameters may be determined.

FIG. 18 is a flowchart illustrating another example process 240 by which the ESA dosing system may determine the patient-specific values of the model parameters and the therapeutic dose that may maintain the patient's Hgb within a target range. The patient-specific historical Hgb levels and corresponding ESA dosing data are received (232). The system optimizes the patient-specific parameter values to determine a best fit with the patient's historical Hgb data (234). For example, Monte Carlo or other optimization methods may be used to determine the optimized patient-specific parameter values. The parameters may be optimized to result in a minimum Mean Squared Error (MSE). For purposes of this description, the MSE refers to the sum of the squared deviations of simulated Hgb values from the actual value obtained divided by the number of observations in a given time series of Hgb values. In some examples, the parameters may be manually or automatically adjusted to improve fit between historical and simulated Hgb values for the descriptive period chosen.

If applicable, the patient-specific parameter values may be manually or automatically adjusted to account for known hemorrhages (236) or transfusions (238). The system then determines the therapeutic dose based on the optimized patient-specific parameter values that may maintain the patient's Hgb within a target range (240).

Figure 19:
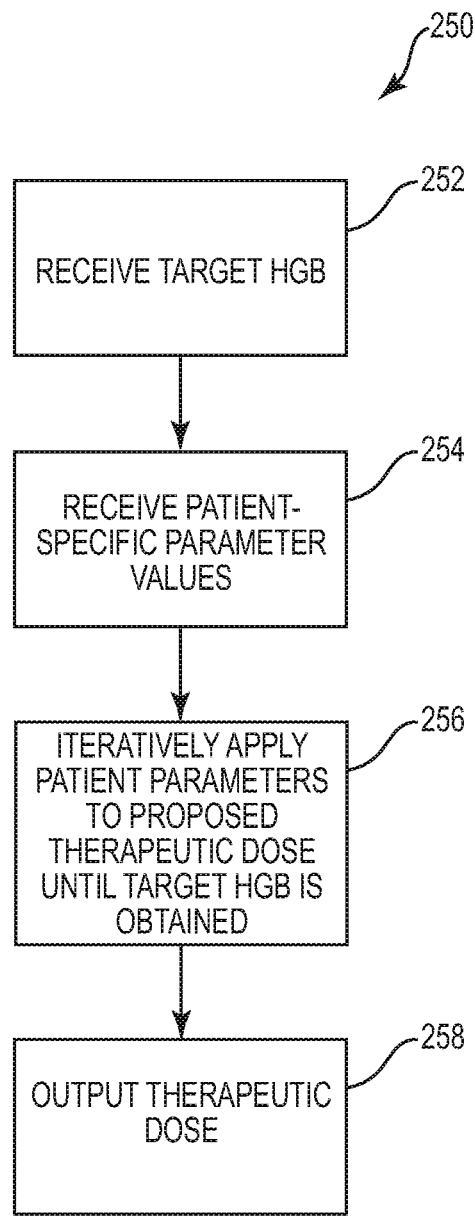
FIG. 19 is a flowchart illustrating an example process by which a weekly therapeutic dose (WTD) may be determined.

FIG. 19 is a flowchart illustrating an example process 250 by which processing unit 20 (FIG. 1) or processing unit 1260 (FIG. 20) may determine a therapeutic dose that may maintain the patient's Hgb within a target range. The target Hgb range is received (252). The target Hgb may be input by the user via user interface 22 (FIG. 1), or may be automatically determined. The patient-specific parameter values are also received (254). The system may iteratively simulate, based on the patient-specific parameter values, the patient's Hgb response to a series of proposed therapeutic doses until the simulated Hgb is maintained within the target range (256). The proposed therapeutic dose that results in stabilization of Hgb levels within the target range is identified as the therapeutic dose (258).

In one example, "optimal" patient-specific parameter values are identified through a type of Monte Carlo simulation that minimizes the mean square error between simulated Hgb values and the patient's actual Hgb lab history. A Monte Carlo simulation is a method of randomly selecting model parameter values to be used in a simulation in order to seek optimal values selected from the results of a large number of simulations.

Simplified (e.g., less processing intensive) versions of the Monte Carlo simulation may run only 100 or so simulations, whereas more robust versions may allow thousands or tens of thousands of simulations. Expanding the Monte Carlo sample space by orders of magnitude may improve the reliability of the proposed prescriptions and/or reduce the need for expert judgment. In addition, as described herein, other non-linear optimization routines may also be used to obtain the patient-specific parameter values, and the disclosure is not limited in this respect.

The example biophysical simulation engine described above was limited to those ESRD patients that were iron replete throughout their descriptive periods. This permits exclusion of iron metabolism components from the simulation engine. However, it shall be understood that iron metabolism components may be added to the example system to accommodate patients who experience periods of iron deficiency, and possible reduced responsiveness to ESA therapy.

As described above, the biophysical simulation engine estimates Hgb values based on the red blood cell count. An alternative would be to add model components that include whole blood hematocrit calculations. For example, blood plasma and fluid dynamics model components could be added. These alternatives may account for any hemodilution and hemo-concentration effects. Once the hematocrit is known, an estimate of the Hgb level could be derived that would be more accurate than the current estimate.

As discussed above, variances from projected Hgb levels may be used as a diagnostic, enabling users to anticipate and potentially prevent undesirable outcomes. In each case where significant variances were observed, a model based upon the patient's new reality may be reconstructed, allowing the system to create a revised prescription and to continue pursuing an adequate and stable Hgb level with a revised therapy.

In addition to improvements in the management of anemia, with adequate and stable Hgb values achieved, the patient will have more stamina to comply with the rigors of life on dialysis. As a result, hospitalizations may decrease, missed sessions may decrease, mortality may be reduced, and dietary restrictions may be more valued and observed. The patient may obtain the presence of mind to effectively engage with managing the details of creating their own health outcomes. Because missed ESA doses perturb Hgb values, the information provided by this process greatly reduces the risk of missed doses going uncorrected.

Elimination of Hgb cycling for an individual patient eliminates a number of patient health risks. Hgb cycling is an indicator that all the systems of the body are experiencing alternating periods of excessive and diminished oxygen supply. It is believed that this variation in oxygenation leads to increased hospitalization rates and mortality. Stable Hgb values improve patient quality of life and reduce overall health risks. In addition, it may make it easier for health care providers to recognize the onset of new comorbidities in their patients who have a stable Hgb while on therapy since in general new medical problems may lead to a fall in Hgb.

In one example, the ESA dosing system is applied to patients receiving dialysis and darbepoetin alfa (or other ESA) therapy. CKD patients who are not on dialysis, however, also may require ESA therapy. CKD is a progressive disease and generally leads to the initiation of renal replacement therapy, most frequently, dialysis. Hgb cycling among CKD patients not on dialysis has also been observed. Thus, in other examples, the system may also be applied to those CKD patients currently not on dialysis, improving their overall health and stamina, and designing therapies to postpone the initiation of dialysis and the associated rigors and costs.

In other examples, the ESA dosing system may be applied to any patient requiring ESA therapy.

In general, ESRD, CDK, and other patients with adequate and stable Hgb values are easier for care providers to manage. In addition, the ESA dosing system may create a new perspective for care providers concerning RBC homeostasis. Insights gained by the successful management of Hgb values using the system and methods described herein may be, at least partially, transferrable to patients who have not been assessed using the ESA dosing system described herein. For example, such insights may permit more accurate and optimal dosing regimens to be designed. Thus the ESA dosing system may reduce the complexity, time, and cost of caring for patients and improve effectiveness at the same time.

The ESA dosing system and methods described herein may also improve management of ESA inventories at Dialysis Care Facilities. Using this system, accurate projections of ESA requirements may be made, reducing excess inventory. Because ESA are relatively expensive, this reduction in inventory may result in great savings per year in inventory costs. Projected, precise dosing regimens for each patient receiving dialysis at a Dialysis Care Facility (DCF) for the future (90 days, for example) equips the DCF with a more accurate estimation of the required ESA inventory levels. This can reduce the cost of waste and other costs associated with carrying excessive inventories.

The system and method described herein allows creation of dosing regimens that achieve adequate and stable Hgb values that also consume a minimum amount of ESA drugs. Retrospective assessments of the data has produced an estimate that ESA costs may be reduced by as much as 46% or more.

The system may include an analysis and reporting subsystem that provides, for example, "at a glance" overviews of patients with below target Hgb values, in range, or above target Hgb values. Maintaining adequate and stable Hgb values for a higher percentage of patients may enable providers to spend less time per patient, and allocate more time to the care of patients with emergent medical issues.

The ESA dosing system may be used to increase the efficacy and efficiency of administered ESAs while achieving adequate and stable Hgb values. This is a primary concern of CMS and may represent significant cost savings.

The ESA dosing system may provide a proven evidence-based assessment of the effectiveness of (or inadequacy of) various dosing regimens or protocols. By means of the ESA dosing system described herein, providers are equipped with a target dosing level heretofore unknown. Other examples of the ESA dosing system may include dosing regimen quality metrics that give providers the data they need to continuously improve their anemia management practices.

National and private insurers are moving for pay for performance reimbursement policies. Other examples of the ESA dosing system may include tools to assist with an objective performance measurement system for the management of anemia.

By resulting in more stable Hgb levels, the ESA dosing system described herein may also decrease the amount of un-reimbursed ESA that has been administered. In sum, the derived therapies may continuously improve patient outcomes, financial performance for providers, and multidisciplinary care team effectiveness.

Experience has shown that providers using rHuEpo are more able to achieve target Hgb values than are providers using darbepoetin alfa. However, rHuEpo alfa may be administered up to three times per week, whereas darbepoetin alfa may be administered weekly, bi-weekly, or even monthly. Providers have attempted to switch to the use of darbepoetin alfa in order to reduce operating costs only to decide at a later time to revert back to darbepoetin alfa due to uncontrolled Hgb cycling. Other examples of the ESA dosing system may include tools to assist providers in transitioning from epoetin alfa to darbepoetin alfa and simultaneously maintaining adequate and stable Hgb values.

Recombinant human erythropoietin (rHuEPO, Epogen, EPO) has a shorter half-life than darbepoetin alfa and is therefore easier to administer. However, dialysis providers utilizing rHuEPO as an ESA must manage and administer rHuEPO at each dialysis session, resulting in increased operational costs, increased risk of infection, and higher turnover on their ESA inventories. Although the techniques are described herein with respect to darbepoetin alfa, it shall be understood that the techniques could be adapted to any form of ESA. The ESA dosing system may be used to assist dialysis providers worldwide in making a successful transition from rHuEPO to darbepoetin alfa and secure the benefits of achieving adequate and stable Hgb values along with the reduced operational costs of less frequent ESA administration.

The successful utilization of the modeling described herein has repercussions that may extend beyond the use of ESAs in patients. For example, the systems, methods, and techniques described herein may be extended to the administration of other drugs with prolonged half-life or extended release formulation. The pharmokinetic studies that are required by the FDA do not provide renal or hepatic function. Likewise, genetically determined differences in drug metabolism are not evident to clinicians until an adverse effect of under- or over-dosing of the drug is noted. The application of this methodology to drug administration may allow faster determination and use of optimal drug dosages, and highlight individual patient differences in the clearance and metabolism of drugs. The current trial and error method of drug administration requires improvement if we are to more safely administer drugs in a patient population with increasing incidence of kidney and liver disease, and increasing utilization of drugs with longer half-lives.

The example ESA dosing model described with respect to FIG. 5 is directed for purposes of illustration to determining dosing of the ESA darbepoetin alfa (Aranesp®). However, as mentioned above, the ESA dosing techniques described herein may also be used to determine patient-specific ESA dosing for any available ESA therapy. These ESAs may include, but are not limited to, Erythropoietin; Epoetin alpha (Procrit®, Epogen®, Eprex®); Epoetin beta; darbepoetin alpha (Aranesp®); Methoxy polyethylene glycol-epoetin beta; Dynepo; Shanpoeitin; Zyrop; Betapoietin; and others.

In addition, the ESA dosing techniques described herein may also be applicable to a wide variety of patient populations, including, for example, ESRD patients, CDK patients, cancer therapy patients, HIV patients, or any other patient population having insufficient hemoglobin production that may benefit from ESA treatment. In addition, the ESA dosing techniques described herein may also be applicable to multiple modes of ESA therapy delivery, including intravenous (IV) delivery, subcutaneous delivery, oral delivery, biopump, implantable drug delivery devices, etc.

FIGS. 20-35 illustrate another example ESA dosing system 1240 and the techniques implemented therein which may be used to determine dosing of ESA therapies. In the examples, the ESA dosing system 1240 is described with respect to darbepoetin alfa (Aranesp®) or epoetin alfa (Epoge"®). However, it shall be understood that the example ESA dosing system may also be used to determine dosing of other ESA therapies.

Figure 20:
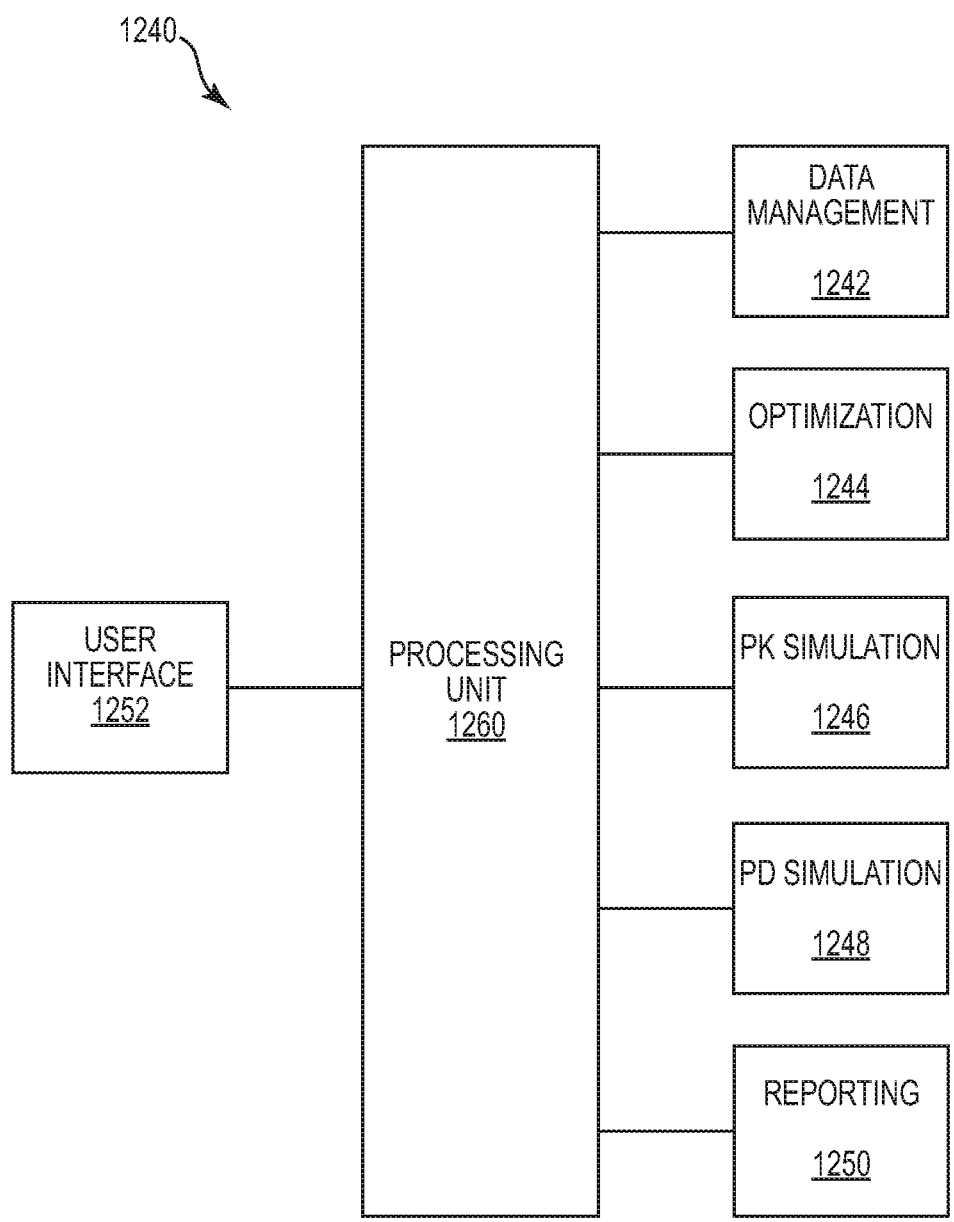
FIG. 20 is a block diagram of another example ESA dosing system.

FIG. 20 is a block diagram of an example ESA dosing system 1240. ESA dosing system 1240 is similar in many respects to ESA dosing system 10 shown in FIG. 1. System 1240 includes a processing unit 1260 and an assortment of data processing and management software modules. For example, ESA dosing system 1240 includes several component software modules: a data management module 1242, an optimization module 1244, a pharmacokinetics (PK) simulation/modeling module 1246, a pharmacodynamics (PD) simulation/modeling module 1248, and a reporting module 1250. Data management module 1242 is concerned with getting data in and out of the system. Optimization module 1244 is concerned with determination of the patient-specific parameters which cause the model to simulate patient-specific erythropoietic responses to ESA therapy. The PK simulation module 1246 models and simulates the effect of the body on the drug, e.g., absorption, metabolism, and elimination. The PD simulation module 1248 models and simulates the effect the drug on the body, e.g., apoptosis sparing. Reporting module 1250 is concerned with presenting the results of the simulation in the form of reports, graphs, and/or other output in a way that is meaningful for an analyst or provider.

Figure 21:
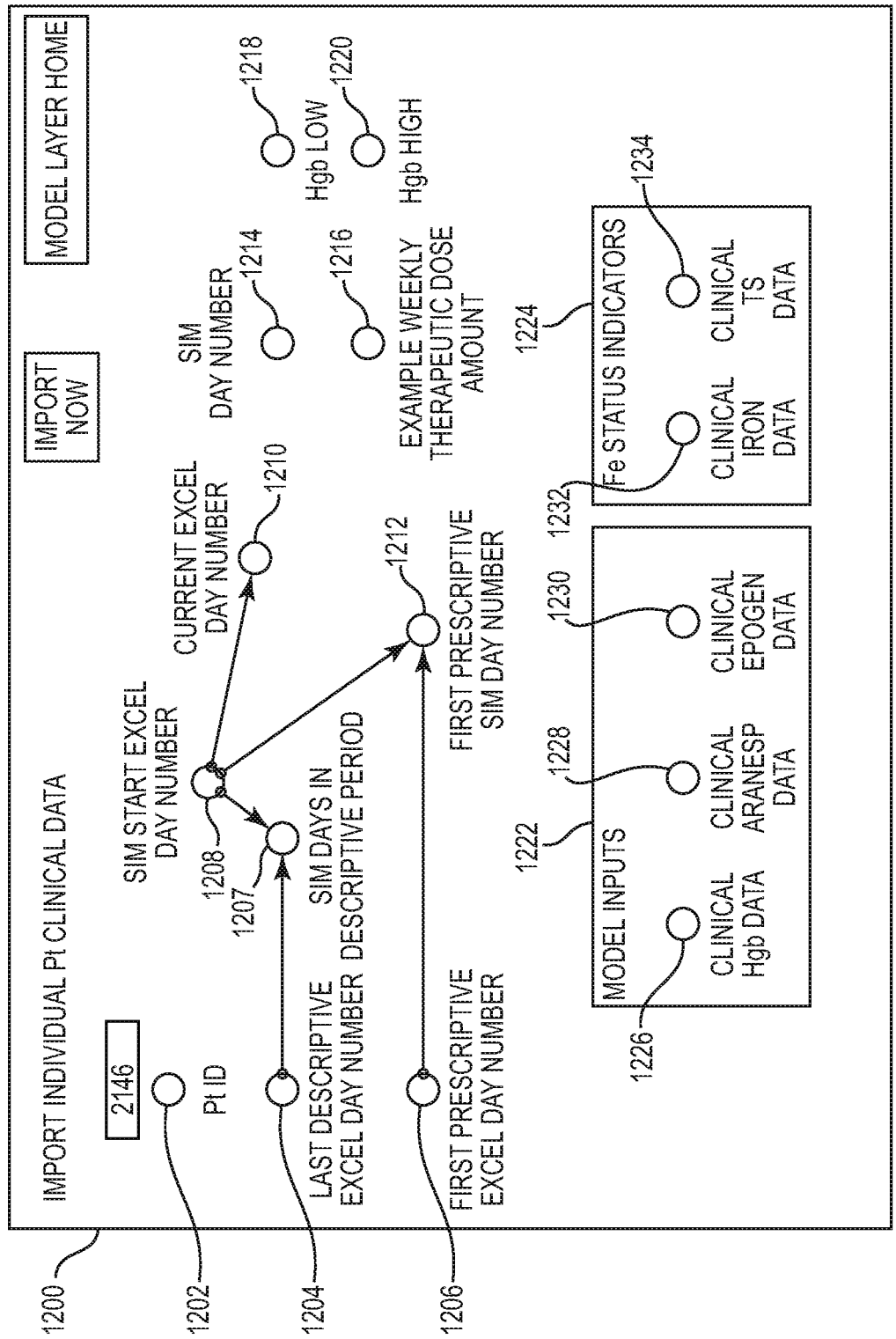
FIG. 21 illustrates an example diagram illustrating part of the data acquisition/management component of the ESA dosing system.

FIG. 21 illustrates an example diagram 1200 that is part of the data acquisition/management component of the ESA dosing system. Diagram 1200 illustrates importation of the historical individual patient data. Pt ID 1202 represents the patient identification number. The top left portion of the diagram 1200 receives the calendar dates concerning the historical data and maps the simulation day numbers to the actual calendar days of the descriptive and prescriptive periods (e.g., simulation day 476 may be equivalent to Dec. 4, 2009, simulation day 477 would then be Dec. 5, 2009, etc.). Last descriptive day number 1204 represents the final calendar day of the descriptive period and First prescriptive day number 1206 represents the first calendar day on which an ESA dose may be administered. (The descriptive period is historical and is used to determine the most likely patient response to future ESA therapy. The prescriptive period is a projection for the future which is developed based upon analysis of the patient's historical response to ESA therapy.) SimDays in descriptive period 1207 is the total number of days in the descriptive period; that is, the total number of days for which historical data will be entered into the model. Sim Start Day Number 1208 is the day number that the descriptive period is to start. In the examples given herein, this day has been designated Day 0. First Prescriptive Sim Day number 1212 is the day number corresponding to the calendar day of the First prescriptive day number 1206 and is the first day on which a patient may receive an ESA dose. Current day number 1210 represents the current day number of the overall simulation as it progresses from day −200 to the last day of the simulation. Weekly Therapeutic Dose 1216 may allow the WTD determined from the model described above with respect to FIG. 5 to be compared with the results of the model described below with respect to FIGS. 32 and 33, if desired.

Model inputs 1222 represent the patient historical hemoglobin data 1226 and the patient historical ESA dosage data to be entered into the model. In this example, the historical ESA data may include either historical Aranesp data 1228 or historical Epogen data 1230, depending upon the ESA therapy used by the particular patient. Other ESA dosage data may also be entered, and the disclosure is not limited in this respect.

Fe (iron) status indicators 1224 represent the patient historical iron data 1232 and/or the patient historical transferrin saturation data, if any, to be entered into the model. This allows the user to take the patient's iron levels into account when running the ESA dosage simulation. Patients who are iron deficient, indicated in part be a transferrin saturation value below 20 percent, may not have enough iron in the blood to combine with mature reticulocytes produced by the bone marrow to create a sufficient number of mature red blood cells containing hemoglobin. If the simulation is not able to fit the historical data, the Fe status indicators 1224 may help the user to better interpret the patient's clinical status and define corrective therapies.

Hgb low 1218 and Hgb high 1220 represent the low and high values of the desired hemoglobin range. For example, the Centers for Medicare & Medicaid Services (CMS) and National Kidney Foundation (NKF) have established the target range for Hgb values among ESRD patients to be between 10 g/dL and 12 g/dL. These or other hemoglobin values appropriate for the patient or the patient's condition may be entered as the low and high hemoglobin values, respectively.

Figure 22:
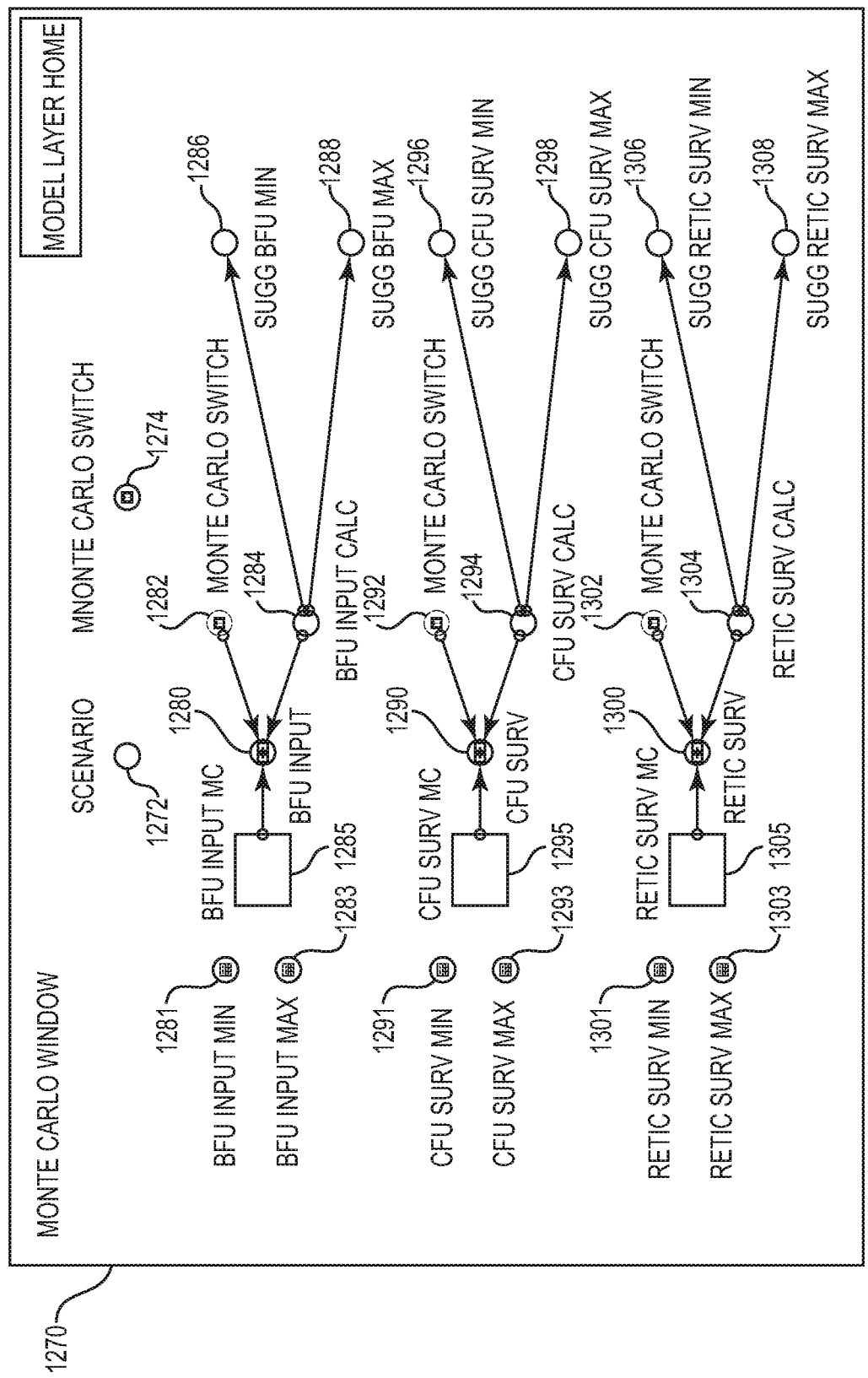
FIGS. 22 and 23 are diagrams illustrating a setup for an example Monte Carlo simulation that determines the best fit patient-specific parameter values for the patient's historical hemoglobin data.
Figure 23:
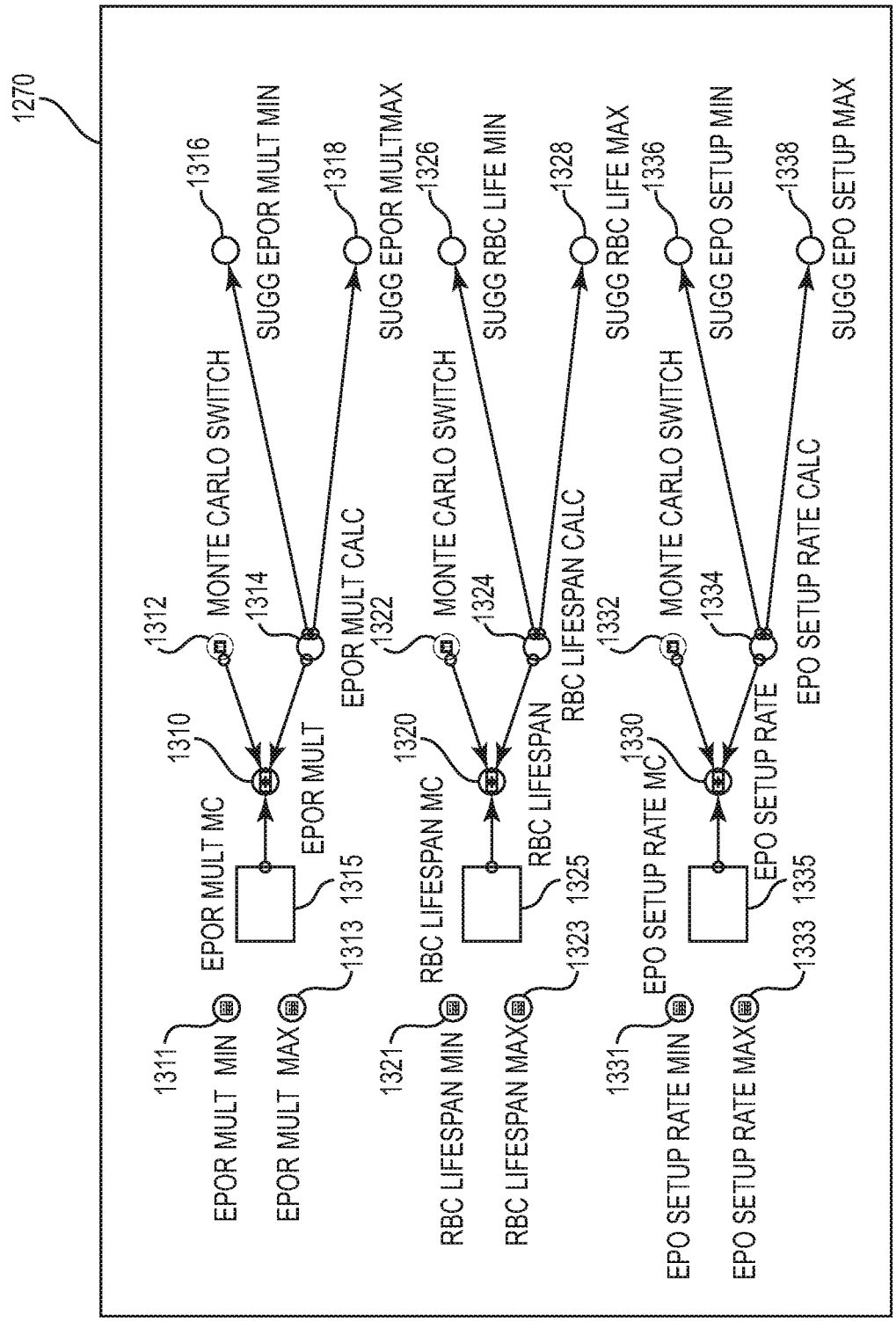

As described above, the biophysical simulation may employ an adaptation of the Monte Carlo method to estimate patient-specific parameter values. It shall be understood that other optimization routines may be employed, and the disclosure is not limited in this respect. FIGS. 22 and 23 are diagrams illustrating a setup for an example Monte Carlo simulation that determines the best fit patient-specific parameter values for the patient's historical hemoglobin data. In this example ESA dosing model, one or more parameters representing various parameters of the patient's red blood cell production chain may be used. These may include, for example, one or more of the following six patient-specific parameters:

Blast Forming Unit Input (BFU INPUT): the number of erythroid burst forming units entering the erythropoietic process each day.

Colony Forming Unit Survival (CFU SURV): the fraction of colony forming units that survive apoptosis in the absence of an ESA.

Reticulocyte Survival (RETIC SURV): the fraction of reticulocytes that survive reticulocyte atrophy, which may be caused by a deficiency in hemoglobin building blocks such as iron, folate, or vitamin B12, among others.

Erythropoietin Receptor (EpoR) Multiplier (EPOR MULT): the value by which Kd is amplified to generate a response within the developing RBC cell a strong enough reaction to prevent apoptosis.

Red Blood Cell Lifespan (RBC LIFESPAN): average lifespan (in days) of a red blood cell.

Erythropoietin Setup Rate (EPO SETUP RATE): a mathematical value applied during the setup period that raises the simulated hemoglobin to a level equal to the observed hemoglobin on the first day of the descriptive period.

For each of the six parameters shown in FIGS. 22 and 23, a Monte Carlo switch 1282, 1292, 1302, 1312, 1322 and 1332 determines whether a user selected value, a previously determined parameter value obtained from a previous Monte Carlo run, or a randomly generated value will be used for each simulation. If the Monte Carlo switch for a particular parameter is turned off, the simulation will take the value of that parameter from a corresponding user selected value or from a previously determined parameter value obtained from previous Monte Carlo run. These user selected values may be input via any suitable user interface, for example via sliders 1602, 1604, 1606, 1608, 1610, and 1612 shown in FIG. 34. This may permit the user to manually control one or more of the parameter values in order to obtain a better fit to the historical hemoglobin data.

If the Monte Carlo switch for a particular parameter is turned on, the simulation will obtain the value of that parameter for each run of the Monte Carlo simulation via a random number generator as described below.

For each of the six parameters shown in FIGS. 22 and 23, MIN 1281, 1291, 1301, 1311, 1321, and 1331 and MAX 1283, 1293, 1303 1313, 1323, and 1333, represent the ranges from which the randomly generated parameter values are to be drawn for the individual simulations of a Monte Carlo simulation. For example, BFU INPUT MIN 1281 and BFU INPUT MAX 1283 are the minimum and maximum values, respectively, from which the random numbers to be used for each run of the Monte Carlo simulation for the parameter BFU INPUT are to be drawn.

For each parameter, MC 1285, 1295, 1305, 1315, 1325, and 1335, represents a function that generates a random number between the values of MIN and MAX for each run of the Monte Carlo simulation. For example, BFU INPUT MC 1285 represents a function that generates a random number between the values of BFU INPUT MIN 1281 and BFU INPUT MAX 1283 for each run of the Monte Carlo simulation.

BFU INPUT 1280, CFU SURV 1290, RETIC SURV 1300, EPOR MULT 1310, RBC LIFESPAN 1320 and EPO SETUP RATE 1330 are either the previously determined parameter value obtained from a Monte Carlo run or user selected parameter values (input, for example, via sliders shown in FIG. 34 as described above when those sliders are set to a mode to override previously obtained parameter values) used when the Monte Carlo switch is turned off for the corresponding parameter.

BFU INPUT CALC 1284, CFU SURV CALC 1294, RETIC SURV CALC 1304, EPOR MULT CALC 1314, RBC LIFESPAN CALC 1324, EPO SETUP RATE CALC 1334 are the values obtained from the best fit run of a Monte Carlo simulation. Once the best fit run is determined, the parameter values determined from that best fit run may be used to determine a therapeutic dose that may be administered in the prescriptive period. A therapeutic dose of an ESA is that dose which causes a patient's hemoglobin values to achieve and sustain the target hemoglobin value as long as the patient's clinical condition remains stable. However, the user may want to attempt to improve upon the initially obtained best fit results by manually selecting a value for one or more of the parameters (such as via the sliders shown in FIG. 34) and running additional simulations. Alternatively or in addition, the user may attempt to improve upon the initial or intermediate best fit results by narrowing the range from which the random numbers are generated by adjusting the MIN and MAX values (such as BFU INPUT MIN 1281 and/or BFU INPUT MAX 1283, CFU SURV MIN 1291 and/or CFU SURV MAX 1293, etc.) for one or more parameters. Suggested values for narrowed parameter ranges may be supplied by 1286, 1288, 1296,1298, 1306, 1308, 1316,1318, 1326, 1328, 1336, an 1338 on FIGS. 22-23.

Suggested BFU minimum (Sugg BFU min) 1286 and Suggested BFU maximum (Sugg BFR max) 1288, Sugg CFU surv min 1296 and Sugg CFU surv max 1298, sugg retic surv min 1306 and sugg retic surv max 1308, sugg EPOR mult min 1316 and sugg EPOR mult max 1318, sugg RBC LIFE 1326 and sugg RBC LIFE 1328, and sugg EPO setup min 1336 and sugg EPO setup min and sugg EPO setup max 1340 may be the results obtained from a Monte Carlo run. Should the user choose to perform a subsequent Monte Carlo run, these values may be the suggested values to use for the respective minimum and maximum values to use as lower and upper bounds from which random values will be drawn in the subsequent Monte Carlo run.

Figure 24:
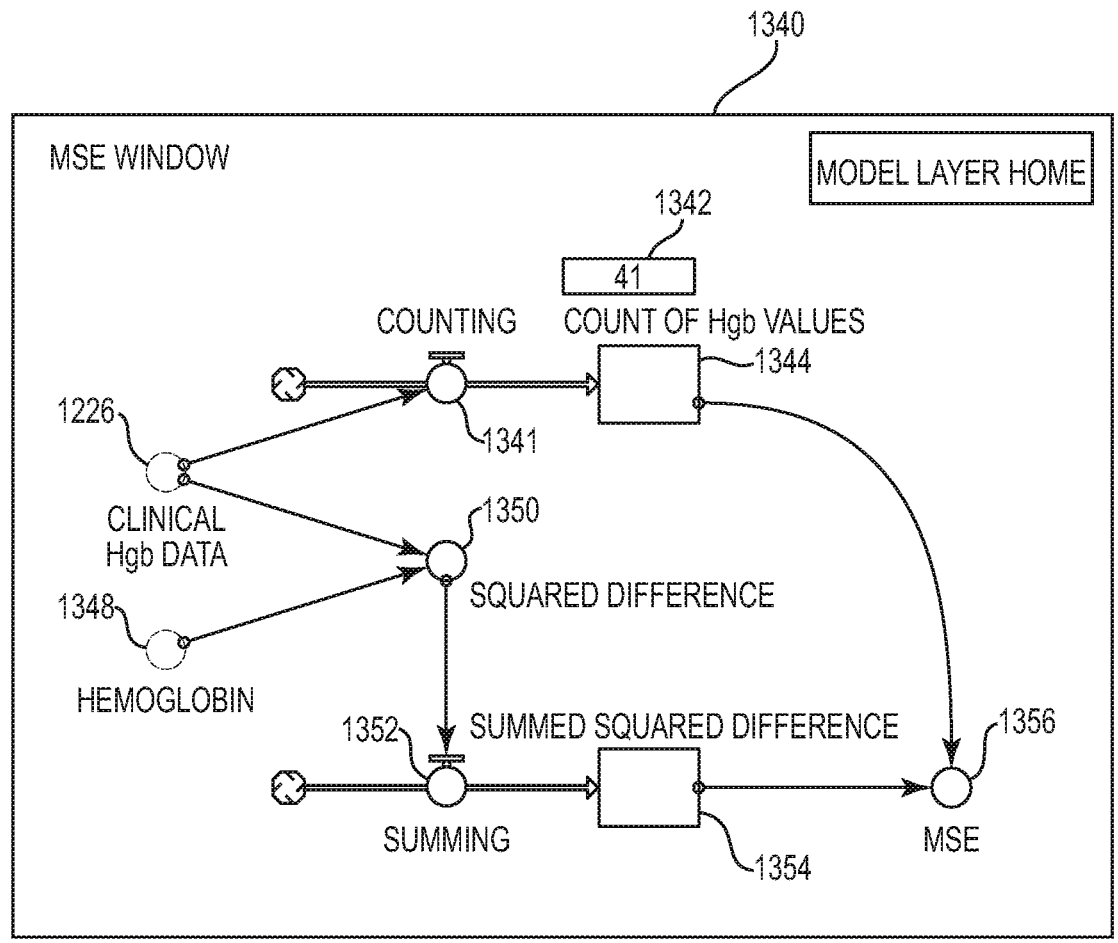
FIG. 24 is a diagram representing an example calculation of a mean square error (MSE) for one run of the Monte Carlo simulation.

FIG. 24 is a diagram 1340 representing an example calculation of a mean square error (MSE) for one run of the Monte Carlo simulation. In this example, the MSE of each run of the Monte Carlo simulation is used to determine goodness of fit of the simulated hemoglobin and the observed hemoglobin values of the descriptive period. The run with the lowest MSE, drawn from, for example, 100 individual simulations may be determined to be the best fit run. However, other methods of minimizing MSE may also be used, and the disclosure is not limited in this respect.

To determine the MSE for each run, the total number of hemoglobin values in the descriptive period is counted (1341, 1344). The squared difference of the simulated hemoglobin 1348 and the patient specific historical Hgb data 1226 is determined (1350). The squared differences are summed over all days of the descriptive period (1352, 1354). The MSE 1356 is the sum of the squares divided by the total number of hemoglobin values in the descriptive period 1344 (displayed in this example in box 1342). The MSE for each run is determined, and the run with the lowest MSE is determined to be the "best fit run."

Figure 25:
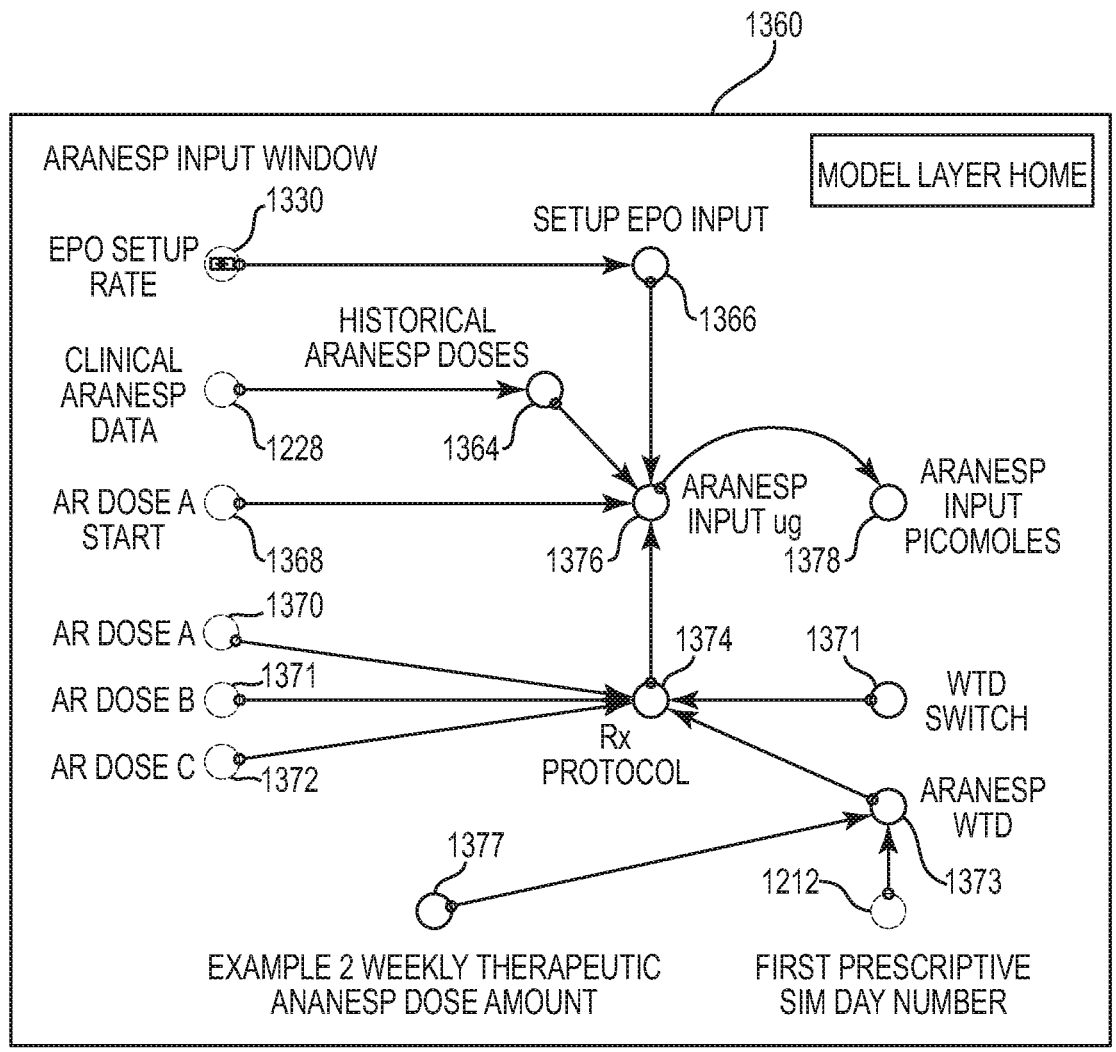
FIG. 25 is a diagram representing an example amount of Aranesp administered at a prescribed interval based on a prescription regimen equivalent to a simulated therapeutic dose.

FIG. 25 is a diagram 1360 representing the amount of Aranesp administered at a prescribed interval based on a prescription regimen equivalent to a simulated therapeutic dose. For example, a therapeutic Aranesp dose for a patient might be determined to be 32 mcg per week. The equivalent Aranesp dosing regimen, a titration of available dose amounts might be 25 mcg in week 1 followed by 40 mcg in week 2, the 25 mcg 1 week later and so on. Although this example is described with respect to Aranesp, it shall be understood that this model may also be applicable to other ESA therapies that require similar methods of titration based upon their respective PK parameters, Kd, and/or half life.

EPO SETUP RATE 1330 is one of the patient-specific parameters to be determined during the simulation. CLINICAL ARANESP DATA 1228 is the patient-specific historical Aranesp dosage data during the descriptive period. In this example, a recommended dosing regimen for Aranesp is divided into three separate doses to be administered on given days, dose A 1370, dose B 1371, and dose C 1372, to deliver the equivalent of the weekly therapeutic dose (WTD) determined by the simulation. Dose A START 1368 is the earliest day on which dose A may be given, as well as the day on which Dose A is to commence. ARANESP INPUT (micrograms) 1376 is a the total dose on a given day of the simulation from all sources: EPO setup rate 1330, Clinical Aranesp Data 1364, and Rx Protocol 1374. Rx Protocol 1374 can be of two types, it is either the sum of Aranesp dose A 1370, Aranesp dose B 1371, and Aranesp dose C 1372 or, it is Aranesp WTD 1373, depending on the value of WTD Switch 1371. Aranesp WTD 1373 is equal to the value of Example 2 Weekly Therapeutic Aranesp Dose Amount 1377, which is a user-entered dose, to be applied in the simulation beginning on First Prescriptive Sim Day Number 1212 (see FIG. 21) and on every subsequent seventh day of the simulation. Once patient parameters have been found, simulation experiments with different values of Example 2 Weekly Therapeutic Dose Amount 1377 may enable the user to identify the value of the weekly therapeutic Aranesp dose that will achieve and sustain the desired hemoglobin level for this patient. Aranesp input (picomoles) 1378 is a numerical conversion that converts the dosage in micrograms per dose to picomoles per dose, regardless of the source of the dose: setup, historical, WTD, or recommended dosing regimen. Alternatively, rather than permitting or requiring user input, these and other components of the model may be implemented via an automated software system.

Figure 26:
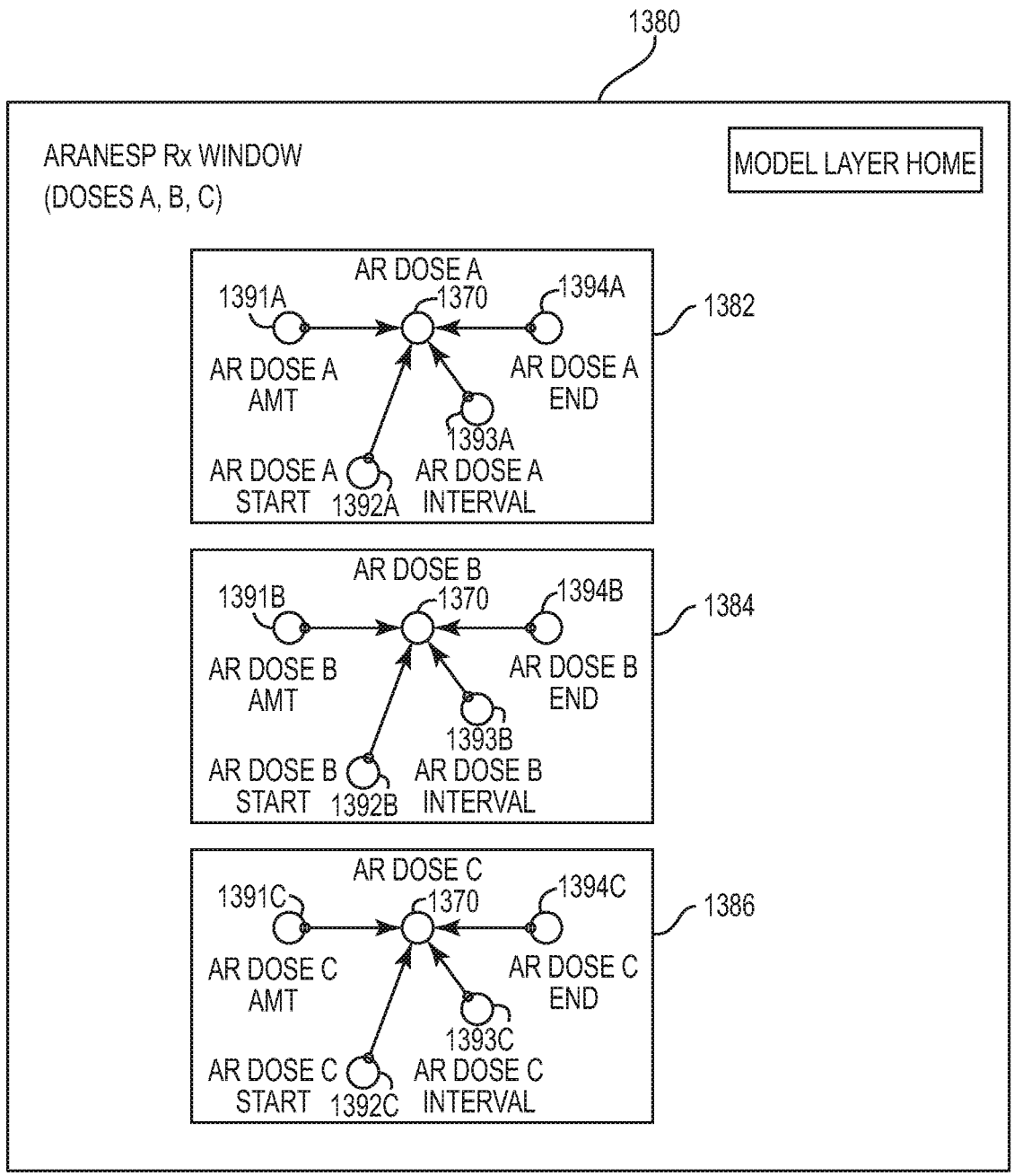
FIG. 26 is a diagram representing one possible example set of variables which may be used to define a recommended Aranesp prescription regimen.

FIG. 26 is a diagram 1380 representing one possible set of variables which may be used to define a recommended Aranesp prescription regimen. Although this diagram is described with respect to Aranesp, it may also be applicable to other ESA therapies. Diagram 1382 represents the factors that determine Aranesp dose A 1370, diagram 1384 represents the factors that determine Aranesp dose B 1371, and diagram 1386 represents the factors that determine Aranesp dose C 1372. For example, dose A, dose B, and dose C each include a dose amt 1391A-1391C, a does start 1392A-1392C, a dose interval 1393A-1393C, and a dose end 1394A-1394C, respectively. This permits the appropriate titration to be determined based on the Aranesp WTD determined by the ESA dosing system. The time periods for dose A, dose B, and/or dose C may or may not overlap, depending upon what is required to obtain the Aranesp WTD determined by the ESA dosing system, as well as any initial corrective doses that might be required by patients entering the prescriptive period with low hemoglobin values.

Figure 27:
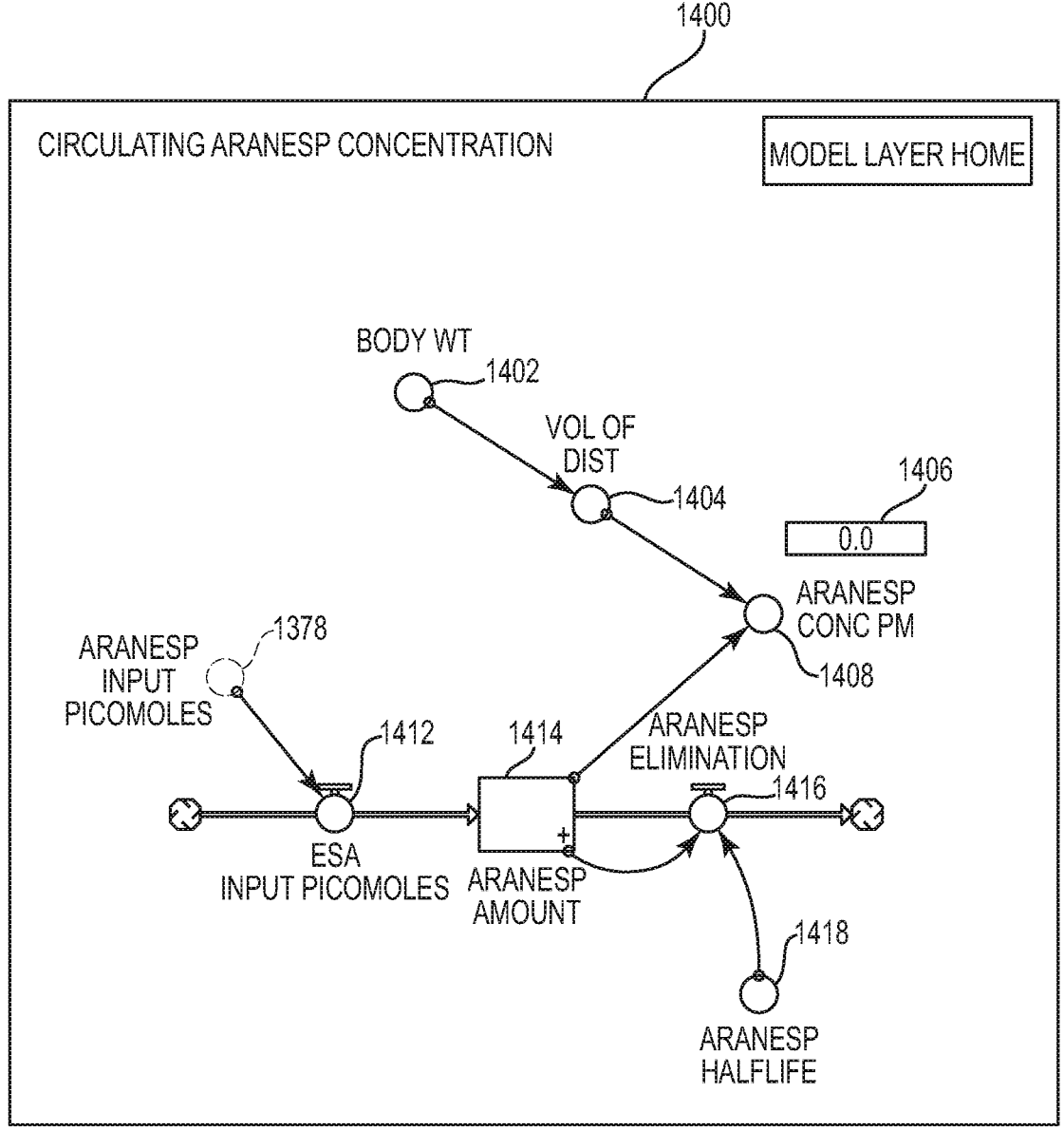
FIG. 27 is a diagram representing an example determination of the circulating Aranesp concentration.

FIG. 27 is a diagram 1400 representing determination of the circulating Aranesp concentration. Again, although this diagram is described with respect to Aranesp, the model is equally applicable to other ESA therapies. An idealized body weight 1402 (e.g., 70 kg) is used to determine an idealized volume of distribution 1404 (the distribution of a medication between plasma and the rest of the body). The patient's actual body weight may be used, if desired. Aranesp input (picomoles) 1378 is the value obtained as described above with respect to FIG. 26 and is input at ESA input moles 1412. The ARANESP AMOUNT 1414 is eliminated from the body as determined by the Aranesp half life 1418. Aranesp elimination 1416 represents a mathematical reduction per day of the ARANESP AMOUNT 1414 based on the Aranesp half life 1418. The reduced Aranesp amount and the volume of distribution 1404 determine the resulting Aranesp concentration (picomoles) 1406.

Figure 28:
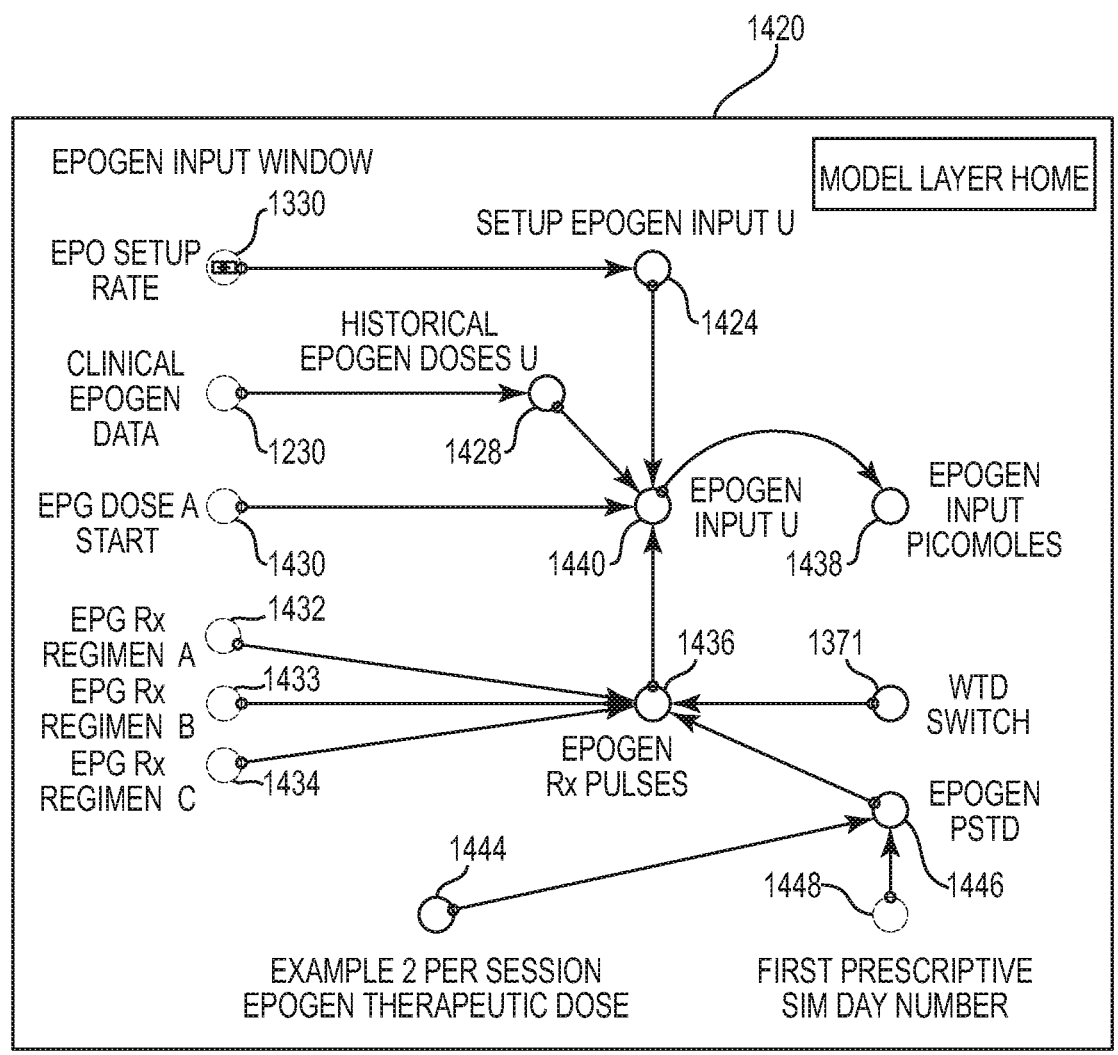
FIG. 28 is a diagram representing an example amount of Epogen administered at a prescribed interval based on a recommended prescription regimen equivalent to a simulated therapeutic dose.

FIG. 28 is a diagram 1420 representing the amount of Epogen administered at a prescribed interval based on a recommended prescription regimen equivalent to a simulated therapeutic dose. Although this example is described with respect to Epogen, it shall be understood that this model may also be applicable to other ESA therapies. Diagram 1420 has the same structure as diagram 1360 of FIG. 25. A similar diagram may thus apply to other ESA therapies. EPO SETUP RATE 1330 is one of the patient-specific parameters to be determined during the simulation. This parameter is input at setup EPO input 1424. CLINICAL EPOGEN DATA 1230 is the patient-specific historical Epogen dosage data during the descriptive period. This data is input at historical Epogen doses 1428. In this example, a recommended dosing regimen for Epogen is divided into three separate doses to be administered on given days, dose A 1432, dose B 1433, and dose C 1434, to arrive at the desired per session therapeutic dose (PSTD) determined by the simulation. Dose A START 1430 is the earliest day on which dose A may be given, as well as the day on which Dose A is to commence. EPOGEN INPUT (units) 1440 is a the total dose on a given day of the simulation from all sources: EPO setup rate 1330, Clinical EPOGEN Data 1426, and Epogen Rx Pulses 1436. Epogen Rx Pulses 1436 can be of two types, it is either the sum of Epg Rx regimen A 1432, Epg Rx regimen B 1433 and Epg Rx regimen C 1434 or, it is Epogen PSTD 1446, depending on the value of WTD Switch 1371. Epogen PSTD 1446 is equal to the value of Example 2 Per Session Epogen Therapeutic Dose 1444, which is a user-entered dose, to be applied in the simulation beginning on First Prescriptive Sim Day Number 1448 and on the day of every subsequent dialysis session of the simulation. (Epogen is typically administered three times per week at each dialysis session;

Aranesp is administered at least weekly, hence the difference in therapeutic dosing conventions. Other ESA's may have differing therapeutic dosing conventions based fundamentally on their respective Kd and half lives.) Once patient parameters have been found, simulated experiments with different values of Example 2 Per Session Epogen Therapeutic Dose 1444 enables the user to identify the value of the PSTD that will achieve and sustain the desired hemoglobin level for this patient. Epogen input (picomoles) 1438 is a numerical conversion that converts the dosage in units per dose to picomoles per dose regardless of the source of the dose: setup, historical, PSTD, or recommended dosing regimen. Alternatively, rather than permitting or requiring user input, these and other components of the model may be implemented via an automated software system.

Figure 29:
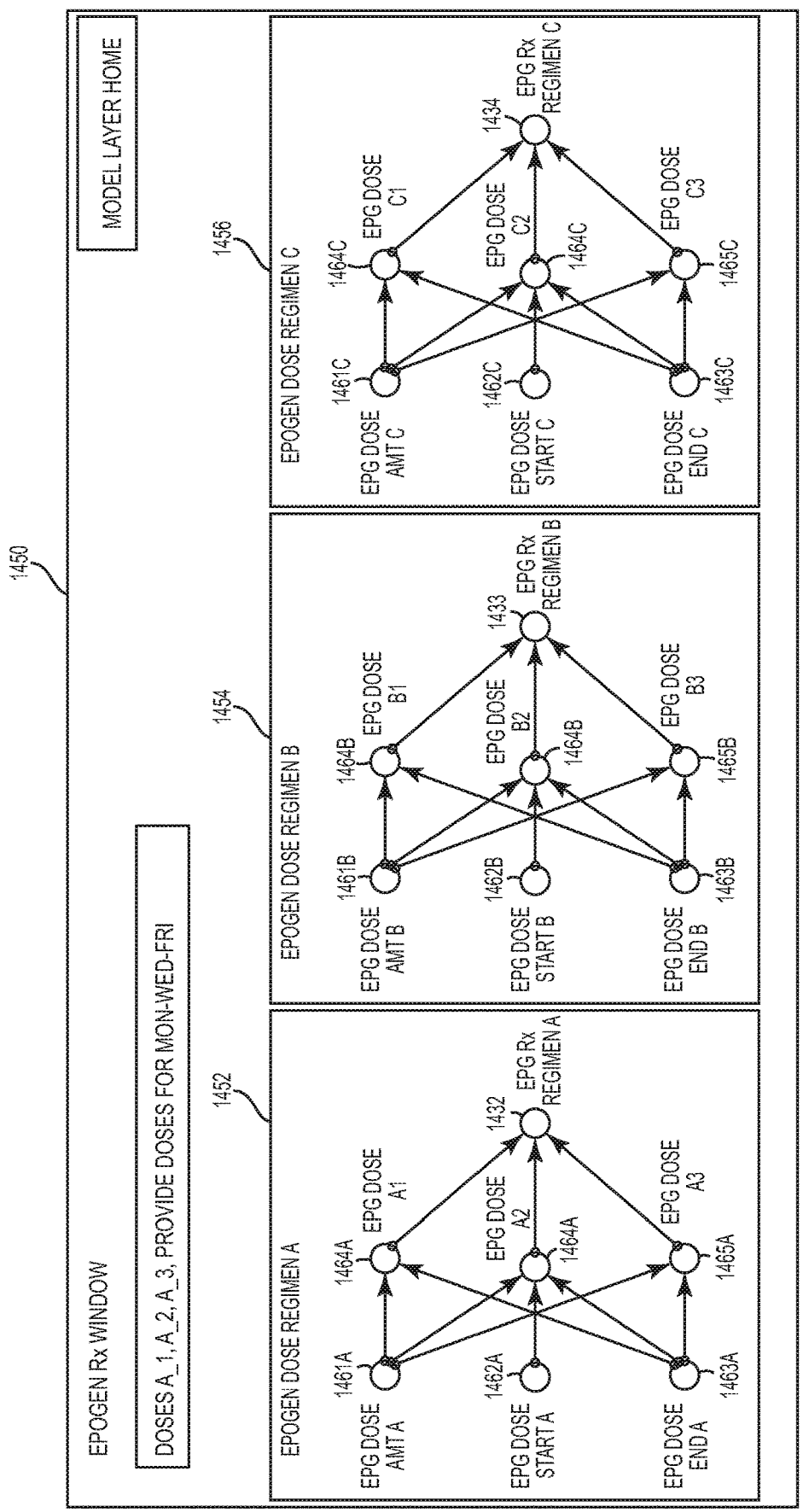
FIG. 29 is a diagram representing one possible set of variables which may be used to define an Epogen prescription regimen.

FIG. 29 is a diagram 1450 representing one possible set of variables which may be used to define an Epogen prescription regimen. Although this diagram is described with respect to Epogen, it may also be applicable to other ESA therapies. In this example, Epogen may be given in up to three different dosages, dose A, dose B and dose C. Diagram 1452 illustrates the factors that determine Epogen dose A 1432, diagram 1454 illustrates the factors that determine Epogen dose B 1433, and diagram 1456 represents the factors that determine Epogen dose C 1434. In this example, doses A, B, and C are scheduled to dose on Monday, Wednesday, and Friday, respectively. For example, dose A, dose B, and dose C each include a dose amt 1461A-1461C, a dose start 1462A-1462C, and a dose end 1463A-1463C, respectively. Epogen dose A1 1464, Epogen dose A2 1465, and Epogen dose A3 1466 permit the user flexibility in setting up customized dosing regimens. However, the same dose could be given each time rather than different doses on different days of the week.

Figure 30:
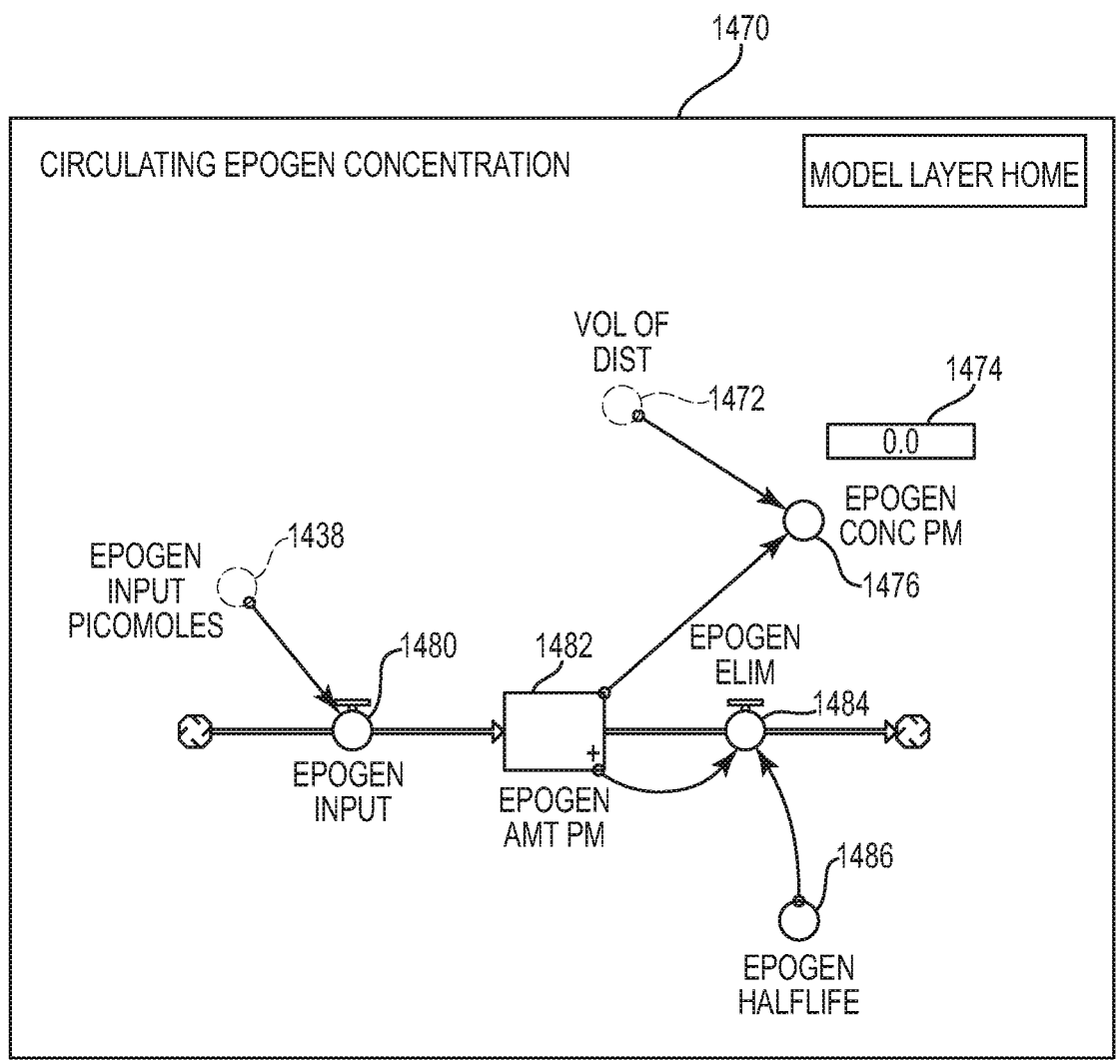
FIG. 30 is a diagram representing an example determination of the circulating Epogen concentration.

FIG. 30 is a diagram 1470 representing determination of the circulating Epogen concentration. This diagram has the same structure as diagram 1400 of FIG. 27. Again, although this diagram is described with respect to Epogen, it may also be applicable to other ESA therapies. An idealized volume of distribution 1472 is entered into the system. Epogen input (picomoles) 1438 is the value obtained as described above with respect to FIG. 28 and is input at Epogen input 1480. The EPOGEN AMOUNT pM 1482 is eliminated from the body as determined by the Epogen half life 1486. Epogen elimination 1484 represents a mathematical reduction per day of the EPOGEN AMOUNT pM 1482 based on the Epogen half life 1486. The reduced Epogen amount and the volume of distribution 1472 determine the resulting Epogen concentration (picomoles) 1476.

Figure 31:
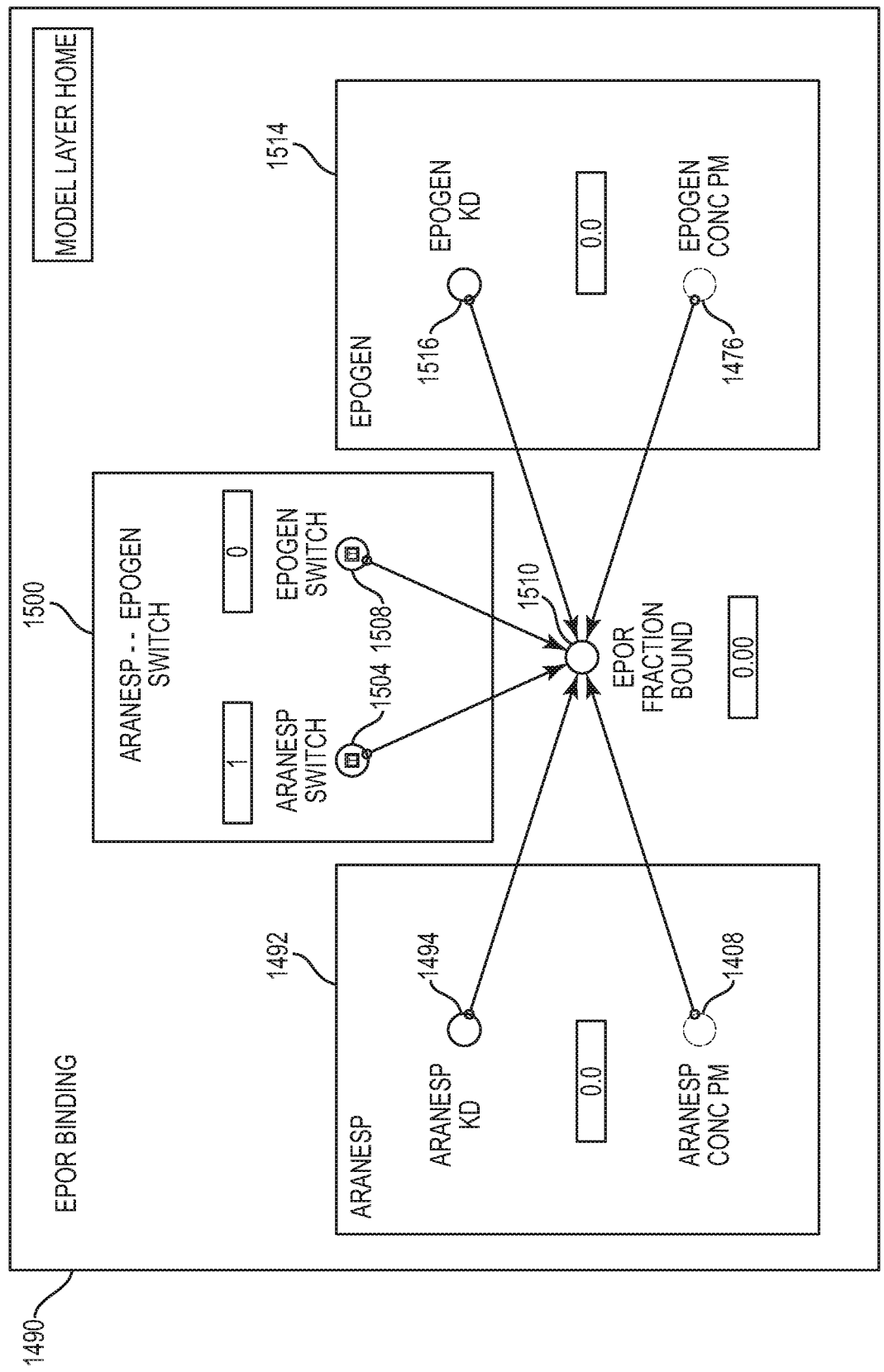
FIG. 31 is a diagram illustrating an example EPOR (erythropoietin receptor) binding for Epogen and Aranesp.

FIG. 31 is a diagram 1490 illustrating EPOR (erythropoietin receptor) binding for Epogen and Aranesp. However, it shall be understood that this diagram may also be applicable to other ESA therapies. If other ESA therapies are to be used, the ESA dosing system may include similar diagrams and functionality corresponding to those other ESA therapies. Diagram 1500 includes an ARANESP switch 1504 and an EPOGEN switch 1508. Switches 1504, 1508 permit a user to select which drug was used by the patient during the descriptive period, and for which a proposed prescription during the prescriptive period should be determined.

A published parameter referred to as the "ESA Kd" is stored by the ESA dosing system and applied in the model. The ESA Kd is a known value for each ESA that may be entered by a user and stored by the system. Kd refers to the dissociation constant of the ESA being used and the erythropoietin receptor (EPOR).

In this example, the ESA Kd values shown in FIG. 31 are the Aranesp Kd 1494 and the Epogen Kd 1516. When the drug at issue is Aranesp, for example, the ESA dosing system combines the Aranesp Kd 1494 and the Aranesp concentration 1408 (determined as shown in FIG. 27) and determines a calculated value referred to as the "EPOR fraction bound" (erythropoietin receptor fraction bound) 1510. Similarly, when the drug at issue is Epogen, the ESA dosing system combines the Epogen Kd 1516 and the Epogen concentration 1476 (determined as shown in FIG. 30) and determines the EPOR fraction bound 1510. A similar calculation may be made when other ESAs are being simulated.

The calculated value "EPOR fraction bound" refers to the percentage of eporeceptors on the surface of BFU-E cells that have bound the ESA being used for therapy. Once a minimum percentage is reached, the rate of programmed cell death (apoptosis) is decreased by means of reactions within the cell in response to bound eporeceptors on the surface of the cell.

For example, if the EPOR fraction bound 1510 is greater than a minimum percentage (such as 10%) then the apoptosis rate decreases. Alternatively, if the EPOR fraction bound 1510 is less than the minimum percentage, the apoptosis rate increases. The effect of the EPOR fraction bound on the apoptosis rate is described in more detail below with respect to FIG. 32.

Figure 32:
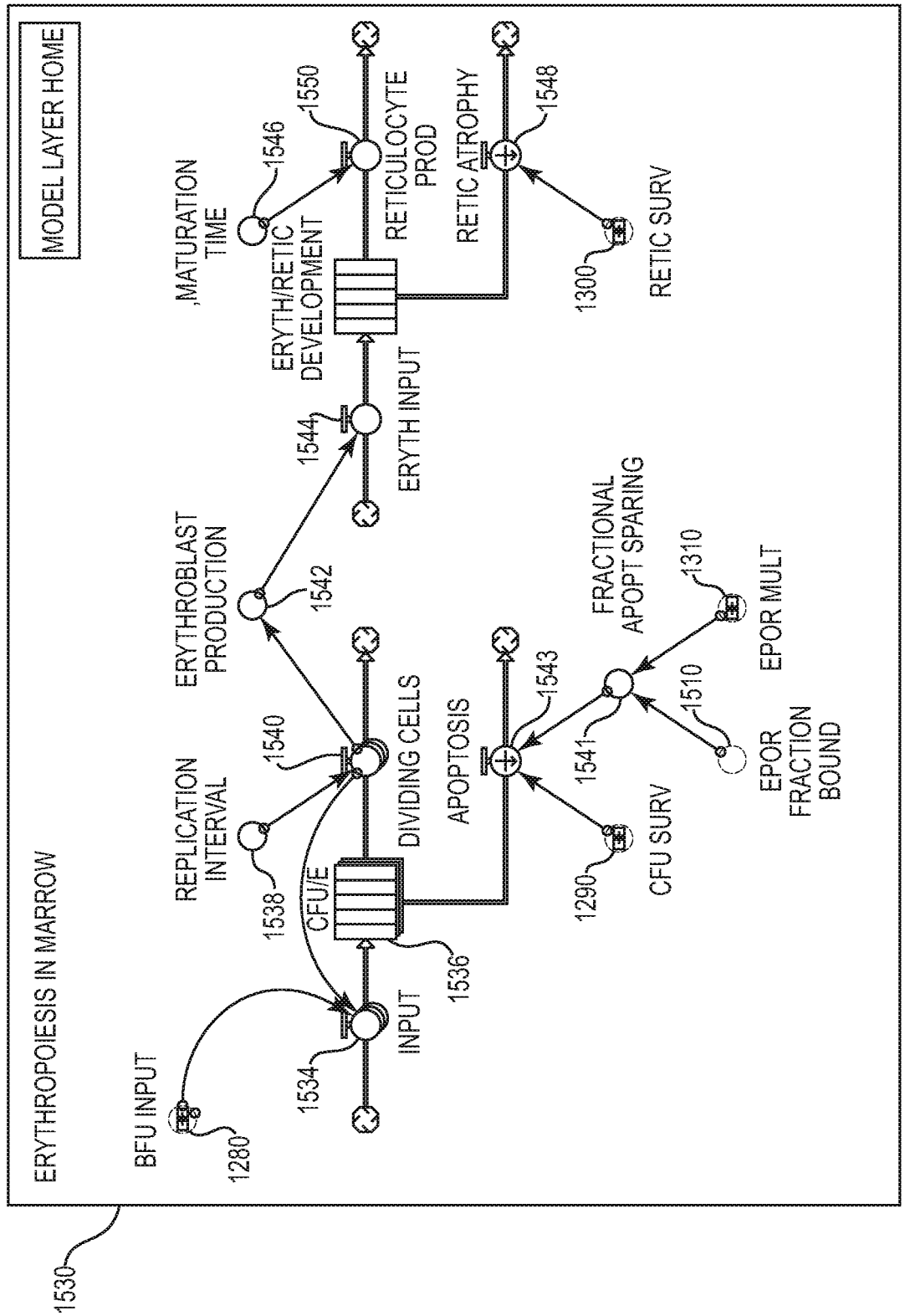
FIG. 32 is a diagram illustrating an example model of reticulocyte production in bone marrow.

FIG. 32 is a diagram 1530 illustrating an example model of reticulocyte production in bone marrow. Diagram 1530 generally represents the pharmacodynamics (PD) component of the model. Diagram 1400 of FIG. 27 and diagram 1470 of FIG. 30 generally represent the pharmacokinetics (PK) component of the model. The patient-specific parameters that enter into Erythropoiesis in Marrow 1530 of the ESA dosing model may include, for example, BFU input 1280, CFU Survival 1290, EpoR multiplier 1310, and Reticulocyte Survival 1300.

CFU/E chain 1536 represents cell replication that occurs through a number of generations. The number of generations considered by the model may vary in a specified range; for example, from 12 to 31 generations. BFU INPUT 1280 is the number of blast forming units committed to forming red blood cells which is input into model at 1534. Due to cellular division, the input of each successive generation in the CFU/E chain 1536 is twice the output of the previous generation. A replication interval 1538 describes the length of time required for each generation to replicate. For example, the replication interval may be in the range of 0.75 to 1.25 days, or other appropriate interval. CFU/E cells are the cells within the erythrocyte lineage that are subject to apoptosis and responsive to apoptosis-sparing ESA therapy. The total number of cells within CFU/E chain 1536 is reduced by apoptosis 1543, as moderated by the ESA concentration. CFU Survival 1290 is a patient-specific parameter defined as the fraction of colony forming units that survive apoptosis in the absence of an ESA. EPOR fraction bound 1510 and EPOR multiplier 1310 determine the fractional amount of apoptosis sparing 1541 in the presence of an ESA. This lowers the rate of apoptosis 1543, increasing the number of dividing cells 1540 that survive apoptosis and go on to become erythroblasts 1542, and eventually, erythrocytes.

Erythroblast/Reticulocyte development chain 1544 represents maturation of the number of erythroblasts that survived apoptosis 1542, 1544. A maturation time 1546 describes the length of time required for each generation of erythroblasts to mature. For example, maturation time may be in the range of 3 to 5 days, or other appropriate maturation time. The total number of reticulocytes leaving development chain 1544 is reduced by reticulocyte atrophy 1548. Reticulocyte atrophy 1548 is determined by the patient-specific parameter Reticulocyte Survival 1300, defined as the fraction of reticulocytes successfully mature in the presence of required complementary materials, such as iron, folate, and B12, for example. Reticulocyte survival is also influenced by infection and inflammation. In the case of infection, bacteria compete with the maturing cells for iron, reducing the iron available to form hemoglobin in the maturing cell. In the case of inflammation, available iron is sequestered, effectively reducing iron availability to the maturing cell. In the current embodiment of ESA Dosing System 1240, assessments on the status of complementary materials, inflammation, and infection are made by an expert model user. The ESA dosing model may include software algorithms to simulate the status of complementary materials, inflammation, and infection in regard to reticulocyte survival, and the disclosure is not limited in this respect. The number of maturing cells that survive reticulocyte atrophy is the number of reticulocytes 1550 produced by the bone marrow.

Figure 33:
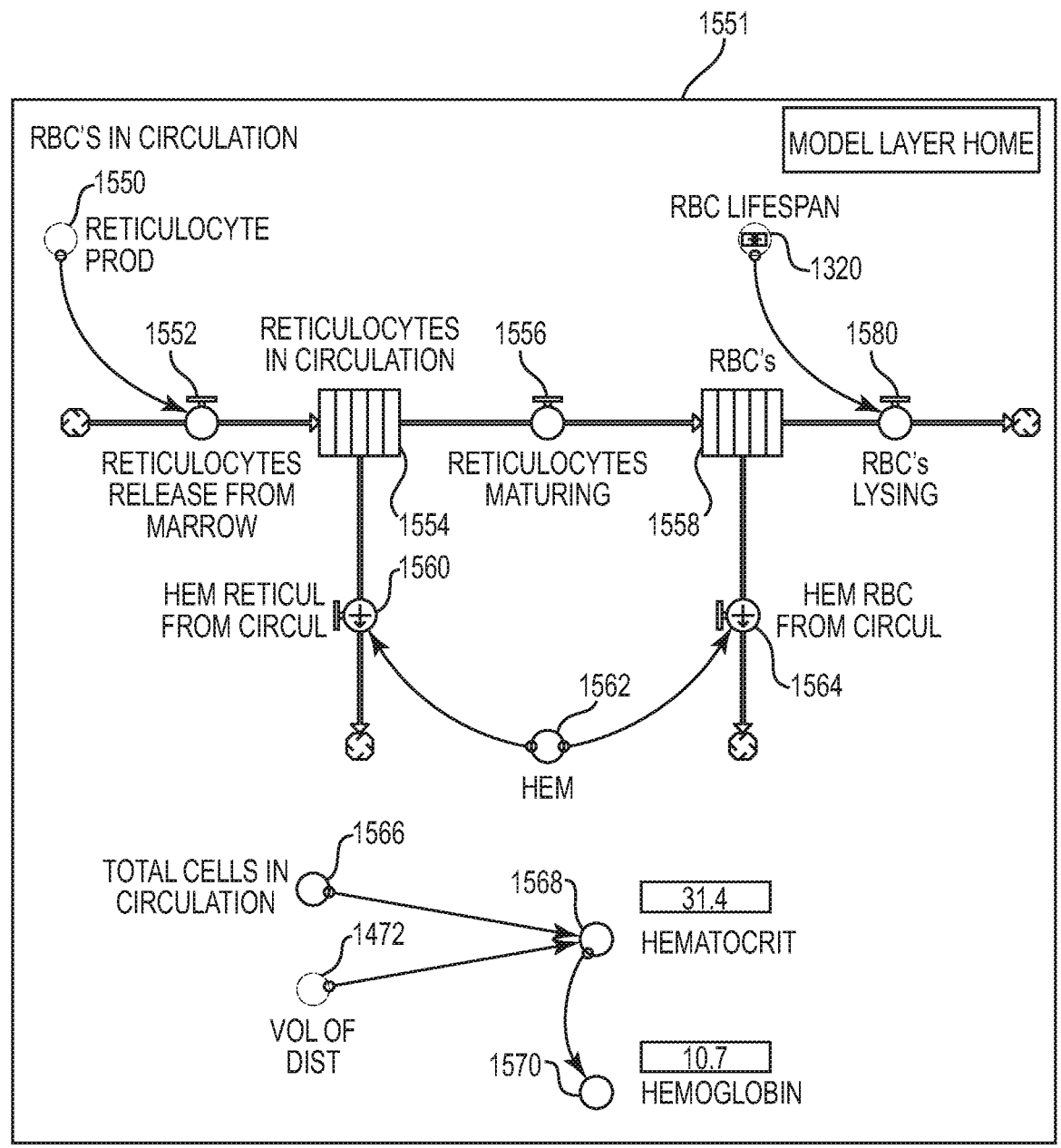
FIG. 33 is a diagram is an example model that simulates the total number of red blood cells in circulation.

FIG. 33 is a diagram 1551 is an example model to simulate the total number of red blood cells in circulation. Reticulocyte production 1550 (determined as described above with respect to FIG. 32) enters into reticulocytes in circulation chain 1554. HEM 1562 is information concerning hemorrhages (blood loss for any reason) experienced by the patient. A hemorrhage reduces the number of reticulocytes in circulation and the number of red blood cells (RBCs) in circulation, and therefore hemoglobin. These hemorrhage reduction effects are represented by hemorrhage reticulocyte reduction from circulation 1560 (expressed, for example, as a fraction) and hemorrhage RBC reduction from circulation 1564 (also expressed, for example, as a fraction). The number of reticulocytes maturing 1556 enters into the RBC chain 1558. The number of RBCs leaving the RBC chain 1558 is reduced by any hemorrhage effects (1564). The total number of mature RBCs is influenced by the patient-specific parameter RBC Lifespan 1320, defined as the average lifespan (in days) of a red blood cell. The total number of RBCs in circulation is represented by total cells in circulation 1566 which is the sum of reticulocytes in circulation 1554 and RBC's 1558.

The total cells in circulation 1566 (reticulocytes in circulation+RBCs in circulation) together with the volume of distribution 1472 gives the simulated hematocrit 1568. The hematocrit multiplied by a constant gives the simulated hemoglobin 1570.

Figure 34:
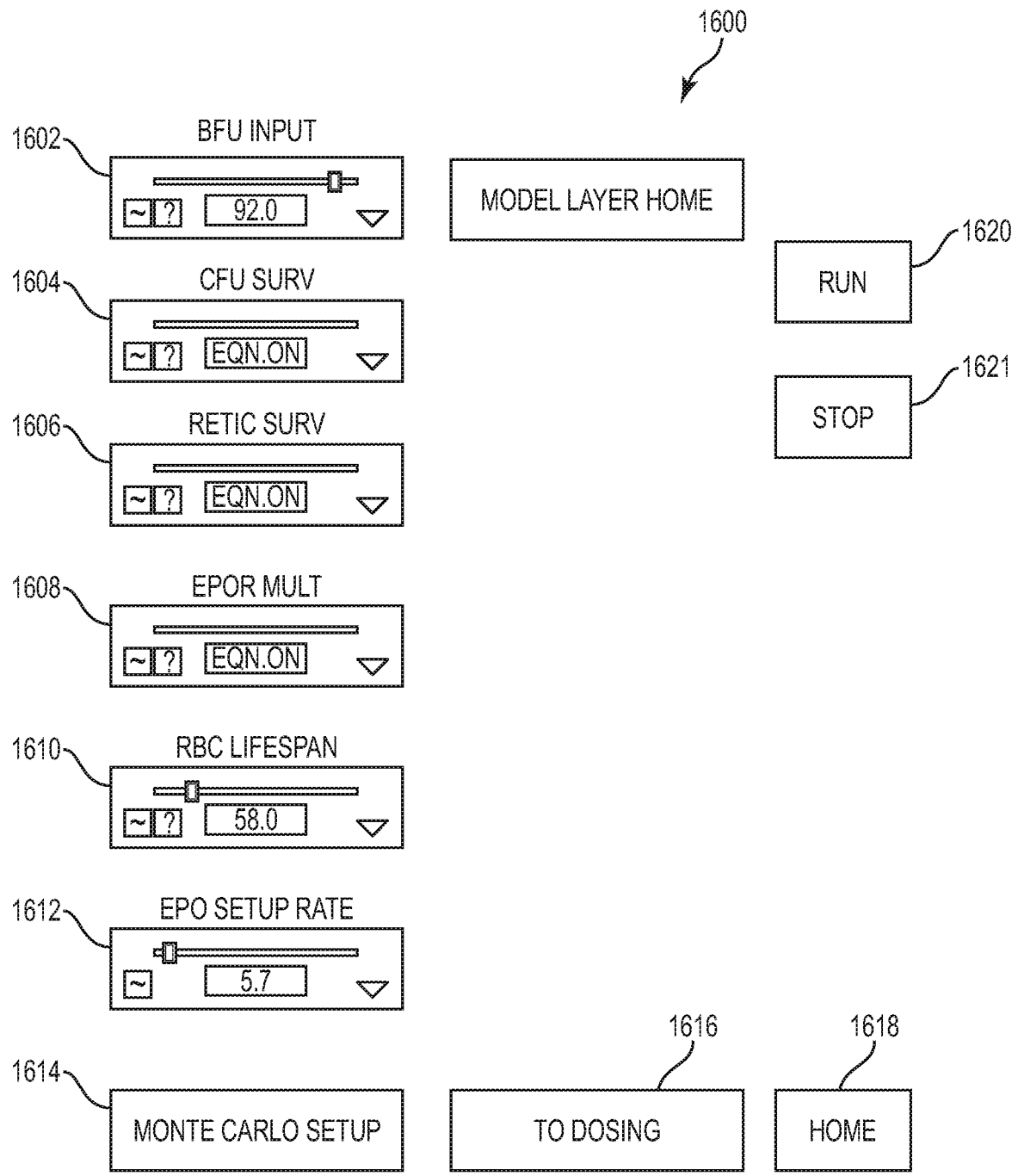
FIG. 34 is an example user interface through which a user may interact with and/or control various aspects of the ESA dosing system.

FIG. 34 is an example user interface 1600 through which a user may control various aspects of the ESA dosing system, enter various parameter values, run and control simulations, etc. These user selected patient-specific parameter values may be input via sliders 1602, 1604, 1606, 1608, 1610, and 1612 for one or more of the patient-specific parameter values. Button 1614 takes the user to a Monte Carlo setup screen, button 1616 takes the user to an ESA dosing screen, button 1618 takes the user to a home screen, buttons 1620 allow the user to run a simulation, and button 1621 allows the user to stop a simulation. It shall be understood that this disclosure is not limited to the specific example methods of navigation among the various elements of the simulation model described herein, as other methods may be used alternatively or in addition to the methods described herein.

Figure 35:
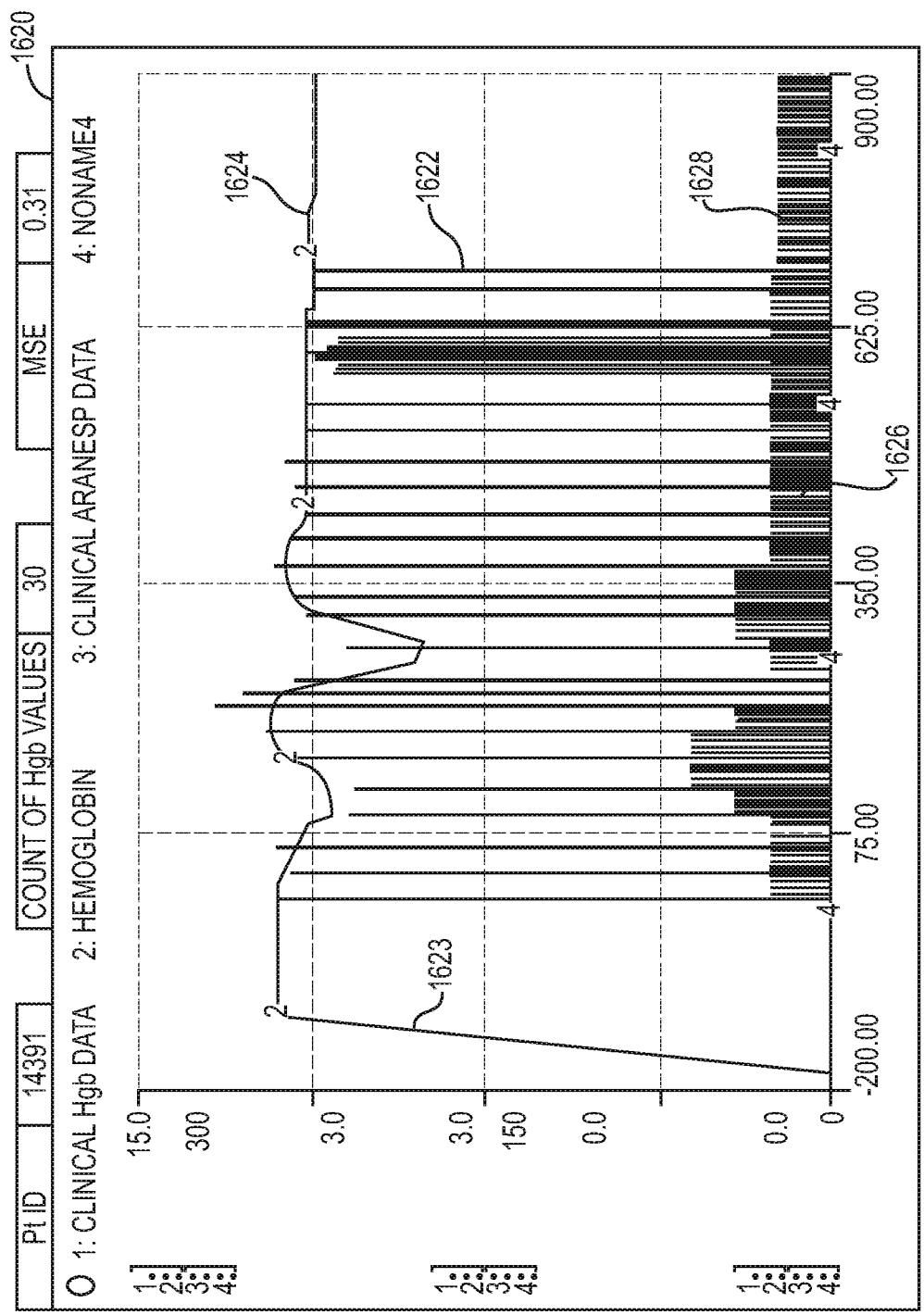
FIG. 35 is an example graph displaying historical Hgb levels, historical ESA dosages, and simulated Hgb levels for the pre-descriptive setup period, the descriptive period, and the prescriptive period of a patient.

FIG. 35 is an example graph 1620 displaying historical Hgb levels 1622, historical ESA dosages 1626, and simulated Hgb levels 1624 for the pre-descriptive setup period 1630, the descriptive period 1632, and the prescriptive period 1634. Graph 1620 also displays recommended ESA dosing 1628 for the prescriptive period, determined by simulated experiments described above. Graph 1620 could be displayed on, for example, user interface 1252 (FIG. 20) or other suitable user interface. Although specific data and graph are shown in FIG. 35, it shall be understood that the disclosure is not limited in this respect, and that other relevant data, graphs, tables, charts or other ways of displaying data may also be displayed, and that other types of functional interfaces, such as touch screen, mouse, stylus, keyboard, multi-touch, mobile devices, or other method of interacting with the program may be used without departing from the scope of the present disclosure.

The graph 1620 of FIG. 35 illustrates an example curve fitting result for the descriptive period 1632. In this example, the descriptive period for this patient was approximately 690 days in duration. During that period, 30 actual Hgb values were measured, and those values display a typical Hgb oscillation. 92 doses of Aranesp were administered in the descriptive phase. The model uses a so called pre-descriptive period 1630 to establish an erythropoietic equilibrium which simulates the Hgb value of the first observed Hgb result in the descriptive period, in this example equal to 12.8 g/dL. In this example, the pre-descriptive period 1630 in the model is 201 days in duration, running from day −200 to day 0. This is the period of time the simulation model requires to establish equilibrium in the presence of a theoretical (mathematically applied) daily ESA dose. Once the system determines the optimized therapeutic dose for a specific ESA, the system may further assist providers in finding the most effective combinations of available dosing levels at the optimal frequency of administration that will deliver the required therapeutic dose, and as a result, achieve and maintain the desired Hgb value. The recommended dosing regimen for the prescriptive period 1634 is indicated by 1628.

As mentioned above, although the examples were presented herein with respect to Aranesp and Epogen, it shall be understood that the ESA dosing techniques described herein may also be applicable to other types of ESA therapies, other patient populations and alternative routes of administration. In general, to apply the ESA dosing model to other ESA therapies, the ESA-specific constants ESA half life and ESA Kd would be entered into the ESA dosing model. For example, the ESA half life for the particular ESA would be taken into account in the model at the same point as the Aranesp half life 1418 in FIG. 27 or the Epogen half life 1486 in FIG. 30. Similarly, the ESA Kd for the particular ESA would be taken into account in the model at the same point as either the Aranesp Kd 1494 or the Epogen Kd 1516 as shown in FIG. 31. Those of skill in the art will appreciate that the ESA dosing model described herein may be applicable to a wide variety of ESA therapies, as well as to a wide variety of patient populations (ESRD patients, CKD patients, cancer therapy patients, HIV patients, or any other patient population having insufficient hemoglobin production and benefitting from ESA treatment). In addition, the ESA dosing model may also be applicable to multiple modes of delivery, including intravenous (IV) delivery, subcutaneous delivery, oral delivery, biopump, implantable drug delivery devices, etc.

The following are illustrative equations for the example model shown in FIGS. 21-33, as expressed in the syntax of a commercially available modeling application (iThink®, available from Isee Systems, Inc., in this example). Although an example implementation using iThink® is shown, it shall be understood that the ESA dosing techniques described herein may also be implemented using other commercially available or customized software applications.

ARENESP_AMOUNT(t) = ARENESP_AMOUNT(t − dt) + (ESA_input_picomoles − Arenesp_elimination) * dt
INIT ARENESP_AMOUNT = 0
INFLOWS:
ESA_input_picomoles = Aranesp_input_picomoles
OUTFLOWS:
Arenesp_elimination = ARENESP_AMOUNT * ( .693 / Aranesp_halftime )
BFU_INPUT_MC(t) = BFU_INPUT_MC(t − dt)
INIT BFU_INPUT_MC = RANDOM(BFU_INPUT_MIN,BFU_INPUT_MAX)
CFU\E[generation](t) = CFU\E[generation](t − dt) + (input[generation] − dividing_cells[generation] − apoptosis[generation]) * dt
INIT CFU\E[generation] = 0
INFLOWS:
input[generation] = IF ARRAYIDX ( ) = 1    THEN BFU_INPUT
ELSE
2 * dividing_cells[generation−1]
{ COMMENT OUT: IF ARRAYIDX ( ) = 1    THEN Noname_1
ELSE
2 * dividing_cells[generation−1] }
OUTFLOWS:
dividing_cells[generation] = CONVEYOR OUTFLOW
         TRANSIT TIME = replication_interval
apoptosis[1] = LEAKAGE OUTFLOW
         LEAKAGE FRACTION = 0
         NO-LEAK ZONE = 0%
apoptosis[2] = LEAKAGE OUTFLOW
         LEAKAGE FRACTION = 0
         NO-LEAK ZONE = 0%
apoptosis[3] = LEAKAGE OUTFLOW
         LEAKAGE FRACTION = 0
         NO-LEAK ZONE = 0%
apoptosis[4] = LEAKAGE OUTFLOW
         LEAKAGE FRACTION = 0
         NO-LEAK ZONE = 0%
apoptosis[5] = LEAKAGE OUTFLOW
         LEAKAGE FRACTION = 0
         NO-LEAK ZONE = 0%
apoptosis[6] = LEAKAGE OUTFLOW
         LEAKAGE FRACTION = 0
         NO-LEAK ZONE = 0%
apoptosis[7] = LEAKAGE OUTFLOW
         LEAKAGE FRACTION = 0
         NO-LEAK ZONE = 0%
apoptosis[8] = LEAKAGE OUTFLOW
         LEAKAGE FRACTION = 0
         NO-LEAK ZONE = 0%
apoptosis[9] = LEAKAGE OUTFLOW
         LEAKAGE FRACTION = 0
         NO-LEAK ZONE = 0%
apoptosis[10] = LEAKAGE OUTFLOW
         LEAKAGE FRACTION = 0
         NO-LEAK ZONE = 0%
apoptosis[11] = LEAKAGE OUTFLOW
         LEAKAGE FRACTION = ( 1 − fractional_apopt_sparing ) * (1 − CFU_SURV )
         NO-LEAK ZONE = 0%
apoptosis[12] = LEAKAGE OUTFLOW
         LEAKAGE FRACTION = 0
         NO-LEAK ZONE = 0%
CFU_SURV_MC(t) = CFU_SURV_MC(t − dt)
INIT CFU_SURV_MC = RANDOM(CFU_SURV_MIN , CFU_SURV_MAX)
Count_of_Hgb_Values(t) = Count_of_Hgb_Values(t − dt) + (Counting) * dt
INIT Count_of_Hgb_Values = 0
INFLOWS:
Counting = If CLINICAL_Hgb_Data > 0 THEN 1 ELSE 0
EPOGEN_AMT_pM(t) = EPOGEN_AMT_pM(t − dt) + (Epogen_input − Epogen_elim) * dt
INIT EPOGEN_AMT_pM = 0
INFLOWS:
Epogen_input = Epogen_input_picomoles
OUTFLOWS:
Epogen_elim = EPOGEN_AMT_pM * ( .693 / Epogen_halftime )
EPOR_MULT_MC(t) = EPOR_MULT_MC(t − dt)
INIT EPOR_MULT_MC = RANDOM ( EPOR_MULT_MIN , EPOR_MULT_MAX )
EPO_SETUP_RATE_MC(t) = EPO_SETUP_RATE_MC(t − dt)
INIT EPO_SETUP_RATE_MC = RANDOM ( EPO_SETUP_RATE_MIN , EPO_SETUP_RATE_MAX )
Eryth\Retic_development(t) = Eryth\Retic_development(t − dt) + (eryth_input − reticulocyte_prod − retic_atrophy) * dt
INIT Eryth\Retic_development = 0
         TRANSIT TIME = varies
         INFLOW LIMIT = INF
         CAPACITY = INF

```
INFLOWS:
eryth_input = erythroblast_production
OUTFLOWS:
reticulocyte_prod = CONVEYOR OUTFLOW
        TRANSIT TIME = maturation_time
retic_atrophy = LEAKAGE OUTFLOW
        LEAKAGE FRACTION = ( 1 − RETIC_SURV )
        NO-LEAK ZONE = 0%
P7_MC(t) = P7_MC(t − dt)
INIT P7_MC = RANDOM ( P7_MIN , P7_MAX )
RBCs(t) = RBCs(t − dt) + (reticulocytes_maturing − RBCs_lysing − hem_RBC_from_circul) * dt
INIT RBCs = 0
        TRANSIT TIME = varies
        INFLOW LIMIT = INF
        CAPACITY = INF
INFLOWS:
reticulocytes_maturing = CONVEYOR OUTFLOW
OUTFLOWS:
RBCs_lysing = CONVEYOR OUTFLOW
        TRANSIT TIME = RBC_LIFESPAN
hem_RBC_from_circul = LEAKAGE OUTFLOW
        LEAKAGE FRACTION = If HEM >0 Then HEM Else 0
        NO-LEAK ZONE = 0%
RBC_LIFESPAN_MC(t) = RBC_LIFESPAN_MC(t − dt)
INIT RBC_LIFESPAN_MC = RANDOM ( RBC_LIFESPAN_MIN , RBC_LIFESPAN_MAX )
reticulocytes_in_circulation(t) = reticulocytes_in_circulation(t − dt) + (reticulocyte_release_from_marrow −
reticulocytes_maturing − hem_reticul_from_circul) * dt
INIT reticulocytes_in_circulation = 0
        TRANSIT TIME = 2
        INFLOW LIMIT = INF
        CAPACITY = INF
INFLOWS:
reticulocyte_release_from_marrow = reticulocyte_prod
OUTFLOWS:
reticulocytes_maturing = CONVEYOR OUTFLOW
hem_reticul_from_circul = LEAKAGE OUTFLOW
        LEAKAGE FRACTION = If HEM >0 Then HEM Else 0
        NO-LEAK ZONE = 0
RETIC_SURV_MC(t) = RETIC_SURV_MC(t − dt)
INIT RETIC_SURV_MC = RANDOM ( RETIC_SURV_MIN , RETIC_SURV_MAX )
Summed_Squared_Difference(t) = Summed_Squared_Difference(t − dt) + (Summing) * dt
INIT Summed_Squared_Difference = 0
INFLOWS:
Summing = Squared_Difference
Aranesp_Conc_pM = ARENESP_AMOUNT / Vol_of_Dist
Aranesp_halftime = 25/24
Aranesp_input_picomoles = ( ARANESP_INPUT_ug ) * 1e6 / 37100
ARANESP_INPUT_ug = setup_EPO_input + (
IF time < Ar_DOSE_A_START
THEN Historical_Aranesp_doses
ELSE Rx_protocol
)
Aranesp_Kd = 400E−12
ARANESP_switch = 1
Aranesp_WTD = IF Time < First_Prescriptive_Sim_Day_Number THEN 0
ELSE
PULSE(Example_2_Weekly_Therapeutic_Aranesp_Dose_Amount,First_Prescriptive_Sim_Day_Number,7)
Ar_dose_A = IF ( TIME < Ar_dose_A_end )
THEN PULSE ( Ar_dose_A_amt , Ar_DOSE_A_START , Ar_dose_A_interval )
ELSE 0
Ar_dose_A_interval = 7
Ar_DOSE_A_START = 700
Ar_dose_A_amt = 0
Ar_dose_A_end = 900
Ar_dose_B = IF ( TIME < Ar_dose_end )
THEN PULSE ( Ar_dose_B_amt , Ar_DOSE_B_START , Ar_dose_B_interval )
ELSE 0
Ar_dose_B_amt = 0
Ar_dose_B_interval = 0
Ar_DOSE_B_START = 700
AR_dose_C = IF ( TIME < Ar_dose_C_end )
THEN PULSE ( AR_dose_C_amt , Ar_DOSE_C_START , Ar_dose_C_interval )
ELSE 0
Ar_dose_C_end = 0
Ar_DOSE_C_START = 700
AR_dose_C_amt = 0
Ar_dose_C_interval = 0
Ar_dose_end = 0
avg_lifetime_CALC = 86.0699996948242
```

-continued

```
baseline_blast_mortality_fraction_CALC = 0.680000007152557
baseline_reticulocyte_mortality_fraction_CALC = 0.569999992847443
BFU_INPUT = IF Monte_Carlo_switch = 1 THEN BFU_INPUT_MC ELSE BFU_INPUT_CALC
BFU_INPUT_CALC = 90.62
BFU_INPUT_MAX = 1e9
BFU_INPUT_MIN = 5e7
Body_Wt = 70
CFU_SURV = IF Monte_Carlo_switch = 1 THEN CFU_SURV_MC ELSE CFU_SURV_CALC
CFU_SURV_CALC = 1.24
CFU_SURV_MAX = .35
CFU_SURV_MIN = .01
Current_Excel_Day_Number = Sim_Start_Excel_Day_Number+Time-2
EC50_CALC = 23.1800003051758
Epg_dose_amt_A = 0
Epg_dose_amt_B = 0
Epg_dose_amt_C = 0
Epg_dose_A_1 = IF ( TIME < Epg_dose_end_A - 3 )
THEN PULSE ( Epg_dose_amt_A , Epg_DOSE_START_A, 7 )
ELSE 0
Epg_dose_A_2 = IF ( TIME < Epg_dose_end_A - 1 )
THEN PULSE ( Epg_dose_amt_A , Epg_DOSE_START_A + 2 , 7 )
ELSE 0
Epg_dose_A_3 = IF ( TIME < Epg_dose_end_A + 1 )
THEN PULSE ( Epg_dose_amt_A , Epg_DOSE_START_A +4 , 7 )
ELSE 0
Epg_dose_B_1 = IF ( TIME < Epg_dose_end_B - 3 )
THEN PULSE ( Epg_dose_amt_B , Epg_DOSE_START_B , 7 )
ELSE 0
Epg_dose_B_2 = IF ( TIME < Epg_dose_end_B - 1 )
THEN PULSE ( Epg_dose_amt_B , Epg_DOSE_START_B + 2 , 7 )
ELSE 0
Epg_dose_B_3 = IF ( TIME < Epg_dose_end_B + 1 )
THEN PULSE ( Epg_dose_amt_B , Epg_DOSE_START_B +4 , 7 )
ELSE 0
Epg_dose_C_1 = IF ( TIME < Epg_dose_end_C - 3 )
THEN PULSE ( Epg_dose_amt_C , Epg_DOSE_START_C, 7 )
ELSE 0
Epg_dose_C_2 = IF ( TIME < Epg_dose_end_C - 1 )
THEN PULSE ( Epg_dose_amt_C , Epg_DOSE_START_C + 2 , 7 )
ELSE 0
Epg_dose_C_3 = IF ( TIME < Epg_dose_end_C + 1 )
THEN PULSE ( Epg_dose_amt_C , Epg_DOSE_START_C +4 , 7 )
ELSE 0
Epg_dose_end_A = 1000
Epg_dose_end_B = 1000
Epg_dose_end_C = 1000
Epg_DOSE_START_A = 1000
Epg_DOSE_START_B = 1000
Epg_DOSE_START_C = 1000
Epg_Rx_regimen_A = Epg_dose_A_1 + Epg_dose_A_2 + Epg_dose_A_3
Epg_Rx_regimen_B = Epg_dose_B_1 + Epg_dose_B_2 + Epg_dose_B_3
Epg_Rx_regimen_C = Epg_dose_C_1 + Epg_dose_C_2 + Epg_dose_C_3
Epogen_Conc_pM = EPOGEN_AMT_pM / Vol_of_Dist
Epogen_halftime = 1.2
Epogen_input_picomoles = ( EPOGEN_INPUT_U ) * 1e6 /37100
EPOGEN_INPUT_U = setup_Epogen_input_U + (
IF time < Epg_DOSE_START_A
THEN Historical_Epogen_doses_U
ELSE Epogen_Rx_Pulses
)
Epogen_Kd = 50e-12
Epogen_PSTD = IF Time < First_Prescriptive_Sim_Day_Number THEN 0
ELSE PULSE(Example_2_Per_Session_Epogen_Therapeutic_Dose,First_Prescriptive_Sim_Day_Number,7)
Epogen_Rx_Pulses = (WTD_Switch - 1) * (Epg_Rx_regimen_A + Epg_Rx_regimen_B + Epg_Rx_regimen_C)
+ WTD_Switch*Epogen_PSTD
EPOGEN_switch = 0
EPOR_fraction_bound = ARANESP_switch * (Aranesp_Conc_pM * 1e-12) / ( Aranesp_Kd +
(Aranesp_Conc_pM * 1e-12 ) ) +
EPOGEN_switch * ( Epogen_Conc_pM * 1e-12) / ( Epogen_Kd + (Epogen_Conc_pM * 1e-12 ) )
EPOR_MULT = IF Monte_Carlo_switch = 1 THEN EPOR_MULT_MC ELSE EPOR_MULT_CALC
EPOR_MULT_CALC = 9.1
EPOR_MULT_MAX = 10
EPOR_MULT_MIN = 1
EPO_SETUP_RATE_CALC = 90.95
EPO_SETUP_RATE_MAX = 40
EPO_SETUP_RATE_MIN = 1
EPO_SETUP_RATE = IF Monte_Carlo_switch = 1 THEN EPO_SETUP_RATE_MC ELSE
EPO_SETUP_RAIE_CALC
erythroblast_production = dividing_cells[12]
```

-continued

```
erythroblast_production_CALC = 69.5800018310547
Example_2_Per_Session_Epogen_Therapeutic_Dose = 26
Example_2_Weekly_Therapeutic_Aranesp_Dose_Amount = 26
Example_Weekly_Therapeutic_Dose_Amount = 0
First_Prescriptive_Excel_Day_Number = 40482
First_Prescriptive_Sim_Day_Number = First_Prescriptive_Excel_Day_Number–
Sim_Start_Excel_Day_Number+2
fractional_apopt_sparing = MIN ( EPOR_fraction_bound * EPOR_MULT , 1)
HEM = 0
HEMATOCRIT = 42 * ( total_cells_in_circulation / Vol_of_Dist ) / 5e12
HEMOGLOBIN = HEMATOCRIT * .34
hepatic_EPO_CALC = 0
hgb_high = 12
hgb_low = 10
Historical_Aranesp_doses =
IF ((mod(time,1) = .5) AND (CLINICAL_ARANESP_DATA > 1))
THEN (Pulse ( CLINICAL_ARANESP_DATA , time , 99999))
ELSE 0
Historical_Epogen_doses_U =
IF ((mod(time,1) = .5) AND (CLINICAL_EPOGEN_DATA > 1))
THEN (Pulse ( CLINICAL_EPOGEN_DATA , time, 99999))
ELSE 0
Last_Descriptive_Excel_Day_Number = 40480
maturation_time = 6
Monte_Carlo_switch = 0
MSE = if Count_of_Hgb_Values > 0 THEN (Summed_Squared_Difference / Count_of_Hgb_Values) ELSE 0
P7 = IF Monte_Carlo_switch = 1 THEN P7_MC ELSE P7_CALC
P7_CALC = 0
P7_MAX = 100
P7_MIN = 50
Plotted_Aranesp_Rx_Doses = 0 {Aranesp_Pulse / 8}
plot_AR_dose_A = Ar_dose_A/8
plot_historical_Ar_dose = Historical_Aranesp_doses/8
plot_setup_EPO_input = setup_EPO_input/8
Pt_ID = 6198
RBC_LIFESPAN = IF Monte_Carlo_switch = 1 THEN RBC_LIFESPAN_MC ELSE RBC_LIFESPAN_CALC
RBC_LIFESPAN_CALC = 61.06
RBC_LIFESPAN_MAX = 120
RBC_LIFESPAN_MIN = 40
replication_interval = 1
RETIC_SURV = IF Monte_Carlo_switch = 1 THEN RETIC_SURV_MC ELSE RETIC_SURV_CALC
RETIC_SURV_CALC = 96.03
RETIC_SURV_MAX = .8
RETIC_SURV_MIN = .2
Rx_protocol = (1 – Aranesp_WTD) * (Ar_dose_A + Ar_dose_B + AR_dose_C) +
WTD_Switch*Aranesp_WTD
Scenario = 1
setup_Epogen_input_U = IF time < 8 THEN PULSE ( EPO_SETUP_RATE, –200, 2.33 ) ELSE 0
setup_EPO_input = IF time < 8 THEN PULSE ( EPO_SETUP_RATE, –200, 7 ) ELSE 0
setup_EPO_rate_CALC = 2.95000004768372
SimDays_in_Descriptive_Period = Last_Descriptive_Excel_Day_Number–Sim_Start_Excel_Day_Number+1
Sim_Day_Number = Time
Sim_Start_Excel_Day_Number = 40030
Squared_Difference = If CLINICAL_Hgb_Data > 0 Then (HEMOGLOBIN – CLINICAL_Hgb_Data)'Else 0
sugg_BFU_max = BFU_INPUT_CALC * 2
sugg_BFU_min = BFU_INPUT_CALC / 2
sugg_CFU_surv_max = MIN ( CFU_SURV_CALC + .2, .80 )
sugg_CFU_surv_min = MAX ( CFU_SURV_CALC – .2, .20 )
sugg_EPOR_mult_max = MIN ( EPOR_MULT_CALC * 2 , 10 )
sugg_EPOR_mult_min = MAX ( EPOR_MULT_CALC / 2 , 1 )
sugg_EPO_setup_max = MIN ( EPO_SETUP_RATE_CALC * 2, 30 )
sugg_EPO_setup_min = MAX ( EPO_SETUP_RATE_CALC / 2, 1 )
sugg_RBC_LIFE_max = RBC_LIFESPAN_CALC + 20
sugg_RBC_LIFE_min = RBC_LIFESPAN_CALC – 20
sugg_retic_surv_max = MIN ( RETIC_SURV_CALC + 0.2, .80 )
sugg_retic_surv_min = MAX ( RETIC_SURV_CALC – 0.2 , .20 )
total_cells_in_circulation = reticulocytes_in_circulation + RBCs
Vol_of_Dist = Body_Wt * .07
WTD_Switch = 0
```

The techniques described in this disclosure, including functions performed by a processor, controller, control unit, or control system, may be implemented within one or more of a general purpose microprocessor, digital signal processor (DSP), application specific integrated circuit (ASIC), field programmable gate array (FPGA), programmable logic devices (PLDs), or other equivalent logic devices. Accordingly, the terms "processor" "processing unit" or "controller," as used herein, may refer to any one or more of the foregoing structures or any other structure suitable for implementation of the techniques described herein.

The various components illustrated herein may be realized by any suitable combination of hardware, software, or firmware. In the figures, various components are depicted as separate units or modules. However, all or several of the various components described with reference to these figures may be integrated into combined units or modules within common hardware, firmware, and/or software. Accordingly, the representation of features as components, units, or modules is intended to highlight particular functional features for ease of illustration, and does not necessarily require realization of such features by separate hardware, firmware, or software components. In some cases, various units may be implemented as programmable processes performed by one or more processors or controllers.

Any features described herein as modules, devices, or components may be implemented together in an integrated logic device or separately as discrete but interoperable logic devices. In various aspects, such components may be formed at least in part as one or more integrated circuit devices, which may be referred to collectively as an integrated circuit device, such as an integrated circuit chip or chipset. Such circuitry may be provided in a single integrated circuit chip device or in multiple, interoperable integrated circuit chip devices, and may be used in any of a variety of pharmaceutical applications and devices.

If implemented in part by software, the techniques may be realized at least in part by a computer-readable data storage medium comprising code with instructions that, when executed by one or more processors or controllers, performs one or more of the methods described in this disclosure. The computer-readable storage medium may form part of a computer program product, which may include packaging materials. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), embedded dynamic random access memory (eDRAM), static random access memory (SRAM), flash memory, magnetic or optical data storage media. Any software that is utilized may be executed by one or more processors, such as one or more DSP's, general purpose microprocessors, ASIC's, FPGA's, or other equivalent integrated or discrete logic circuitry.

Various examples have been described. These and other examples are within the scope of the following claims.

The invention claimed is:
1. A method of treating anemia in a patient comprising:
receiving patient-specific historical hemoglobin (Hgb) data for the patient and corresponding patient-specific historical erythropoietic stimulating agent (ESA) dosage data for the patient obtained during a pre-descriptive setup period and a descriptive period;
estimating patient-specific Hgb values for each of a plurality of parameters of a biophysical simulation model that represents a process by which red blood cells are produced in humans based on the patient-specific historical Hgb data and the corresponding patient-specific historical ESA dosage data;
simulating patient-specific Hgb values for the pre-descriptive setup period, the descriptive period and a future prescriptive period based on the estimated patient-specific Hgb values for each of the plurality of parameters of the biophysical simulation model and a plurality of therapeutic ESA dosages;
identifying at least one of the plurality of therapeutic ESA dosages that maintains the simulated patient-specific Hgb values within a target range during the future prescriptive period and without cycling of the patient-specific Hgb values above or below the target range during the prescriptive period; and
administering one of the identified therapeutic ESA dosages to the patient,
wherein the plurality of parameters of the biophysical simulation model includes a red blood cell lifespan parameter that accounts for a delay in a decrease of the simulated patient-specific Hgb values as a result of an average lifespan of a red blood cell.

2. The method of claim 1 wherein estimating the patient-specific Hgb values for each of the plurality of sets of parameters comprises applying Monte Carlo methods to estimate the patient-specific Hgb values.

3. The method of claim 1, further comprising identifying one or more commercially available dosing regimens that deliver the equivalent of the therapeutic dose.

4. The method of claim 1 wherein the plurality of parameters include one or more of a Blast Forming Unit Input, a Colony Forming Unit Survival, a Reticulocyte Survival, an Erythropoietin Receptor Multiplier, a Red Blood Cell Lifespan, and an Erythropoietin Setup Rate.

5. The method of claim 1 wherein the plurality of parameters of the biophysical simulation model includes an erythropoietin setup rate parameter having a patient-specific value that when applied to the biophysical simulation model during the pre-descriptive setup period raises the simulated patient-specific Hgb values to a level equal to the patient-specific historical Hgb data on a first day of the descriptive period.

6. The method of claim 1 wherein the ESA is one of erythropoietin, recombinant human erythropoietin, epoetin alpha, epoetin beta, darbepoetin alpha, and methoxy polyethylene glycol-epoetin beta.

7. The method of claim 1 wherein the biophysical simulation model includes taking into account delay in increase of simulated patient-specific Hgb values in response to delivery of the proposed therapeutic ESA dosages.

8. The method of claim 1 wherein the biophysical simulation model includes a patient-specific parameter corresponding to increased survival rate of erythroblast precursor cells in bone marrow of the patient in presence of an ESA.

9. The method of claim 1 wherein the biophysical simulation model includes a patient-specific parameter corresponding to increased survival rate of reticulocytes in bone marrow of the patient in presence of an ESA.

10. The method of claim 1 wherein the biophysical simulation model includes a patient-specific parameter corresponding to a lifespan of red blood cells in the patient.

11. The method of claim 1 wherein the patient has one of chronic kidney disease or end stage renal disease.

12. The method of claim 1 wherein the patient is a cancer therapy patient.

13. The method of claim 1 further including administering the identified therapeutic dose to the patient by any of intravenous (IV) delivery, subcutaneous delivery, oral delivery, biopump delivery, and an implantable device drug delivery.

14. The method of claim 1 wherein identifying at least one of the plurality of therapeutic ESA dosages that maintains the simulated patient-specific Hgb values within a target range during the future prescriptive period of time without cycling of the patient-specific Hgb values above and below the target range during the future prescriptive period of time includes identifying one of the plurality of therapeutic ESA dosages that maintains the simulated patient-specific Hgb values at a target Hgb level within the target range during the future prescriptive period of time.

15. A method of treating anemia in a patient, comprising:
receiving patient-specific historical hemoglobin (Hgb) data and corresponding patient-specific historical erythropoietic stimulating agent (ESA) dosage data obtained during a pre-descriptive setup period and during a descriptive period;
estimating patient-specific values for each of a plurality of parameters of a biophysical simulation model that represents a process by which red blood cells are produced in humans based on the patient-specific historical Hgb data and the corresponding patient-specific historical ESA dosage data,
wherein the plurality of parameters of the biophysical simulation model includes a red blood cell lifespan parameter that accounts for a delay in a decrease of the simulated patient-specific Hgb values as a result of an average lifespan of a red blood cell;
simulating patient-specific Hgb values for the pre-descriptive set up period, the descriptive period and a prescriptive period based on the estimated patient-specific values for each of the plurality of parameters of the biophysical simulation model and a plurality of therapeutic ESA dosages;
identifying at least one of the plurality of therapeutic ESA dosages that eliminates cycling of the simulated patient-specific Hgb values above or below a target range and maintains the simulated patient-specific Hgb values within the target range during the prescriptive period; and
administering one of the identified therapeutic ESA dosages to the patient.

16. The method of claim 15 wherein the patient has one of chronic kidney disease or end stage renal disease.

17. The method of claim 15 wherein the ESA is one of erythropoietin, recombinant human erythropoietin, epoetin alpha, epoetin beta, darbepoetin alpha, and methoxy polyethylene glycol-epoetin beta.

18. The method of claim 15 wherein the biophysical simulation model accounts for delay in increase of simulated patient-specific Hgb values in response to delivery of the proposed therapeutic ESA dosages.

19. The method of claim 15 wherein identifying at least one of the plurality of therapeutic ESA dosages includes identifying at least one of the plurality of therapeutic ESA dosages that maintains the simulated patient-specific Hgb values at a target Hgb level during the prescriptive period of time.

* * * * *